United States Patent
Ohrai et al.

(10) Patent No.: US 7,879,887 B2
(45) Date of Patent: Feb. 1, 2011

(54) α-AMINO ACID DERIVATIVES AND MEDICAMENTS CONTAINING THE SAME AS AN ACTIVE INGREDIENT

(75) Inventors: Kazuhiko Ohrai, Funabashi (JP); Michiaki Adachi, Funabashi (JP); Koji Toyama, Funabashi (JP); Takanori Shimizu, Funabashi (JP); Keishi Hayashi, Funabashi (JP); Masataka Minami, Funabashi (JP); Yoshiyuki Suzuki, Gotenba (JP); Masakazu Sugiyama, Gotenba (JP); Masateru Ohta, Gotenba (JP); Shojiro Kadono, Gotenba (JP); Takuya Shiraishi, Gotenba (JP); Haruhiko Sato, Gotenba (JP); Yoshiaki Watanabe, Gotenba (JP); Nobuya Ishii, Kamakura (JP); Masahiro Sakaitani, Kamakura (JP); Masami Hasegawa, Kamakura (JP)

(73) Assignees: Nissan Chemical Industries, Ltd., Tokyo (JP); Chugai Seiyaku Kabushiki Kaisha, Tokyo (JP)

( * ) Notice: Subject to any disclaimer, the term of this patent is extended or adjusted under 35 U.S.C. 154(b) by 14 days.

(21) Appl. No.: 12/306,901

(22) PCT Filed: Jun. 29, 2007

(86) PCT No.: PCT/JP2007/063092
§ 371 (c)(1),
(2), (4) Date: Dec. 29, 2008

(87) PCT Pub. No.: WO2008/001883
PCT Pub. Date: Jan. 3, 2008

(65) Prior Publication Data
US 2009/0275623 A1 Nov. 5, 2009

(30) Foreign Application Priority Data
Jun. 29, 2006 (JP) .............................. 2006-179704
Sep. 28, 2006 (JP) .............................. 2006-265957

(51) Int. Cl.
C07D 513/04 (2006.01)
A61K 31/429 (2006.01)

(52) U.S. Cl. ...................................... 514/366; 548/151
(58) Field of Classification Search ................. 548/151
See application file for complete search history.

(56) References Cited

U.S. PATENT DOCUMENTS 4,831,032 A 5/1989 von der Saal et al.
(Continued)

FOREIGN PATENT DOCUMENTS

JP 62-010090 A 1/1987
(Continued)

OTHER PUBLICATIONS

Rautio et al. Nature Reviews Drug Discovery 2008, 7, pp. 255-270.*
(Continued)

Primary Examiner—Rebecca L Anderson
Assistant Examiner—Matthew P Coughlin
(74) Attorney, Agent, or Firm—Birch, Stewart, Kolasch & Birch, LLP

(57) ABSTRACT

The present invention provides novel α-amino acid derivatives of formula (1):

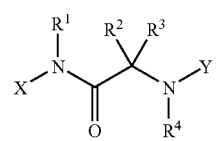

(wherein, $R^1$, $R^2$, $R^3$, $R^4$, X and Y are as defined in the claims) or pharmaceutically acceptable salts, prodrugs or solvates thereof. The derivatives of formula (1) have βARK1 inhibitory activity and are useful for preventing or treating heart failure. Moreover, the derivatives of formula (1) also have antitumor activity, particularly dual inhibitory activity on Aurora kinase and CDK, and are useful for cell proliferative diseases such as cancer.

14 Claims, 1 Drawing Sheet

U.S. PATENT DOCUMENTS

| | | |
|---|---|---|
| 6,291,504 B1 | 9/2001 | Nugiel et al. |
| 2005/0119159 A1 | 6/2005 | Suzuki et al. |
| 2006/0135516 A1 | 6/2006 | Berdini et al. |

FOREIGN PATENT DOCUMENTS

| | | |
|---|---|---|
| JP | 62010090 A * | 1/1987 |
| JP | 9-505029 A | 5/1997 |
| JP | 11-130761 A | 5/1999 |
| JP | 2003-321472 A | 11/2003 |
| JP | 2004-524277 A | 8/2004 |
| JP | 2006-502133 A | 1/2006 |
| WO | WO-95/03298 A1 | 2/1995 |
| WO | WO 02/18350 A1 | 3/2002 |
| WO | WO 02/27314 A1 | 4/2002 |
| WO | WO 02/057240 A1 | 7/2002 |
| WO | WO 03/020312 A1 | 3/2003 |
| WO | WO-2004/014922 A1 | 2/2004 |
| WO | WO-2005/011693 A1 | 2/2005 |
| WO | WO-20051019190 A2 | 3/2005 |

PUBLICATIONS

Wang et al. Drug Delivery: Principles and Applications, 2005 John Wiley & Sons, Inc. Publication, Section 8.3, pp. 136-137.*

Smith, D. A. Current Opinion in Drug Discovery & Development 2007, 10, 550-559.*

Testa, B. Current Opinion in Chemical Biology 2009, 13, pp. 338-344.*

Giron, D. J. Therm. Anal. Cal. 2001, 64, pp. 37-60.*

Giron, D. J. Therm. Anal. Cal. 2002, 68, pp. 335-357.*

B. Rodriquez-Spong et al. Advanced Drug Delivery Reviews, 2004, 56, pp. 241-274.*

Souillac, et al., Characterization of Delivery Systems, Differential Scanning Calorimetry, pp. 217-218 (in Encyclopedia of Controlled Drug Delivery, 1999, John Wiley & Sons, pp. 212-227).*

Luo et al. (Cell, 2009, 136, pp. 823-837).*

Bischoff et al., "A homologue of Drosophila aurora kinase is oncogenic and amplified in human colorectal cancers," The EMBO Journal, 1998, vol. 17, No. 11, pp. 3052-3065.

Crane et al., "Aurora A, Meiosis and Mitosis," Biology of the Cell, 2003, vol. 96, pp. 215-229.

Fancelli & Moll, "Inhibitors of Aurora kinases for the treatment of cancer," Expert Opin. Ther. Patents, 2005, vol. 15, No. 9, pp. 1169-1182.

Harding et al., "Cardiac Beta-ARK1 inhibition prolongs survival and augments Beta blocker therapy in a mouse model of severe heart failure," PNAS, May 8, 2001, vol. 98, No. 10, pp. 5809-5814.

Pevarello & Villa, "Cyclin-dependent kinase inhibitors: a survey of the recent patent literature," Expert Opin. Ther. Patents, 2005, vol. 15, No. 6, pp. 675-703.

Ren & Rollins, "Cyclin C/Cdk3 Promotes Rb-Dependent G0 Exit," Cell, Apr. 16, 2004, vol. 117, pp. 239-251.

Rockman et al., "Expression ofa Beta-adrenergic receptor kinase 1 inhibitor prevents the development of myocardial failure in gene-targeted mice," Proc. Natl. Acad. Sci. USA, Jun. 1998, vol. 95, pp. 7000-7005.

Sanchez & Dynlacht, "New insights into cyclins, CDKs, and cell cycle control," Seminars in Cell & Developmental Biology, 2005, vol. 16, pp. 311-321.

Saya & Hirota, "Regulation of mitotic events by mitotic kinases," Jikken Igaku, 2004, vol. 22, No. 9, pp. 1237-1241 (with English abstract).

Shah et al., "In Vivo Ventricular Gene Delivery of Beta-Adrenergic Receptor Kinase Inhibitor to the Failing Heart Reverses Cardiac Dysfunction," Circulation, 2001, vol. 103, pp. 1311-1316.

Sherr, Charles J., "G1 Phase Progression: Cycling on Cue," Cell, Nov. 18, 1994, vol. 79, pp. 551-555.

Ungerer et al., "Altered Expression of Beta-Adrenergic Receptor Kinase and Beta1-Adrenergic Receptors in the Failing Human Heart," Circulation, 1993, vol. 87, pp. 454-463.

Ungerer et al., "Expression of Beta-Arrestins and Beta-Adrenergic Receptor Kinases in the Failing Human Heart," Circ. Res., 1994, vol. 74, pp. 206-213.

White et al., "Preservation of myocardial beta-adrenergic receptor signaling delays and the development of heart failure after myocardial infarction," PNAS, May 9, 2000, vol. 97, No. 10, pp. 5428-5433.

Zariwala et al., "Cyclin E2, a novel human G1 cyclin and activating partner of CDK2 and CDK3, is induced by viral oncoproteins," Oncogene, 1998, vol. 17, pp. 2787-2798.

Stuart Emanuel et al., Cancer Res., Oct. 1, 2005, vol. 65, No. 19, pp. 9038-9046.

Minoru Iino et al., J. Med. Chem., May 23, 2002, vol. 45, No. 11, p. 2150-2159 (ABS only).

* cited by examiner

α-AMINO ACID DERIVATIVES AND MEDICAMENTS CONTAINING THE SAME AS AN ACTIVE INGREDIENT

TECHNICAL FIELD

The present invention relates to novel α-amino acid derivatives. These derivatives have βARK-1 inhibitory activity and are useful for preventing or treating heart failure. Moreover, these derivatives also have antitumor activity, in particular, dual inhibitory activity on Aurora kinase and CDK, and are useful for cell proliferative diseases such as cancer.

BACKGROUND ART

G protein-coupled receptor kinase (GRK) is an enzyme for phosphorylation and desensitization of G protein-coupled receptors (GPCR) activated by an agonist. Research on the physiological functions of members of the GRK family has been conducted primarily focusing on a member of that family in the form of β adrenergic receptor kinase 1 (βARK1=GRK2) and on a member of the GPCR family in the form of β adrenergic receptor (βAR). Although there are reports suggesting that GRK is involved in the formation of the pathology of various diseases, the relationship between cardiac βAR phosphorylation and desensitization by βARK1 and the pathology of heart failure has been the subject of the greatest research.

In the heart of a patient with heart failure, it is well known that the expressed amount of βARK1 mRNA increases remarkably and desensitization of cardiac βAR occurs (see, for example, Non-Patent Documents 1 and 2). A similar result has been obtained in various animal models of heart failure, and it's believed that cardiac βAR phosphorylation and desensitization by βARK1 is a causative factor of exacerbating the pathology of heart failure.

Since βARK1 is activated as a result of being translocated to the cell membrane by bonding Gβγ and the C terminal thereof, the preventive and therapeutic effects on the pathology of heart failure by inhibition of βARK1 can be examined by expressing the C terminal of βARK1 (βARKct: peptide composed of the 495th to 689th amino acids) as dominant negative βARK1 in the hearts of various heart failure animal models. For example, improvement of cardiac function by introduction of βARKct into the hearts of a rabbit post-myocardial infarction heart failure model (see, for example, Non-Patent Documents 3 and 4), the suppression of the onset of heart failure in muscle LIM protein knockout (MLP−/−) mice by crossing a dilated cardiomyopathy model in the form of MLP−/− mice with βARKct transgenic mice (see, for example, Non-Patent Document 5), the suppression of reduction of cardiac function and death in calsequestrin (CSQ) transgenic mice by crossing a dilated cardiomyopathy model n the form of CSQ transgenic mice with βARKct transgenic mice (see, for example, Non-Patent Document 6), and the suppression of death due to post-myocardial infraction heart failure in βARKct transgenic mice (see, for example, Patent Document 1) have been previously reported. Thus, βARK1 inhibitors are thought to be promising as preventives and therapeutics for heart failure.

However, although there have been some reports thus far relating to compounds having βARK1 inhibitory activity (see, for example, Non-Patent Document 7 and Patent Documents 2 to 4), there have yet to be any reports relating to α-amino acid derivatives having βARK1 inhibitory activity.

Although cardiotonics, β-blockers, inhibitors of angiotensin-converting enzyme, angiotensin II antagonists and calcium antagonists and the like are currently used to treat heart failure, since cardiotonics are associated with an increased mortality rate caused by long-term administration, the effects of inhibitors of angiotensin-converting enzyme and angiotensin II antagonists are insufficient, and β-blockers have the disadvantage of requiring hospitalized monitoring due to the negative inotropic action thereof, a drug is sought that is safer and more highly effective.

On the other hand, the majority of the cells of the human body do not undergo cell division except for in the case of requiring cell regeneration such as during tissue damage. However, certain limited cells such as tumor cells proliferate at a certain frequency. Such cells are referred to as being in a "cell cycle". The cell cycle consists of four stages in a predetermined sequence, and these are referred to as the G1 stage, S stage, G2 stage and M stage. Progression of the cell cycle is precisely controlled by various kinases such as cyclin-dependent kinase (CDK) and Aurora kinase. As the relationship between disruption of the cell cycle and tumor formation and proliferation has become clearer, the importance of cell cycle research has enhanced on the basis of it being potentially intimately involved in the essential nature of tumors. On the basis of this background, although research has conventionally been conducted on the manner in which the cell cycle progresses, the control mechanisms of the cell cycle and methods for inhibiting the cell cycle in order to elucidate the mechanism of tumors and develop pharmaceuticals, analysis of the cell cycle has recently become an important analytical tool in fields such as cell death, aging and regeneration as well.

Aurora kinase, which is a kind of serine-threonine kinase, is known to exist in the form of three types of subtypes (Aurora A, B and C) having high homology between the kinase domains of the C terminal. These subtypes are collectively referred to as the Aurora family. On the basis of previous research, the Aurora family has been determined to be essential for accurately controlling mitosis, including separation of the centromere in the mitosis stage and bipolar spindle formation (see, for example, Non-Patent Document 8). The relationship between Aurora kinase and tumors began with reports describing the over-expression of Aurora-A and Aurora-B in colon cancer (see, for example, Non-Patent Document 9), and were followed by reports indicating that Aurora-A is highly expressed in numerous tumors such as breast cancer, ovarian cancer, liver cancer, gastric cancer and pancreatic cancer. In addition, results have also been reported indicating that cancer patients in which Aurora kinase is expressed at high levels have a poor prognosis (see, for example, Non-Patent Document 10), and several Aurora kinase inhibitors are known to be currently undergoing clinical evaluation.

Cyclin-dependent kinase (CDK), which is also a serine-threonine kinase, also plays an extremely important role in regulation of the cell cycle. This kinase precisely controls the cell cycle by expressing its function as a result of forming complexes specific to the cell cycle between enzyme subunits having enzyme activity in the form of CDK1, CDK2, CDK3, CDK4 or CDK6 and activity-regulating subunits expressed specifically to the cell cycle in the form of cyclins A, B, D1, D2, D3 and E (in the present description, complexes composed of catalyst subunits in the form of CDK# and activity-regulating subunits in the form of cyclin* are represented as "CDK#/cyclin*" complexes) (see, for example, Non-Patent Document 11).

For example, CDK1/cyclin B complex is required for progression from the G2 stage to the M stage of the cell cycle, and is also required to complete mitosis (see, for example, Non- Patent Document 12). The CDK2/cyclin E complex controls progression from the G1 stage to the S stage (see, for example, Non-Patent Document 13). CDK3 is thought to function in progression to the G1 stage and although it was thought to be important in G1-S progression (see, for example, Non-Patent Document 14), according to more recent reports, cells not present in the cell stage (G0 cells) have been reported to function during progression to the G1 stage in order to initiate cell proliferation (see, for example, Non-Patent Document 15).

Mutation and high expression of CDK and cyclin genes have been frequently reported in numerous genes similar to the Aurora family. As a result, attention has been focused on CDK as well as an important target molecule for cancer therapy, and numerous pharmaceutical companies are proceeding with research and development of low molecular weight compounds targeting the ATP-binding region of CDK. These CDK inhibitors inhibit proliferation of tumor cells both in vitro and in vivo (see, for example, Non-Patent Document 16). Numerous CDK inhibitors are known to be currently undergoing clinical evaluations.

Aurora kinase inhibitors and cyclin-dependent kinase (CDK) inhibitors both inhibit proliferation of tumor cells in xenograft mouse strains loaded with human tumor cells in human tumor cell lines as well. However, since human cancers are composed of genetically and biologically heterogeneous cells, sensitivity to individual antitumor agents is known to vary for each individual cell. For this reason, in order to develop highly effective antitumor agents, instead of developing Aurora kinase inhibitors and CDK inhibitors separately, it is preferable to develop drugs that simultaneously inhibit a plurality of targets relating to cell proliferation. This is supported by the fact that numerous multi-kinase inhibitors such as sunitinib maleate (SU11248 maleate: including VEGFR-1,2,3, PDGFR, KIT, Flt3 and CSFIR), imanitib mesylate (Gleevec: including Bcr-Abl kinase, C-KIT and PDGFR) and lapanitib (including EGFR and HER2) demonstrate potent clinical effects.

There are currently no antitumor agents that have actually been released commercially in the form of dual Aurora kinase and CDK inhibitors (referred to as "Aurora/CDK dual inhibitors" in the present description). Although the only such inhibitor currently at the pre-clinical trial stage is JNJ-7706621, since it is necessary to administer this drug by consecutive daily subcutaneous injections in order to obtain the maximum effects thereof, it is predicted to encounter difficulties in clinical application in consideration of patient QOL (see, for example, Patent Document 5 and Non-Patent Document 17). Namely, there is currently no practical therapeutic drug for use in preventing or treating cancer that has Aurora/CDK dual inhibitory activity.

In addition, there are numerous drugs that simultaneously inhibit Aurora kinase and CDK known to currently be in the research stage. However, compounds having a pyrazolobenzothiazole backbone have previously not been known as compounds that simultaneously inhibit Aurora kinase and CDK.

Non-Patent Document 1: Ungerer, M. et al., Circulation 1993; 87: 454-463

Non-Patent Document 2: Ungerer, M. et al., Cir. Res. 1994; 74: 206-213

Non-Patent Document 3: White, D. C. et al., Proc. Natl. Acad. Sci. USA 2000; 97: 5428-5433

Non-Patent Document 4: Shah, A. S. et al., Circulation 2001; 103: 1311-1316

Non-Patent Document 5: Rockman, H. A. et al., Proc. Natl. Acad. Sci. USA 1998; 95: 7000-7005

Non-Patent Document 6: Harding, V. B. et al., Proc. Natl. Acad. Sci. USA 2001; 98: 5809-5814

Non-Patent Document 7: Iino, M. et al., J. Med. Chem. 2002; 45: 2150-2159

Non-Patent Document 8: Crane, Richard; Gadea, Bedrick; Littlepage, Laurie; Wu, Hua; Ruderman, Joan V., Biology of the Cell (2004), 96 (3), 215-229

Non-Patent Document 9: Bischoff, J. R., Anderson, L., Zhu, Y. et al., Embo. J. (1998); 17 (11): 3052-3065

Non-Patent Document 10: Fancelli, Daniele; Moll, Juergen, Expert Opinion on Therapeutic Patents (2005), 15 (9), 1169-1182

Non-Patent Document 11: Sanchez, Irma; Dynlacht, Brian David, Seminars in Cell & Developmental Biology (2005), 16 (3), 311-321

Non-Patent Document 12: Saya, Hideyuki; Hirota, Toru, Jikken Igaku (2004), 22 (9), 1237-1241

Non-Patent Document 13: Sherr, C. J., Cell 1994; 79: 551-5

Non-Patent Document 14: Zariwala, Maimoona; Liu, Jidong; Xiong, Yue, Oncogene (1998), 17 (21), 2787-2798

Non-Patent Document 15: Ren, Shengjun; Rollins, Barrett, J. Cell (2004), 117 (2), 239-251

Non-Patent Document 16: Pevarello, Paolo; Villa, Manuela, Expert Opinion on Therapeutic Patents (2005), 15 (6), 675-703

Non-Patent Document 17: Cancer Research 2005; 65 (19), 9038-9046

Patent Document 1: International Publication No. WO 03/20312

Patent Document 2: International Publication No. WO 02/27314

Patent Document 3: International Publication No. WO 02/18350

Patent Document 4: Japanese Laid-open Patent Publication No. 2003-321472

Patent Document 5: International Publication No. WO 02/57240

DISCLOSURE OF THE INVENTION

Problems to be Solved by the Invention

As a result of conducting exploratory research on various compounds to solve these problems, the inventors of the present invention have found that novel α-amino acid derivatives of the following general formula (1) have potent βARK inhibitory activity and are useful in the prevention and treatment of heart failure, thereby leading to completion of the present invention.

Moreover, the inventors of the present invention have found that novel α-amino acid derivatives of the following general formula (1) have Aurora/CDK dual inhibitory activity and are also useful against cell proliferative diseases such as cancer, or in other words, constitute a group of compounds having superior antitumor effects on tumor cells and demonstrating high antitumor effects by oral administration even in animal models, thereby leading to completion of the present invention.

Means for Solving the Problems

Namely, the present invention relates to α-amino acid derivatives of formula (1):

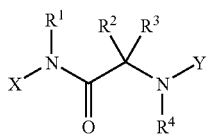
(1)

wherein,

R¹ represents a hydrogen atom,

R² and R³ each independently represent a hydrogen atom; a $C_{1-4}$ alkyl group optionally substituted with a substituent(s) selected from the group consisting of a hydroxyl group, $C_{1-4}$ alkoxy group, benzyloxy group, —$CONH_2$ group and phenyl group; or a phenyl group, or R² and R³ together form —$(CH_2)_n$—, wherein n represents an integer of 2, 3, 4 or 5, or R² and R³ form C=O together with a carbon atom to which they are attached, R⁴ represents a hydrogen atom, or R⁴ and R² together form —$(CH_2)_m$—, wherein m represents an integer of 1, 2, 3 or 4, Y represents a $C_{6-10}$ aryl group or $C_{4-9}$ heterocyclic group optionally substituted with substituents R⁵, R⁶ and R⁷, wherein, the substituents R⁵, R⁶ and R⁷ each independently represent:

a hydrogen atom;

halogen atom;

hydroxyl group;

nitro group;

cyano group;

formyl group;

—$NHCOR^{11}$, wherein, R¹¹ represents a hydrogen atom, $C_{1-4}$ alkyl group, $C_{3-6}$ cycloalkyl group, amino group, $C_{1-4}$ alkylamino group, di-$C_{1-4}$ alkylamino group or $C_{1-4}$ alkoxy group optionally substituted with a hydroxyl group(s);

—$SO_2NH_2$, —$SO_2NHR^{12}$, —$SO_2NR^{12}R^{13}$ or —$NHSO_2R^{12}$, wherein, R¹² and R¹³ each independently represent a $C_{1-4}$ alkyl group;

amino group;

—$CONH_2$;

—$CO_2H$;

$C_{1-4}$ alkylamino group, di-$C_{1-4}$ alkylamino group, $C_{1-4}$ alkylaminocarbonyl group or di-$C_{1-4}$ alkylaminocarbonyl group, wherein, these groups may be optionally substituted with a substituent(s) selected from the group consisting of —$CONH_2$, —$SO_2NH_2$, —$CO_2H$ and a $C_{1-4}$ alkoxycarbonyl group optionally substituted with a hydroxyl group(s);

$C_{3-6}$ cycloalkylaminocarbonyl group;

benzyloxyaminocarbonyl group;

$C_{1-4}$ alkoxyaminocarbonyl group;

N—$C_{1-4}$ alkoxy-$C_{1-4}$ alkylaminocarbonyl group;

$C_{1-4}$ alkyl group, $C_{1-4}$ alkoxy group or $C_{1-4}$ alkoxycarbonyl group, wherein, these groups may be optionally substituted with a substituent(s) selected from the group consisting of a halogen atom, hydroxyl group, —$CONH_2$, —$SO_2NH_2$ and —$CO_2H$; or 5- to 6-membered monocyclic heterocyclic group containing 1 to 3 nitrogen atoms; and X represents a group of formula (2):

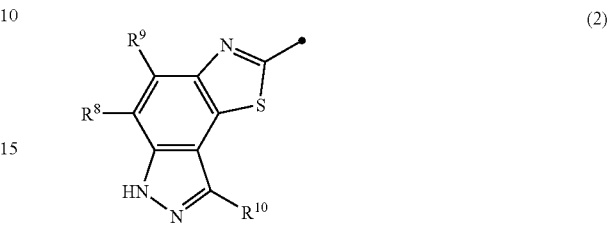
(2)

wherein,

R⁸, R⁹ and R¹⁰ each independently represent:

a hydrogen atom;

halogen atom;

$C_{1-4}$ alkoxycarbonyl group;

—$CO_2H$;

nitro group; or $C_{1-4}$ alkyl group optionally substituted with a substituent(s) selected from the group consisting of a halogen atom, hydroxyl group, $C_{1-4}$ alkoxy group, $C_{1-4}$ alkoxycarbonyl group and —$CO_2H$, or tautomeric group thereof;

or pharmaceutically acceptable salts, prodrugs or solvates thereof.

Effects of the Invention

Compounds of the present invention have potent βARK1 inhibitory activity and can be used as a preventive or therapeutic for heart failure.

Compounds of the present invention have dual Aurora kinase and CDK inhibitory activity, act more effectively against human tumors composed of genetically and biologically heterogeneous cells than inhibition of CDK alone or Aurora kinase alone as known in the prior art, and can be expected to demonstrate tumor reduction effects and recurrence preventive effects.

In addition, since compounds of the present invention have demonstrated effects during oral administration in a xenograft mouse model loaded with a human tumor, patient QOL is considered to be better, easier and more feasible in comparison with JNJ-7706621 during clinical application.

BEST MODE FOR CARRYING OUT THE INVENTION

Figure 1:
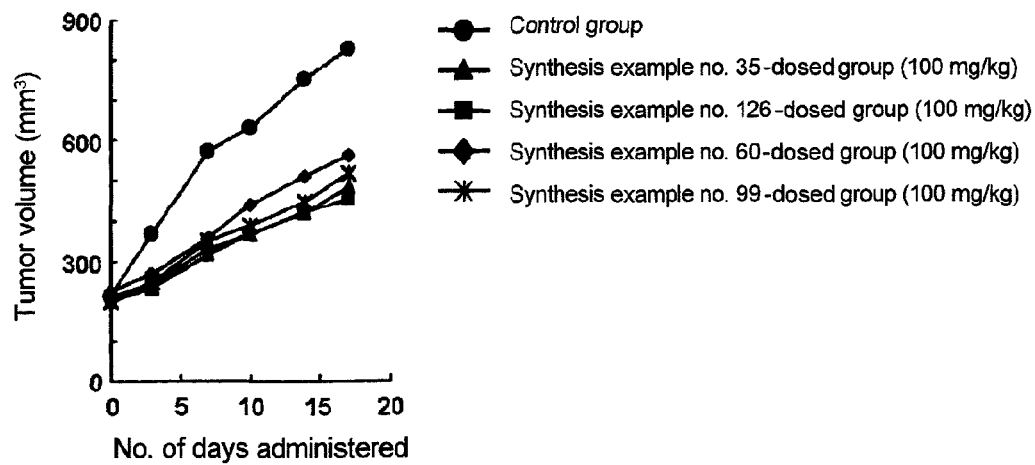
FIG. 1 shows the results of an antitumor test using nude mice transplanted with human prostate cancer cells DU145. The graph shows time-based changes in tumor volume in groups dosed with synthesis example 35 (▲), 60 (♦), 99 (*) and 126 (■) and in a control group (●).

The following provides a detailed explanation of each of the substituents of compounds of formula (1) of the present invention.

Furthermore, in the present description, "ln" stands for normal, "i" for iso, "sec" for secondary, "t" for tertiary, "c" for cyclo, "Me" for methyl, "Et" for ethyl, "Pr" for propyl, "Ac" for acetyl, "En" for benzyl and "Bz" for benzoyl.

A $C_{1-4}$ alkyl group refers to a linear or branched alkyl group having 1 to 4 carbon atoms, examples of which include methyl, ethyl, n-propyl, i-propyl, n-butyl, i-butyl, sec-butyl and t-butyl groups. Preferable examples are methyl, ethyl and t-butyl groups.

A $C_{1-4}$ alkoxy group refers to a group in which an oxygen atom is bonded to a $C_{1-4}$ alkyl group as described above, examples of which include methoxy, ethoxy, n-propoxy, i-propoxy, n-butoxy, i-butoxy, sec-butoxy and t-butoxy groups. Preferable examples are methoxy and ethoxy groups.

A $C_{6-10}$ aryl group refers to an aromatic hydrocarbon group having 6 to 10 carbon atoms, examples of which include phenyl, 1-naphthyl and 2-naphthyl groups. A preferable example is a phenyl group.

A $C_{4-9}$ heterocyclic group refers to a saturated or unsaturated, monocyclic or bicyclic group containing 4 to 9 carbon atoms and 1, 2 or 3 heteroatoms selected from the group consisting of O, N and S, examples of which include a 2-pyridyl group, 3-pyridyl group, 4-pyridyl group, 1-indazolyl group, 3-indazolyl group, 4-indazolyl group, 5-indazolyl group, 6-indazolyl group, 7-indazolyl group, 2-oxo-1-benzimidazolonyl group, 2-oxo-4-benzimidazolonyl group, 2-oxo-5-benzimidazolonyl group, 2-thienyl group and 3-thienyl group. Preferable examples are a 5-indazolyl group and 6-indazolyl group.

A halogen atom refers to a fluorine atom, chlorine atom, bromine atom or iodine atom. Preferable examples are fluorine and chlorine atoms.

A $C_{3-6}$ cycloalkyl group refers to a saturated hydrocarbon group having a cyclic structure and 3 to 6 carbon atoms, examples of which include c-propyl, c-butyl, 2-methyl-c-propyl, c-pentyl, 2-methyl-c-butyl, 3-methyl-c-butyl, 2,2-dimethyl-c-propyl, 2,3-dimethyl-c-propyl, 2-ethyl-c-propyl, c-hexyl, 2-methyl-c-pentyl, 3-methyl-c-pentyl, 2-ethyl-c-butyl, 3-ethyl-c-butyl, 2,2-dimethyl-c-butyl, 2,3-dimethyl-c-butyl, 2,4-dimethyl-c-butyl and 3,3-dimethyl-c-butyl groups. Preferable examples are c-propyl, c-butyl, c-pentyl and c-hexyl groups.

A $C_{1-4}$ alkylamino group refers to an amino group substituted with a $C_{1-4}$ alkyl group as described above, examples of which include methylamino, ethylamino, n-propylamino, i-propylamino, n-butylamino, i-butylamino, sec-butylamino and t-butylamino groups. Preferable examples are methylamino, ethylamino, n-propylamino and i-propylamino groups.

A di-$C_{1-4}$ alkylamino group refers to an amino group substituted with the same or different, two $C_{1-4}$ alkyl groups as described above, examples of which include dimethylamino, diethylamino, di-n-propylamino, di-i-propylamino, di-n-butylamino, di-i-butylamino and N,N-ethylmethylamino groups. Preferable examples are dimethylamino and diethylamino groups.

A $C_{1-4}$ alkylaminocarbonyl group refers to an aminocarbonyl group substituted with a $C_{1-4}$ alkyl group as described above, examples of which include methylaminocarbonyl, ethylaminocarbonyl, n-propylaminocarbonyl, i-propylaminocarbonyl, n-butylaminocarbonyl, i-butylaminocarbonyl, sec-butylaminocarbonyl and t-butylaminocarbonyl groups. Preferable examples include methylaminocarbonyl, ethylaminocarbonyl, n-propylaminocarbonyl and n-butylaminocarbonyl groups.

A di-$C_{1-4}$ alkylaminocarbonyl group refers to an aminocarbonyl group substituted with the same or different, two $C_{1-4}$ alkyl groups as described above, examples of which include dimethylaminocarbonyl, diethylaminocarbonyl, di-n-propylaminocarbonyl, di-i-propylaminocarbonyl, di-n-butylaminocarbonyl, di-i-butylaminocarbonyl and N,N-ethylmethylaminocarbonyl groups. Preferable examples include dimethylaminocarbonyl and diethylaminocarbonyl groups.

A $C_{1-4}$ alkoxycarbonyl group refers to a carbonyl group substituted with a $C_{1-4}$ alkoxy group as described above, examples of which include methoxycarbonyl, ethoxycarbonyl, n-propoxycarbonyl, i-propoxycarbonyl, n-butoxycarbonyl, i-butoxycarbonyl, sec-butoxycarbonyl and t-butoxycarbonyl groups. Preferable examples include methoxycarbonyl and ethoxycarbonyl groups.

A $C_{3-6}$ cycloalkylaminocarbonyl group refers to an aminocarbonyl group substituted with a $C_{1-6}$ cycloalkyl group as described above, examples of which include c-propylaminocarbonyl, c-butylaminocarbonyl, 2-methyl-c-propylaminocarbonyl, c-pentylaminocarbonyl, 2-methyl-c-butylaminocarbonyl, 3-methyl-c-butylaminocarbonyl, 2,2-dimethyl-c-propylaminocarbonyl, 2,3-dimethyl-c-propylaminocarbonyl, 2-ethyl-c-propylaminocarbonyl, c-hexylaminocarbonyl, 2-methyl-c-pentylaminocarbonyl, 3-methyl-c-pentylaminocarbonyl, 2-ethyl-c-butylaminocarbonyl, 3-ethyl-c-butylaminocarbonyl, 2,2-dimethyl-c-butylaminocarbonyl, 2,3-dimethyl-c-butylaminocarbonyl, 2,4-dimethyl-c-butylaminocarbonyl and 3,3-dimethyl-c-butylaminocarbonyl groups. Preferable examples include c-propylaminocarbonyl and c-butylaminocarbonyl groups.

A $C_{1-4}$ alkoxyaminocarbonyl group refers to an aminocarbonyl group substituted with a $C_{1-4}$ alkoxy group as described above, examples of which include methoxyaminocarbonyl, ethoxyaminocarbonyl, n-propoxyaminocarbonyl, i-propoxyaminocarbonyl, n-butoxyaminocarbonyl, i-butoxyaminocarbonyl, sec-butoxyaminocarbonyl and t-butoxyaminocarbonyl groups. Preferable examples include methoxyaminocarbonyl and ethoxyaminocarbonyl groups.

An N—$C_{1-4}$ alkoxy-$C_{1-4}$ alkylaminocarbonyl group refers to an aforementioned $C_{1-4}$ alkylaminocarbonyl group substituted with a $C_{1-4}$ alkoxy group as described above on an N atom thereof, examples of which include N-methoxy-methylaminocarbonyl, N-methoxy-ethylaminocarbonyl, N-ethoxy-methylaminocarbonyl and N-ethoxy-ethylaminocarbonyl groups. Preferable examples include N-methoxy-methylaminocarbonyl and N-methoxy-ethylaminocarbonyl groups.

A 5- to 6-membered monocyclic heterocyclic group containing 1 to 3 nitrogen atoms may be partially or fully saturated and may be modified with an oxo group. Specific examples include a 2-oxo-2,3-dihydro-imidazol-1-yl group, pyrrolidinyl group, imidazolidinyl group, piperazinyl group, piperidyl group, 1-pyrazolyl group, 1-imidazolyl group, 1-triazolyl group, imidazolinyl group, pyridyl group, 2-oxopyridyl group, pyradinyl group and triazinyl group. Preferable example is a 2-oxo-2,3-dihydro-imidazol-1-yl group.

In the present description, in the case "$R^2$ and $R^3$ together form —$(CH_2)_n$—, wherein n represents an integer of 2, 3, 4 or 5", it means that $R^2$ and $R^3$ form a cyclopropane ring, cyclobutane ring, cyclopentane ring or cyclohexane ring, and preferably a cyclopropane ring, together with a carbon atom to which they are attached.

In the present description, in the case "R⁴ and R² together form —(CH₂)$_m$—, wherein m represents an integer of 1, 2, 3 or 4", it means that R⁴ and R² together with atoms to which they are attached form an azilidine ring, azetidine ring, pyrrolidine ring or piperidine ring, and preferably a pyrrolidine ring.

In the present description, "optionally substituted" refers to the case of a substituent in question not being substituted as well as including the case of being substituted by at least one, and preferably 1 to 3, given groups. In the case of two or more types of given groups being present, the substituent in question may be substituted by the same or different given groups. For example, a "C$_{1-4}$ alkyl group optionally substituted with a substituent(s) selected from the group consisting of a hydroxyl group, C$_{1-4}$ alkoxy group, benzyloxy group, —CONH₂ group and phenyl group" refers to an unsubstituted C$_{1-4}$ alkyl group as described above as well as a C$_{1-4}$ alkyl group as described above substituted with at least one, and preferably 1 to 3, the same or different substituents selected from the group consisting of a hydroxyl group, C$_{1-4}$ alkoxy group, benzyloxy group, —CONH₂ and phenyl group.

Thus, the present invention relates to α-amino acid derivatives of formula (1):

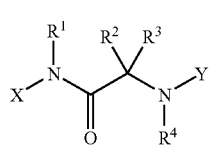

(1)

wherein,

R¹ represents a hydrogen atom,

R² and R³ each independently represent a hydrogen atom; a C$_{1-4}$ alkyl group optionally substituted with a substituent(s) selected from the group consisting of a hydroxyl group, C$_{1-4}$ alkoxy group, benzyloxy group, —CONH₂ group and phenyl group; or phenyl group; or R² and R³ together form —(CH₂)$_n$—, wherein n represents an integer of 2, 3, 4 or 5, or R² and R³ form C═O together with a carbon atom to which they are attached, R⁴ represents a hydrogen atom, or R⁴ and R² together form —(CH₂)$_n$—, wherein m represents an integer of 1, 2, 3 or 4, Y represents a C$_{6-10}$ aryl group or C$_{4-9}$ heterocyclic group optionally substituted with substituents R⁵, R⁶ and R⁷, wherein, the substituents R⁵, R⁶ and R⁷ each independently represent:

a hydrogen atom;

halogen atom;

hydroxyl group;

nitro group;

cyano group;

formyl group;

—NHCOR¹¹, wherein, R¹¹ represents a hydrogen atom, C$_{1-4}$ alkyl group, C$_{3-6}$ cycloalkyl group, amino group, C$_{1-4}$ alkylamino group, di-C$_{1-4}$ alkylamino group or a C$_{1-4}$ alkoxy group optionally substituted with a hydroxyl group(s);

—SO₂NH₂, —SO₂NHR¹², —SO₂NR¹²R¹³ or —NHSO₂R¹², wherein, R¹² and R¹³ each independently represent a C$_{1-4}$ alkyl group;

amino group;

—CONH₂;

—CO₂H;

C$_{1-4}$ alkylamino group, di-C$_{1-4}$ alkylamino group, C$_{1-4}$ alkylaminocarbonyl group or di-C$_{1-4}$ alkylaminocarbonyl group, wherein, these groups may be optionally substituted with a substituent(s) selected from the group consisting of —CONH₂, —SO₂NH₂, —CO₂H and a C$_{1-4}$ alkoxycarbonyl group optionally substituted with a hydroxyl group(s);

C$_{3-6}$ cycloalkylaminocarbonyl group;

benzyloxyaminocarbonyl group;

C$_{1-4}$ alkoxyaminocarbonyl group;

N—C$_{1-4}$ alkoxy-C$_{1-4}$ alkylaminocarbonyl group;

C$_{1-4}$ alkyl group, C$_{1-4}$ alkoxy group or C$_{1-4}$ alkoxycarbonyl group, wherein, these groups may be optionally substituted with a substituent(s) selected from the group consisting of a halogen atom, hydroxyl group, —CONH₂, —SO₂NH₂ and —CO₂H; or 5- to 6-membered monocyclic heterocyclic group containing 1 to 3 nitrogen atoms; and, X represents a group of formula (2):

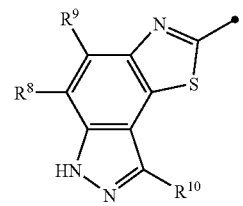

(2)

wherein,

R¹, R⁹ and R¹⁰ each independently represent:

a hydrogen atom;

halogen atom;

C$_{1-4}$ alkoxycarbonyl group;

—CO₂H;

nitro group; or

C$_{1-4}$ alkyl group optionally substituted with a substituent(s) selected from the group consisting of a halogen atom, hydroxyl group, C$_{1-4}$ alkoxy group, C$_{1-4}$ alkoxycarbonyl group and —CO₂H, or tautomeric group thereof;

or pharmaceutically acceptable salts, prodrugs or solvates thereof.

A compound of formula (1) is preferably selected from that in which either one of R² or R³ is a hydrogen atom, and the other is a C$_{1-4}$ alkyl group optionally substituted with a substituent(s) selected from the group consisting of a hydroxyl group, C$_{1-4}$ alkoxy group, benzyloxy group, —CONH₂ and phenyl group, or a phenyl group, R² and R³ both represent hydrogen atoms or both represent C$_{1-4}$ alkyl groups, or R² and R³ together form —(CH₂)$_n$—, wherein n represents an integer of 2, 3, 4 or 5.

More preferably, a compound of formula (1) is selected from that in which R² and R³ both represent hydrogen atoms; both represent methyl groups; or R² and R³ form cyclopropane together with a carbon atom to which they are attached.

A compound of formula (1), in which Y represents a phenyl group optionally substituted with R⁵, R⁶ and R⁷, wherein R⁵, R⁶ and R⁷ are as defined above, is also preferable.

Among such compounds, compounds of formula (3):

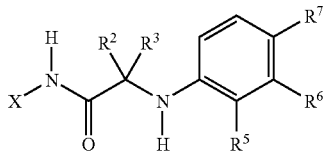

(3)

(wherein, $R^2$, $R^3$, $R^5$, $R^6$, $R^7$ and X are as defined above) are preferable.

In particular, a compound of formula (1) is preferable in which at least one of $R^5$, $R^6$ and $R^7$ is a hydrogen atom, while the remaining two each independently represent a halogen atom; hydroxyl group; —NHCOR$^{11}$, wherein $R^{11}$ refers to a $C_{1-4}$ alkyl group, $C_{3-6}$ cycloalkyl group, $C_{1-4}$ alkylamino group or a $C_{1-4}$ alkoxy group optionally substituted with a hydroxyl group(s); —SO$_2$NH$_2$, —NHSO$_2$R$^{12}$, wherein $R^{12}$ refers to a $C_{1-4}$ alkyl group; —CONH$_2$; $C_{1-4}$ alkylaminocarbonyl group, di-$C_{1-4}$ alkylaminocarbonyl group, wherein the $C_{1-4}$ alkylaminocarbonyl group or di-$C_{1-4}$ alkylaminocarbonyl group may be optionally substituted with a substituent(s) selected from the group consisting of —CONH$_2$, —SO$_2$NH$_2$, —CO$_2$H and —CO$_2$ (CH$_2$)$_p$OH, wherein p refers to an integer of 1, 2 or 3; $C_{3-6}$ cycloalkylaminocarbonyl group; benzyloxyaminocarbonyl group; $C_{1-4}$ alkoxyaminocarbonyl group; or $C_{1-4}$ alkyl group, $C_{1-4}$ alkoxy group or $C_{1-4}$ alkoxycarbonyl group, wherein the $C_{1-4}$ alkyl group, $C_{1-4}$ alkoxy group or $C_{1-4}$ alkoxycarbonyl group may be optionally substituted with a substituent(s) selected from the group consisting of a halogen atom, hydroxyl group, —CONH$_2$, —SO$_2$NH$_2$ and —COOH.

In addition, preferred compounds resulting from a specific combination of each substituent are those of formula (1):

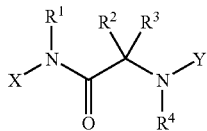

(1)

wherein, $R^1$ is a hydrogen atom;

$R^2$ and $R^3$ each independently represent:

a hydrogen atom, methyl group, ethyl group, n-propyl group, i-propyl group, n-butyl group, i-butyl group, s-butyl group, t-butyl group, hydroxymethyl group, 2-hydroxyethyl group, 1-hydroxyethyl group, methoxymethyl group, 2-methoxyethyl group, 1-methoxyethyl group, benzyloxymethyl group, benzyloxyethyl group, carbamoylmethyl group, 2-carbamoylethyl group, benzyl group or phenyl group, or $R^2$ and $R^3$ form a cyclopropane ring, cyclobutane ring, cyclopentane ring or cyclohexane ring together with a carbon atom to which they are attached, or $R^2$ and $R^3$ form an oxo (C=O) group together with a carbon atom to which they are attached.

More preferred compounds of the above formula (1) are those wherein $R^2$ and $R^3$ each independently represent a hydrogen atom, methyl group, i-butyl group, hydroxymethyl group, 2-hydroxyethyl group, carbamoylmethyl group or phenyl group, or $R^2$ and $R^3$ form a cyclopropane ring, cyclobutane ring, cyclopentane ring or cyclohexane ring together with a carbon atom to which they are attached.

Even more preferred compounds of the above formula (1) are those wherein $R^2$ and $R^3$ both represent hydrogen atoms or methyl groups, either one of $R^2$ and $R^3$ represents a hydrogen atom, and the other represents a methyl group, hydroxymethyl group, carbamoylmethyl group or phenyl group, or $R^2$ and $R^3$ form a cyclopropane ring together with a carbon atom to which they are attached.

Preferred compounds of the above formula (1) are those in which $R^4$ is a hydrogen atom or $R^2$ and $R^4$ form an azilidine ring, azetidine ring, pyrrolidine ring or piperidine ring, and preferably a pyrrolidine ring, together with atoms to which they are attached. More preferred compounds of the above formula (1) are those in which $R^4$ is a hydrogen atom.

In addition, compounds of the above formula (1) in which Y is represented by formula (3'):

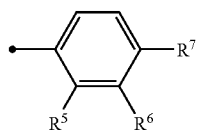

(3')

wherein, $R^5$, $R^6$ and $R^7$ are each independently as defined above, are preferable.

In one embodiment of the present invention relating to the case of Y being represented by formula (3'), $R^5$, $R^6$ and $R^7$ are each independently a group selected from the group consisting of:

a hydrogen atom; fluorine atom, chlorine atom, bromine atom or iodine atom; hydroxyl group; nitro group; acetylamino group, propionylamino group, pivaloylamino group, cyclopropylcarbonylamino group, —NHCONHMe, methoxycarbonylamino group, ethoxycarbonylamino group, t-butoxycarbonylamino group or —NHCO$_2$ (CH$_2$)$_k$OH; —SO$_2$NH$_2$, —SO$_2$NHMe or —NHSO$_2$Me; amino group; carbamoyl group; carboxyl group; methylamino group, dimethylamino group, ethylamino group, diethylamino group, ethylmethylamino group, methylcarbamoyl group, ethylcarbamoyl group, ethylmethylcarbamoyl group, dimethylcarbamoyl group, diethylcarbamoyl group, i-propylcarbamoyl group, —CONH(CH$_2$)$_k$CONH$_2$, —CONH(CH$_2$)$_k$SO$_2$NH$_2$, —CONH(CH$_2$)$_k$COOH or —CONHCH$_2$COO(CH$_2$)$_k$OH; cyclopropylcarbamoyl group; benzyloxyaminocarbonyl group; methoxyaminocarbonyl group or ethoxyaminocarbonyl group; —CON(Me)OMe; methyl group, ethyl group, n-propyl group, i-propyl group, n-butyl group, sec-butyl group, i-butyl group, t-butyl group, trifluoromethyl group, hydroxymethyl group, methoxy group, ethoxy group, n-propoxy group, i-propoxy group, n-butoxy group, sec-butoxy group, i-butoxy group, t-butoxy group, trifluoromethoxy group, —OCH$_2$CH(OH)CH$_2$OH, —O(CH$_2$)$_k$SO$_2$NH$_2$, —O(CH$_2$)$_k$CONH$_2$, —O(CH$_2$)$_k$COOH, —COOMe, —COOEt, —COO(n-Pr) or —COO(i-Pr); and 2-oxo-1-imidazolyl group (wherein each of the above descriptions, k represents an integer of 1, 2, 3 or 4).

In addition, X is represented by formula (2):

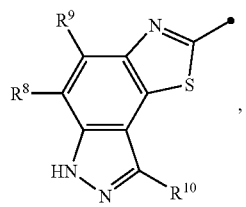

(2)

in an embodiment of the present invention relating to formula (2), in which $R^8$, $R^9$ and $R^{10}$ are each independently:

a hydrogen atom, fluorine atom, chlorine atom, bromine atom, iodine atom, methyl group, ethyl group, n-propyl group, i-propyl group, trifluoromethyl group, nitro group, methoxycarbonyl group or ethoxycarbonyl group, more preferably $R^8$ and $R^{10}$ are hydrogen atoms, while $R^9$ is a hydrogen atom, methyl group, trifluoromethyl group, nitro group or methoxycarbonyl group, and even more preferably, $R^8$ and $R^{10}$ are hydrogen atoms, while $R^9$ is a hydrogen atom or trifluoromethyl group.

In addition, X represented by formula (2) can be tautomerized as indicated below, and tautomeric groups are included in the present invention.

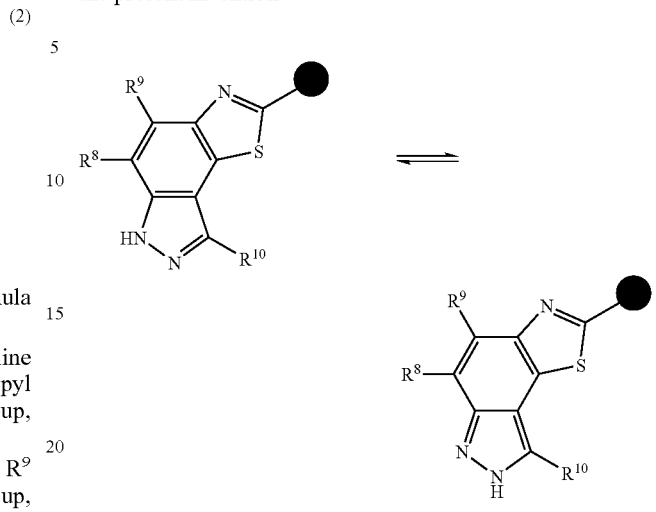

The following lists preferable specific compounds provided by the present invention.

TABLE 1

| NO. | R1 | R2 | R3 | R4 | Y | R8 | R9 | R10 |
|---|---|---|---|---|---|---|---|---|
| 1 | H | H | H | H | 3-methoxyphenyl (O—CH₃) | H | H | H |
| 2 | H | H | H | H | 3-hydroxyphenyl (OH) | H | H | H |
| 3 | H | H | H | H | 3-fluorophenyl (F) | H | H | H |
| 4 | H | H | H | H | 3-methoxy-4-chlorophenyl (O—CH₃, Cl) | H | H | H |
| 5 | H | H | H | H | 3,5-difluorophenyl (F, F) | H | H | H |
| 6 | H | H | H | H | 2-chloro-hydroxyphenyl (OH, Cl) | H | H | H |

TABLE 1-continued
| NO. | R1 | R2 | R3 | R4 | Y | R8 | R9 | R10 |
|---|---|---|---|---|---|---|---|---|
| 7 | H | H | H | H | 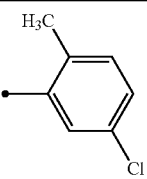 | H | H | H |
| 8 | H | H | H | H | 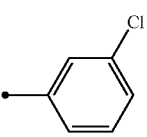 | H | H | H |
| 9 | H | H | H | H | 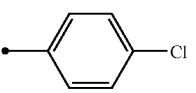 | H | H | H |
| 10 | H | H | H | H | 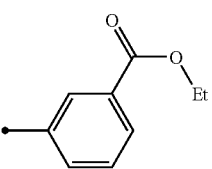 | H | H | H |
| 11 | H | H | H | H | 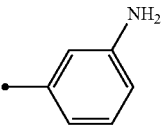 | H | H | H |
| 12 | H | H | H | H | 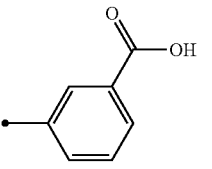 | H | H | H |
| 13 | H | H | H | H | 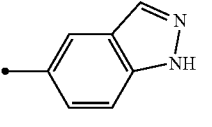 | H | H | H |
| 14 | H | H | H | H | 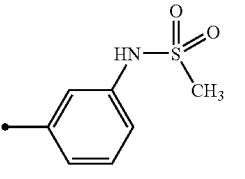 | H | H | H |
| 15 | H | H | H | H | 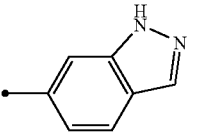 | H | H | H |
| 16 | H | H | H | H | 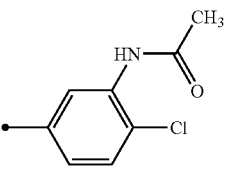 | H | H | H |

TABLE 1-continued
| NO. | R1 | R2 | R3 | R4 | Y | R8 | R9 | R10 |
|---|---|---|---|---|---|---|---|---|
| 17 | H | H | H | H | 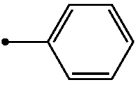 | H |  NO₂ | H |
| 18 | H | H | H | H | 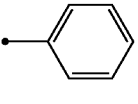 | H | CF₃ | H |
| 19 | H | H | H | H |  | H | CH₃ | H |
| 20 | H | H | H | H | 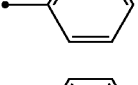 | H | F | H |
| 21 | H | H | H | H |  | H | 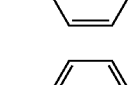 —C(O)OCH₃ | H |
| 22 | H | CH₃ | H | H | 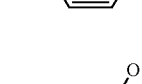 3-OCH₃-phenyl | H | H | H |
| 23 | H | CH₃ | H | H | 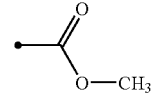 3-OH-phenyl | H | H | H |
| 24 | H | CH₃ | H | H | 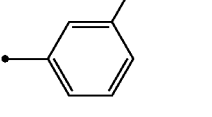 4-Cl-phenyl | H | H | H |
| 25 | H | i-Bu | H | H | 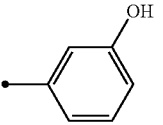 3-OH-phenyl | H | H | H |
| 26 | H | i-Bu | H | H | 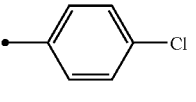 3-OCH₃-phenyl | H | H | H |
| 27 | H | Ph | H | H | 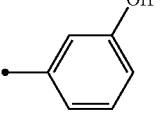 3-OH-phenyl | H | H | H |
| 28 | H | Ph | H | H | 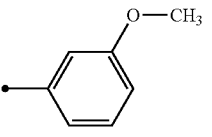 2-Cl-5-(CO₂Et)-phenyl | H | CF₃ | H |

TABLE 1-continued
| NO. | R1 | R2 | R3 | R4 | Y | R8 | R9 | R10 |
|---|---|---|---|---|---|---|---|---|
| 29 | H | Ph | H | H | 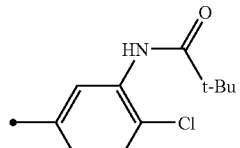 | H | CF$_3$ | H |
| 30 | H | Ph | H | H | 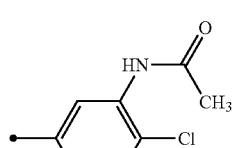 | H | CF$_3$ | H |
| 31 | H | Ph | H | H | 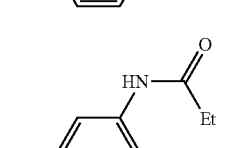 | H | CF$_3$ | H |
| 32 | H | Ph | H | H | 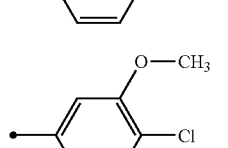 | H | H | H |
| 33 | H | CH$_3$ | CH$_3$ | H | 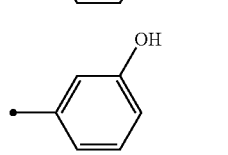 | H | H | H |
| 34 | H | CH$_3$ | CH$_3$ | H | 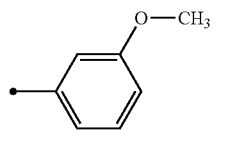 | H | H | H |
| 35 | H | CH$_3$ | CH$_3$ | H | 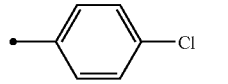 | H | H | H |
| 36 | H | CH$_3$ | CH$_3$ | H | 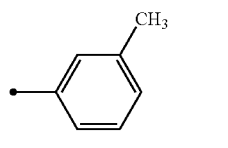 | H | H | H |
| 37 | H | CH$_3$ | CH$_3$ | H | 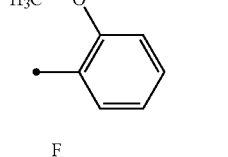 | H | H | H |
| 38 | H | CH$_3$ | CH$_3$ | H | 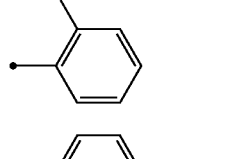 | H | H | H |
| 39 | H | CH$_3$ | CH$_3$ | H | 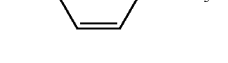 | H | H | H |

TABLE 1-continued
| NO. | R1 | R2 | R3 | R4 | Y | R8 | R9 | R10 |
|---|---|---|---|---|---|---|---|---|
| 40 | H | CH₃ | CH₃ | H | 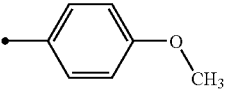 | H | H | H |
| 41 | H | CH₃ | CH₃ | H | 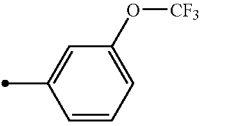 | H | H | H |
| 42 | H | CH₃ | CH₃ | H | 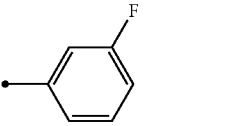 | H | H | H |
| 43 | H | CH₃ | CH₃ | H | 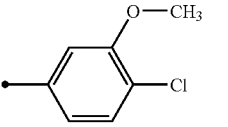 | H | H | H |
| 44 | H | CH₃ | CH₃ | H | 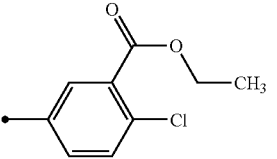 | H | H | H |
| 45 | H | CH₃ | CH₃ | H | 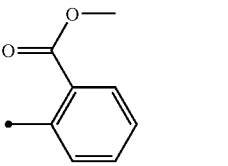 | H | H | H |
| 46 | H | CH₃ | CH₃ | H | 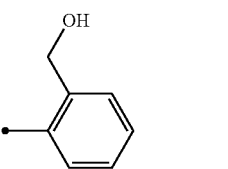 | H | H | H |
| 47 | H | CH₃ | CH₃ | H | 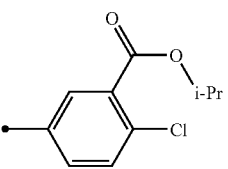 | H | H | H |
| 48 | H | CH₃ | CH₃ | H | 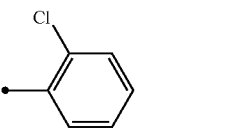 | H | H | H |
| 49 | H | CH₃ | CH₃ | H | 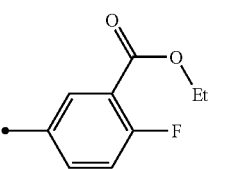 | H | H | H |

TABLE 1-continued
| NO. | R1 | R2 | R3 | R4 | Y | R8 | R9 | R10 |
|---|---|---|---|---|---|---|---|---|
| 50 | H | CH₃ | CH₃ | H | 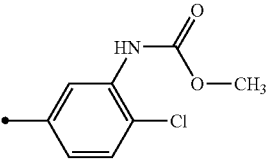 | H | H | H |
| 51 | H | CH₃ | CH₃ | H | 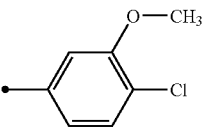 | H | CF₃ | H |
| 52 | H | CH₃ | CH₃ | H | 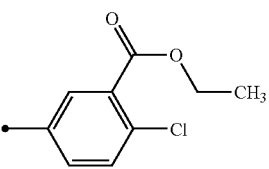 | H | CF₃ | H |
| 53 | H | CH₃ | CH₃ | H | 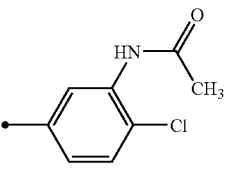 | H | CF₃ | H |
| 54 | H | CH₃ | CH₃ | H | 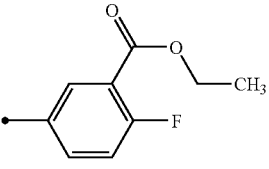 | H | CF₃ | H |
| 55 | H | CH₃ | CH₃ | H | 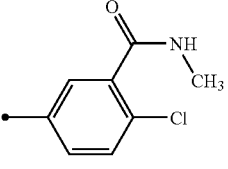 | H | CF₃ | H |
| 56 | H | CH₃ | CH₃ | H | 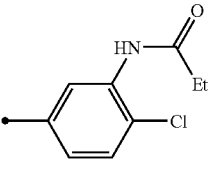 | H | CF₃ | H |
| 57 | H | CH₃ | CH₃ | H | 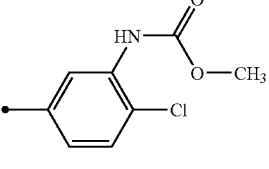 | H | CF₃ | H |
| 58 | H | CH₃ | CH₃ | H | 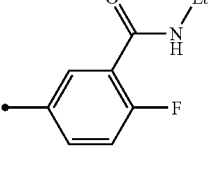 | H | CF₃ | H |

TABLE 1-continued
| NO. | R1 | R2 | R3 | R4 | Y | R8 | R9 | R10 |
|---|---|---|---|---|---|---|---|---|
| 59 | H | CH₃ | CH₃ | H |  | H | CF₃ | H |
| 60 | H | CH₃ | CH₃ | H | 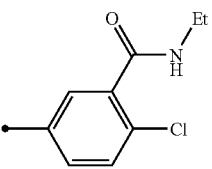 | H | CF₃ | H |
| 61 | H | CH₃ | CH₃ | H | 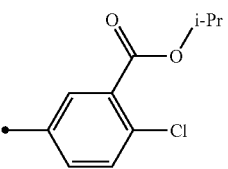 | H | CF₃ | H |
| 62 | H | CH₃ | CH₃ | H | 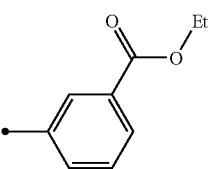 | H | CF₃ | H |
| 63 | H | CH₃ | CH₃ | H | 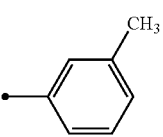 | H | CF₃ | H |
| 64 | H | CH₃ | CH₃ | H | 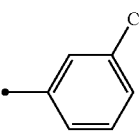 | H | CF₃ | H |
| 65 | H | CH₃ | CH₃ | H | 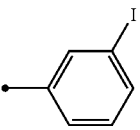 | H | CF₃ | H |
| 66 | H | CH₃ | CH₃ | H | 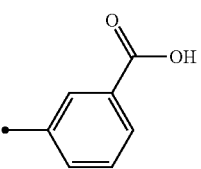 | H | CF₃ | H |
| 67 | H | CH₃ | CH₃ | H | 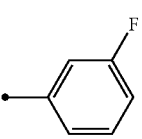 | H | CF₃ | H |
| 68 | H | CH₃ | CH₃ | H | 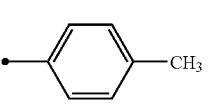 | H | CF₃ | H |

TABLE 1-continued
| NO. | R1 | R2 | R3 | R4 | Y | R8 | R9 | R10 |
|---|---|---|---|---|---|---|---|---|
| 69 | H | CH₃ | CH₃ | H | 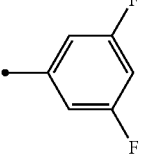 | H | CF₃ | H |
| 70 | H | CH₃ | CH₃ | H | 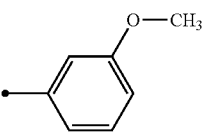 | H | CF₃ | H |
| 71 | H | CH₃ | CH₃ | H | 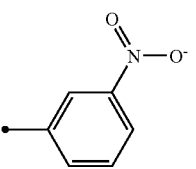 | H | CF₃ | H |
| 72 | H | CH₃ | CH₃ | H | 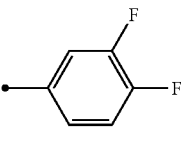 | H | CF₃ | H |
| 73 | H | CH₃ | CH₃ | H | 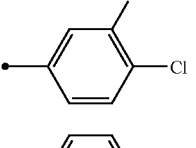 | H | CF₃ | H |
| 74 | H | CH₃ | CH₃ | H | 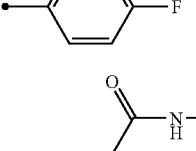 | H | CF₃ | H |
| 75 | H | CH₃ | CH₃ | H | 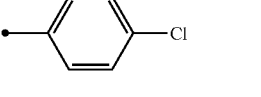 | H | CF₃ | H |
| 76 | H | CH₃ | CH₃ | H | 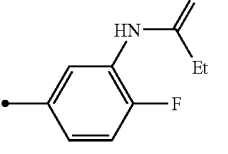 | H | CF₃ | H |
| 77 | H | CH₃ | CH₃ | H | 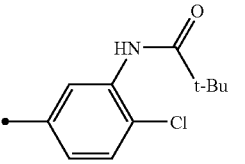 | H | CF₃ | H |
| 78 | H | CH₃ | CH₃ | H | 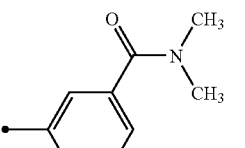 | H | CF₃ | H |

TABLE 1-continued

| NO. | R1 | R2 | R3 | R4 | Y | R8 | R9 | R10 |
|-----|----|----|----|----|---|----|----|----|
| 79 | H | CH₃ | CH₃ | H | 3-(methylsulfonylamino)phenyl | H | CF₃ | H |
| 80 | H | CH₃ | CH₃ | H | 2-chloro-5-(cyclopropanecarboxamido)phenyl | H | CF₃ | H |
| 81 | H | CH₃ | CH₃ | H | 5-acetamido-2-fluorophenyl | H | CF₃ | H |
| 82 | H | CH₃ | CH₃ | H | 3-sulfamoylphenyl | H | CF₃ | H |
| 83 | H | CH₃ | CH₃ | H | 2-oxo-2,3-dihydro-1H-benzo[d]imidazol-5-yl | H | CF₃ | H |
| 84 | H | CH₃ | CH₃ | H | 2-chloro-5-(methylsulfonylamino)phenyl | H | CF₃ | H |
| 85 | H | CH₃ | CH₃ | H | 2-chloro-5-(2-amino-2-oxoethylcarbamoyl)phenyl | H | CF₃ | H |
| 86 | H | CH₃ | CH₃ | H | 3-((2-hydroxyethoxycarbonyl)methylcarbamoyl)phenyl | H | CF₃ | H |

TABLE 1-continued

| NO. | R1 | R2 | R3 | R4 | Y | R8 | R9 | R10 |
|---|---|---|---|---|---|---|---|---|
| 87 | H | CH₃ | CH₃ | H | 2-yl-5-chlorophenyl-C(O)NH-CH₂CH₂-C(O)NH₂ | H | CF₃ | H |
| 88 | H | CH₃ | CH₃ | H | 2-yl-5-chlorophenyl-C(O)NH-CH₂-C(O)NH₂ | H | CF₃ | H |
| 89 | H | CH₃ | CH₃ | H | 5-yl-2-chlorophenyl-NH-C(O)O-CH₂CH₂-OH | H | CF₃ | H |
| 90 | H | CH₃ | CH₃ | H | 5-yl-2-chlorophenyl-NH-C(O)-NH-CH₃ | H | CF₃ | H |
| 91 | H | CH₃ | CH₃ | H | 5-yl-2-chlorophenyl-O-CH₂CH₂CH₂-C(O)NH₂ | H | CF₃ | H |
| 92 | H | CH₃ | CH₃ | H | 2-yl-5-chlorophenyl-O-CH₂CH₂CH₂-C(O)NH₂ | H | CF₃ | H |
| 93 | H | CH₃ | CH₃ | H | 2-yl-5-chlorophenyl-O-CH₂CH₂-S(O)₂NH₂ | H | CF₃ | H |
| 94 | H | CH₃ | CH₃ | H | 5-yl-2-chlorophenyl-O-CH₂CH₂CH₂-S(O)₂NH₂ | H | CF₃ | H |

TABLE 1-continued
| NO. | R1 | R2 | R3 | R4 | Y | R8 | R9 | R10 |
|---|---|---|---|---|---|---|---|---|
| 95 | H | CH₃ | CH₃ | H | 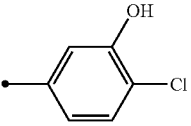 | H | CF₃ | H |
| 96 | H | CH₃ | CH₃ | H | 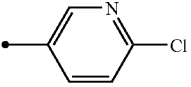 | H | CF₃ | H |
| 97 | H | CH₃ | CH₃ | H | 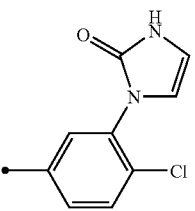 | H | CF₃ | H |
| 98 | H | CH₃ | CH₃ | H | 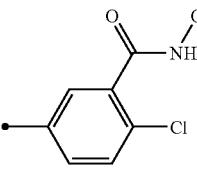 | H | CF₃ | H |
| 99 | H | CH₃ | CH₃ | H | 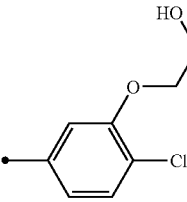 | H | CF₃ | H |
| 100 | H | CH₃ | CH₃ | H | 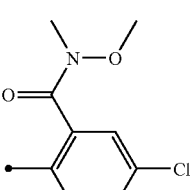 | H | CF₃ | H |
| 101 | H | CH₃ | CH₃ | H | 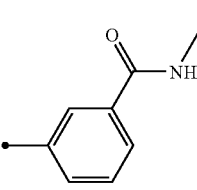 | H | CF₃ | H |
| 102 | H | CH₃ | CH₃ | H | 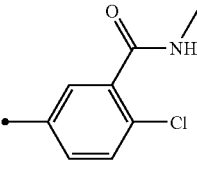 | H | CF₃ | H |
| 103 | H |  | H | H | 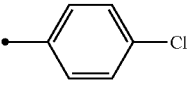 | H | H | H |

TABLE 1-continued

| NO. | R1 | R2 | R3 | R4 | Y | R8 | R9 | R10 |
|-----|----|----|----|----|---|----|----|-----|
| 104 | H | H | H | H | phenyl | H | H | H |
| 105 | H | H | H | H | 4-F-phenyl | H | H | H |
| 106 | H | H | H | H | 3-(NHC(O)CH₃)-phenyl | H | H | H |
| 107 | H | H | H | H | 3,4-dichlorophenyl | H | H | H |
| 108 | H | H | H | H | phenyl | H | H | Cl |
| 109 | H | -CH₂C(O)NH₂ | H | H | 3-OH-phenyl | H | H | H |
| 110 | H | -CH₂C(O)NH₂ | H | H | 3-OCH₃-phenyl | H | H | H |
| 111 | H | — | H | R2, R4 and nitrogen atom bonded to R4 together form pyrrolidine ring | 4-Cl-phenyl | H | H | H |
| 112 | H | -CH₂CH₂OCH₃ | H | H | 4-Cl-phenyl | H | H | H |
| 113 | H | -CH₂CH₂OH | H | H | 4-Cl-phenyl | H | H | H |
| 114 | H | R2 and R3 together form cyclobutane ring | | H | 4-Cl-phenyl | H | H | H |

TABLE 1-continued

| NO. | R1 | R2 | R3 | R4 | Y | R8 | R9 | R10 |
|---|---|---|---|---|---|---|---|---|
| 115 | H | 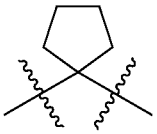 R2 and R3 together form cyclopentane ring | | H |  | H | H | H |
| 116 | H | 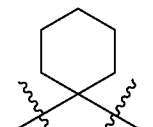 R2 and R3 together form cyclohexane ring | | H |  | H | H | H |
| 117 | H | 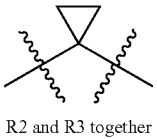 R2 and R3 together form cyclopropane ring | | H |  | H | H | H |
| 118 | H | 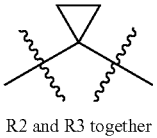 R2 and R3 together form cyclopropane ring | | H | 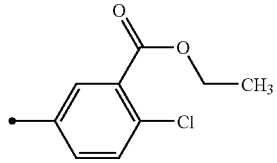 | H | H | H |
| 119 | H | 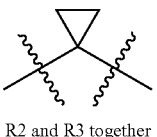 R2 and R3 together form cyclopropane ring | | H | 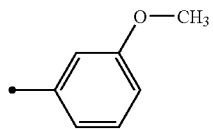 | H | H | H |
| 120 | H | 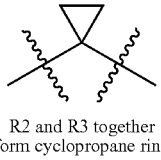 R2 and R3 together form cyclopropane ring | | H | 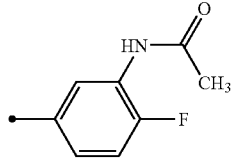 | H | H | H |
| 121 | H | 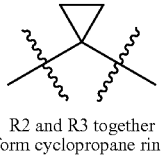 R2 and R3 together form cyclopropane ring | | H | 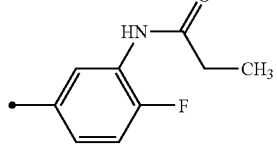 | H | H | H |
| 122 | H | 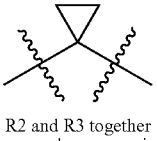 R2 and R3 together form cyclopropane ring | | H | 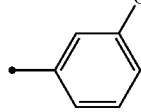 | H | H | H |

TABLE 1-continued
| NO. | R1 | R2 | R3 | R4 | Y | R8 | R9 | R10 |
|---|---|---|---|---|---|---|---|---|
| 123 | H | 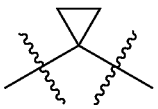 R2 and R3 together form cyclopropane ring | | H | 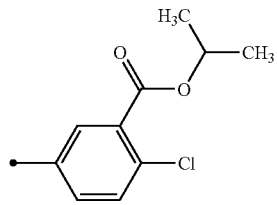 | H | H | H |
| 124 | H | 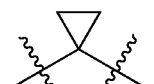 R2 and R3 together form cyclopropane ring | | H | 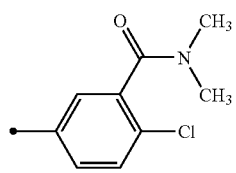 | H | H | H |
| 125 | H | 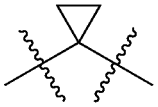 R2 and R3 together form cyclopropane ring | | H | 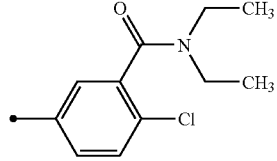 | H | H | H |
| 126 | H | 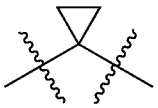 R2 and R3 together form cyclopropane ring | | H | 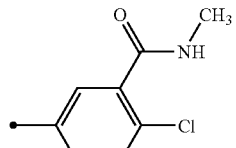 | H | H | H |
| 127 | H | 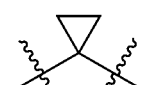 R2 and R3 together form cyclopropane ring | | H | 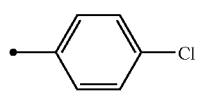 | H | CH$_3$ | H |
| 128 | H | CH$_3$ | CH$_3$ | H | 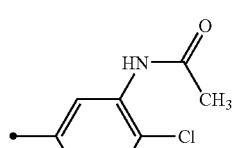 | H | H | H |
| 129 | H | CH$_3$ | CH$_3$ | H | 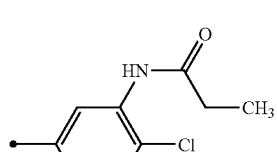 | H | H | H |
| 130 | H | CH$_3$ | CH$_3$ | H | 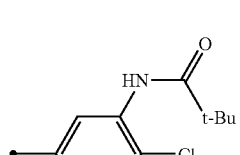 | H | H | H |

TABLE 1-continued
| NO. | R1 | R2 | R3 | R4 | Y | R8 | R9 | R10 |
|---|---|---|---|---|---|---|---|---|
| 131 | H | Ph | H | H | 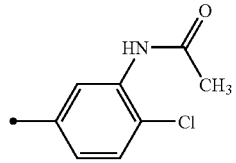 | H | H | H |
| 132 | H |  | H | H |  | H | H | H |
| 133 | H | R2 and R3 together from oxo (C=O) | | H | 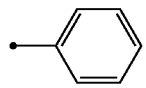 | H | H | H |
| 134 | H | H | H | H | 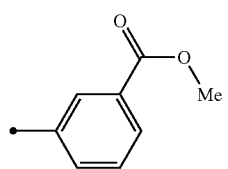 | H | H | H |
| 135 | H | CH₃ | CH₃ | H | 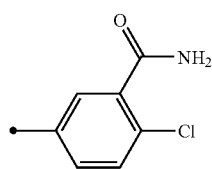 | H | CF₃ | H |
| 136 | H | CH₃ | CH₃ | H | 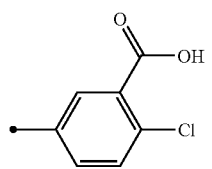 | H | CF₃ | H |
| 137 | H | CH₃ | CH₃ | H | 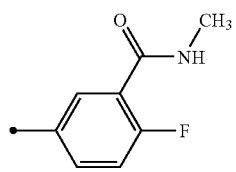 | H | CF₃ | H |
| 138 | H | CH₃ | CH₃ | H | 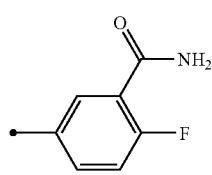 | H | CF₃ | H |
| 139 | H | CH₃ | CH₃ | H | 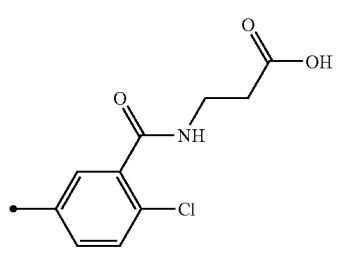 | H | CF₃ | H |

TABLE 1-continued
| NO. | R1 | R2 | R3 | R4 | Y | R8 | R9 | R10 |
|---|---|---|---|---|---|---|---|---|
| 140 | H | CH₃ | CH₃ | H | 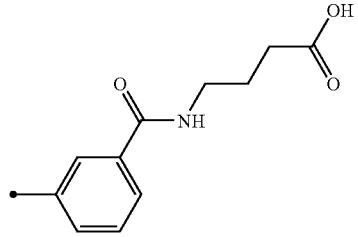 | H | CF₃ | H |
| 141 | H | CH₃ | CH₃ | H | 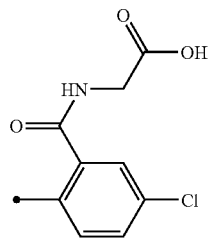 | H | CF₃ | H |
| 142 | H | CH₃ | CH₃ | H | 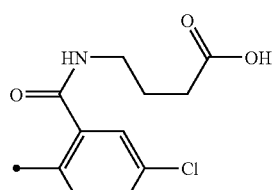 | H | CF₃ | H |
| 143 | H | CH₃ | CH₃ | H | 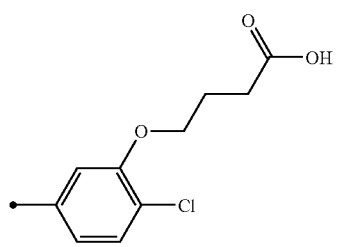 | H | CF₃ | H |
| 144 | H | CH₃ | CH₃ | H | 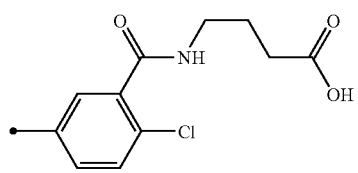 | H | CF₃ | H |
| 145 | H | CH₃ | CH₃ | H | 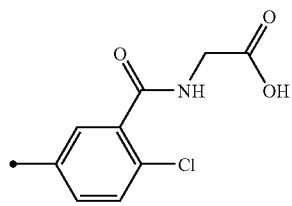 | H | CF₃ | H |

Although the following indicates specific examples of particularly preferable compounds able to be used in the present invention, the present invention is not limited thereto.

2-(4-chloro-3-hydroxyphenylamino)-N-(6H-pyrazolo[4',3': 3,4]benzo[1,2-d]thiazol-2-yl)-acetamide, 2-(3-hydroxyphenylamino)-2-methyl-N-(6H-pyrazolo[4',3': 3,4]benzo[1,2-d]thiazol-2-yl)-propionamide, 2-(4-chlorophenylamino)-3-hydroxy-N-(6H-pyrazolo[4',3': 3,4]benzo[1,2-d]thiazol-2-yl)-propionamide, 2-(4-chlorophenylamino)-2-methyl-N-(6H-pyrazolo[4',3':3, 4]benzo[1,2-d]thiazol-2-yl)-propionamide, 2-(4-chlorophenylamino)-N-(6H-pyrazolo[4',3':3,4]benzo [1,2-d]thiazol-2-yl)-propionamide, 2-(3-acetylamino-4-chlorophenylamino)-N-(6H-pyrazolo [4',3':3,4]benzo[1,2-d]thiazol-2-yl)-acetamide, 1-(4-chlorophenylamino)-N-(6H-pyrazolo[4',3':3,4]benzo [1,2-d]thiazol-2-yl)-cyclopropanecarboxamide, 2-chloro-5-[1-(6H-pyrazolo[4',3':3,4]benzo[1,2-d]thiazol-2-ylcarbamoyl)-cyclopropylamino]-benzoic acid ethyl ester, 2-(3-acetylamino-4-chlorophenylamino)-2-methyl-N-(6H-pyrazolo[4',3':3,4]benzo[1,2-d]thiazol-2-yl)-propionamide, 1-(3-acetylamino-4-fluorophenylamino)-N-(6H-pyrazolo [4',3':3,4]benzo[1,2-d]thiazol-2-yl)-cyclopropane carboxamide, 1-(4-fluoro-3-propionylamino-phenylamino)-N-(6H-pyrazolo[4',3':3,4]benzo[1,2-d]thiazol-2-yl)cyclopropane-carboxamide, 2-(4-chloro-3-propionylamino-phenylamino)-2-methyl-N-(6H-pyrazolo[4',3':3,4]benzo[1,2-d]thiazol-2-yl)-propionamide, 2-(3-acetylamino-4-chlorophenylamino)-2-methyl-N-(4-trifluoromethyl-(6H-pyrazolo[4',3':3,4]benzo[1,2-d]thiazol-2-yl)-propionamide, 2-chloro-N-methyl-5-[1-(6H-pyrazolo[4',3':3,4]benzo[1,2-d]thiazol-2-ylcarbamoyl)-cyclopropylamino]-benzamide, 2-chloro-N-methyl-5-[1-methyl-1-(4-trifluoromethyl)-6H-pyrazolo[4',3':3,4]benzo[1,2-d]thiazol-2-ylcarbamoyl-ethylamino]-benzamide, 2-(4-chloro-3-propionylamino-phenylamino)-2-methyl-N-(4-trifluoromethyl)-6H-pyrazolo[4',3':3,4]benzo[1,2-d] thiazol-2-yl)-propionamide, 2-chloro-5-[1-methyl-1-(4-trifluoromethyl-6H-pyrazolo[4', 3':3,4]benzo[1,2-d]thiazol-2-ylcarbamoyl)-ethylamino]-benzamide, 1-(4-chlorophenylamino)-N-(4-methyl-6H-pyrazolo[4',3':3, 4]benzo[1,2-d]thiazol-2-yl)-cyclopropanecarboxamide, N-ethyl-2-fluoro-5-[1-methyl-1-(4-trifluoromethyl)-6H-pyrazolo[4',3':3,4]benzo[1,2-d]thiazol-2-ylcarbamoyl)-ethylamino]-benzamide, 2-chloro-N-ethyl-5-[1-methyl-1-(4-trifluoromethyl)-6H-pyrazolo[4',3':3,4]benzo[1,2-d]thiazol-2-ylcarbamoyl)-ethylamino]-benzamide, 2-(3-acetylamino-4-chlorophenylamino)-2-phenyl-N-(4-trifluoromethyl-6H-pyrazolo[4',3':3,4]benzo[1,2-d]thiazol-2-yl)-acetamide, 2-chloro-N-cyclopropyl-5-[1-methyl-1-(4-trifluoro-methyl-6H-pyrazolo[4',3':3,4]benzo[1,2-d]thiazol-2-ylcarbamoyl)-ethylamino]-benzamide, 2-(4-fluoro-3-propionylamino-phenylamino)-2-methyl-N-(4-trifluoromethyl-6H-pyrazolo[4',3':3,4]benzo[1,2-d] thiazol-2-yl)-propionamide, 2-(3-acetylamino-4-fluorophenylamino)-2-methyl-N-(4-trifluoromethyl-6H-pyrazolo[4',3':3,4]benzo[1,2-d]thiazol-2-yl)-propionamide, 2-methyl-2-(3-sulfamoylphenylamino)-N-(4-trifluoro-methyl-6H-pyrazolo[4',3':3,4]benzo[1,2-d]thiazol-2-yl)-propionamide, N-carbamoylmethyl-2-chloro-5-[1-methyl-1-(4-trifluoromethyl-6H-pyrazolo[4',3':3,4]benzo[1,2-d]thiazol-2-ylcarbamoyl)-ethylamino]-benzamide, 3-{2-chloro-5-[1-methyl-1-(4-trifluoromethyl)-6H-pyrazolo [4',3':3,4]benzo[1,2-d]thiazol-2-ylcarbamoyl-ethylamino]-benzoylamino}-propionic acid 2-(4-chloro-3-hydroxyphenylamino)-2-methyl-N-(4-trifluoromethyl-6H-pyrazolo[4',3':3,4]benzo[1,2-d]thiazol-2-yl)-propionamide, 4-{2-chloro-5-[1-methyl-1-(4-trifluoromethyl-6H-pyrazolo [4',3':3,4]benzo[1,2-d]thiazol-2-ylcarbamoyl)-ethylamino]-benzoylamino}-butyric acid, {2-chloro-5-[1-methyl-1-(4-trifluormethyl-6H-pyrazolo[4', 3':3,4]benzo[1,2-d]thiazol-2-ylcarbamoyl)-ethylamino]-benzoylamino}-acetic acid, 2-[4-chloro-3-(2-oxo-2,3-dihydroimidazol-1-yl)-phenylamino]-2-methyl-N-(4-trifluoromethyl-6H-pyrazolo[4', 3':3,4]benzo[1,2-d]thiazol-2-yl)-propionamide CAN-1388, 2-[4-chloro-3-(2,3-dihydroxy-propoxy)-phenylamino]-2-methyl-N-(4-trifluoromethyl-6H-pyrazolo[4',3':3,4]benzo [1,2-d]thiazol-2-yl)-propionamide, and 2-(3-methoxyphenylamino)-N-(6H-pyrazolo[4', 3':3,4] benzo[1,2-d]thiazol-2-yl)-propionamide.

In addition, when a compound is capable of forming a salt, a pharmaceutically acceptable salt thereof can also be used as an active ingredient.

Examples of pharmaceutically acceptable salts include hydrochlorides, hydrobromides, hydroiodides, sulfates, sulfonates, methanesulfonates, benzenesulfonates, p-toluenesulfonates, phosphates, phosphonates, acetates, citrates, benzoates, tartrates, phosphates, lactates, maleates, fumarates, malates, gluconates and salicylates, sodium salts, potassium salts, calcium salts, ammonium salts, alkylammonium salts, dialkylammonium salts, trialkylammonium salts and tetraalkylammonium salts.

Preferable examples include hydrochlorides, methanesulfonates, sodium salts and potassium salts.

In addition, compounds of general formula (1) of the present invention and salts thereof may also be solvates containing certain types of solvents, and these solvates are also included in the present invention.

Moreover, compounds of general formula (1) of the present invention may also be hydrates, and these hydrates are also included in the present invention.

Solvates refer to compounds containing a solvent in crystals thereof at a fixed stoichiometric ratio. In addition, solvates in which the solvating solvent is water are referred to as hydrates Examples of certain types of solvents include sulfoxide-based solvents as exemplified by dimethylsulfoxide, amide-based solvents as exemplified by dimethylformamide or dimethylacetamide, ether-based solvents as exemplified by ethyl ether, diisopropyl ether, dimethoxyethane, tetrahydrofuran or cyclopentyl methyl ether, halogen-based solvents as exemplified by dichloromethane, chloroform or dichloroethane, nitrile-based solvents as exemplified by acetonitrile or propionitrile, ketone-based solvents as exemplified by acetone, methyl ethyl ketone or methyl isobutyl ketone, aromatic hydrocarbon-based solvents as exemplified by benzene or toluene, ester-based solvents as exemplified by ethyl acetate, and alcohol-based solvents as exemplified by methanol, ethanol, propanol or isopropanol.

In addition, compounds of general formula (1) of the present invention, or pharmaceutically acceptable salts, hydrates or solvates thereof, can exist as arbitrary crystalline forms according to production conditions, and these crystalline forms are also contained within the scope of the present invention. In addition, vitreous states (amorphous forms) are also contained within the scope of the present invention.

A prodrug refers to a derivative of the present invention having a group able to be chemically or metabolically decomposed, or a physiologically active compound that forms a compound of the present invention by solvolysis or in vivo under physiological conditions. Methods for selecting and producing suitable prodrug derivatives are described in, for example, Design of Prodrugs, Elsevier, Amsterdam 1985. In the case a compound of the present invention has a hydroxyl group, an example of prodrug is an acyloxy derivative produced by reacting the said compound with a suitable acyl halide or suitable acid anhydride. Particularly preferable examples of acyloxy compounds for use as prodrugs include —$OCOC_2H_5$, —OCO(t-Bu), —$OCOC_{15}H_{31}$, —OCO(m-$CO_2$Na-Ph), —$OCOCH_2CH_2CO_2$Na, —$OCOCH(NH_2)CH_3$ and —$OCOCH_2N(CH_3)_2$. In the case a compound of the present invention has an amino group, an example of prodrug is an amide derivative produced by reacting the compound having an amino group with a suitable acid halide or suitable mixed acid anhydride. Particularly preferable examples of amides for use as prodrugs include —$NHCO(CH_2)_{20}OCH_3$ and —$NHCOCH(NH_2)CH_3$. In the case a compound of the present invention has a carboxyl group, examples of prodrugs include carboxylic acid esters obtained from by reacting the said compound with aliphatic alcohols or a free alcoholic hydroxyl group of 1,2- or 1,3-diglyceride. Particularly preferable examples of carboxylic acid esters for use as prodrugs include methyl ester and ethyl ester.

The following provides an explanation of a method of producing compounds of the present invention.

Furthermore, in the production methods described below, in the case a defined group either changes under the reaction conditions or is unsuitable for carrying out the production method, production can be easily carried out by applying ordinary methods used in organic synthesis chemistry such as the protection of functional groups or the deprotection thereof (see, for example, Protective Groups in Organic Synthesis, Third Edition, T. W. Greene ed., John Wiley & Sons Inc.). In addition, the order of the reaction processes, such as the introduction of substituents, can also be changed as necessary.

Production Example 1

A compound of general formula (1a), for example, among the compounds of formula (1) of the present invention can be obtained by reacting a compound of general formula (4) with a compound of general formula (5) in the presence of a dehydration-condensation agent and in an inert solvent as indicated by, for example, the following reaction scheme:

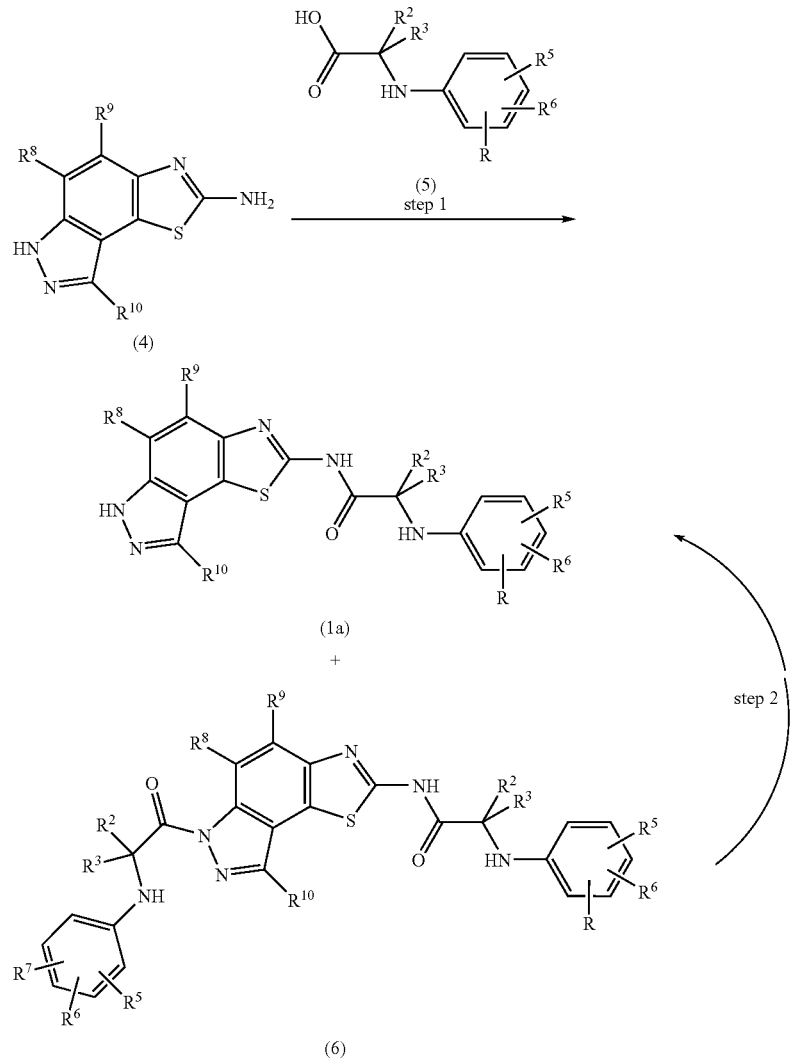

wherein, $R^2$, $R^3$, $R^5$, $R^6$, $R^7$, $R^8$, $R^9$ and $R^{10}$ are as defined above.

Step 1: Examples of solvents used in the reaction between a compound of general formula (4) and a compound of general formula (5) are indicated below:

sulfoxide-based solvents as exemplified by dimethylsulfoxide, amide-based solvents as exemplified by dimethylformamide or dimethylacetamide, ether-based solvents as exemplified by ethyl ether, dimethoxyethane, tetrahydrofuran or cyclopentyl methyl ether, halogen-based solvents as exemplified by dichloromethane, chloroform or dichloroethane, nitrile-based solvents as exemplified by acetonitrile or propionitrile, ketone-based solvents as exemplified by acetone, methyl ethyl ketone or methyl isobutyl ketone, aromatic hydrocarbon-based solvents as exemplified by benzene or toluene, hydrocarbon-based solvents as exemplified by hexane or heptane, and ester-based solvents as exemplified by ethyl acetate. In addition, the reaction can also be carried out under solvent-free conditions. Preferable examples are amide-based solvents and ether-based solvents.

The reaction temperature is normally −80° C. to the reflux temperature of the reaction solvent used, and is preferably −10 to 80° C.

The molar ratio of the reaction raw materials in terms of the ratio of the compound of general formula (5) to the compound of general formula (4) is within the range of 0.5 to 20.0 and is preferably within the range of 1.0 to 10.0.

As the dehydration-condensation agent, dicyclohexyl carbodiimide (DCC), diisopropyl carbodiimide (DIPC), N-ethyl-N'-3-dimethylaminoproyl carbodiimide (EDC=WSCI) or its hydrochloride (WSCI.HCl), benzotriazol-1-yl-tris(dimethylamino)phosphonium hexafluorophosphate (BOP) or diphenylphosphorylazide can be used alone. Alternatively those can be used in combination with N-hydroxysuccinimide (HONSu), 1-hydroxybenzotriazole (HOBt) or 3-hydroxy-4-oxo-3,4-dihydro-1,2,3-benzotriazine (HOObt). The dehydration-condensation agent is not limited to those indicated above, and a typically known dehydration-condensation agent can be used. Additives are also not limited to those indicated above, and reagents typically recognized to have effects can be used. The combination of WSCI.HCl and HOBt is used preferably.

Although a compound of general formula (6) may be formed along with a compound of general formula (1a) depending on the reaction conditions and types of substituents, a compound of general formula (6) can be converted to a compound of general formula (1a) by treating in a solvent in the presence of base as necessary.

Step 2: Examples of solvents used in the treatment of a compound of general formula (6) are indicated below:

sulfoxide-based solvents as exemplified by dimethylsulfoxide, amide-based solvents as exemplified by dimethylformamide or dimethylacetamide, ether-based solvents as exemplified by ethyl ether, dimethoxyethane, tetrahydrofuran or cyclopentyl methyl ether, halogen-based solvents as exemplified by dichloromethane, chloroform or dichloroethane, nitrile-based solvents as exemplified by acetonitrile or propionitrile, ketone-based solvents as exemplified by acetone, methyl ethyl ketone or methyl isobutyl ketone, aromatic hydrocarbon-based solvents as exemplified by benzene or toluene, hydrocarbon-based solvents as exemplified by hexane or heptane, ester-based solvents as exemplified by ethyl acetate, and alcohol-based solvents such as methanol, ethanol or ethylene glycol. In addition, the reaction can also be carried out under solvent-free conditions. Preferable examples are alcohol-based solvents.

Examples of bases include trialkylamines as exemplified by triethylamine or ethyldiisopropylamine, pyridine-based amines such as pyridine, 2,6-lutidine, 2,6-di-t-butylpyridine or 2,6-di-t-butyl-4-methylpyridine, metal alcolates such as potassium t-butoxide or sodium methoxide, and inorganic bases as exemplified by sodium hydroxide, potassium hydroxide or potassium carbonate, and preferable examples are trialkylamines.

The reaction temperature is normally −80° C. to the reflux temperature of the reaction solvent used, and is preferably −10 to 80° C.

The molar ratio of the reaction raw materials in terms of the ratio of base to the compound of general formula (6) is within the range of 0.5 to 20.0 and is preferably within the range of 1.0 to 10.0.

A compound of general formula (4) can be synthesized from a compound of general formula (7) as indicated by, for example, the following reaction scheme:

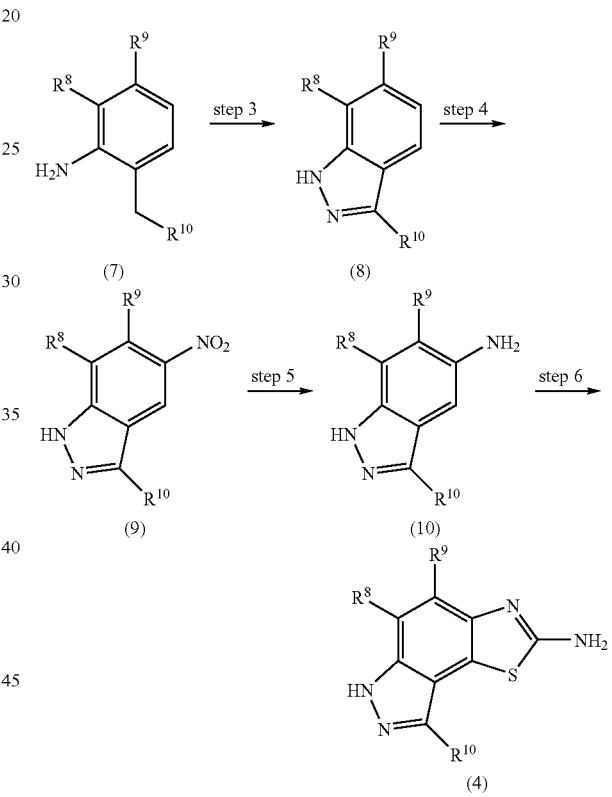

wherein, $R^8$, $R^9$ and $R^{10}$ are as defined above.

Step 3: A compound of general formula (8) can be obtained by reacting a compound of general formula (7) with a nitrous acid compound (see, for example, Pharmazie, Vol. 40, p. 105 (1985)).

For example, a compound of general formula (8) can be obtained by reacting a compound of general formula (7) with 1 to 5 equivalents of a nitrous acid compound in a solvent such as acetic acid, at a temperature of 0° C. to the boiling point of the solvent.

Examples of nitrous acid compounds that can be used include nitrites such as sodium nitrite or potassium nitrite and organic nitrite esters such as isoamyl nitrite.

Furthermore, the raw material in the form of a compound of general formula (7) can be acquired in the form of a commercially available product such as ortho-toluidine, 2,5- xylidine (Aldrich Inc.) or 3-amino-4-methyl benzotrifluoride (Fluorochem Inc.). Alternatively, this compound can also be obtained by methods typically known in the field of organic synthesis chemistry.

In addition, a compound of general formula (8) can also be obtained by reacting a compound of general formula (7) with nitrate and concentrated sulfuric acid in a mixed solvent of acetic acid and acetic anhydride (see, for example, Organic Synthesis, Vol. 42, p. 69 (1962)).

Step 4: A compound of general formula (9) can be obtained by applying a compound of general formula (8) to a nitration reaction.

For example, a compound of general formula (9) can be obtained by reacting a compound of general formula (8) with 1 to 5 equivalents of a nitrating agent in a solvent such as acetic acid, acetic anhydride or sulfuric acid at a temperature from 0° C. to the boiling point of the solvent used.

Examples of nitrating agents include concentrated nitric acid (60-80% aqueous solution), nitrate (such as sodium nitrate) and acetyl nitrate.

Step 5: A compound of general formula (10) can be obtained by applying a compound of general formula (9) to a reduction reaction.

For example, a compound of general formula (10) can be obtained by reacting a compound of general formula (9) in a solvent such as ethanol or methanol, in the presence of a hydrogenation catalyst and hydrogen at normal pressure to 120 atm, and at a temperature from 0° C. to the boiling point of the solvent used.

Examples of hydrogenation catalysts include palladium-on-carbon, platinum oxide, rhodium and platinum-on-carbon.

In addition, for example, a compound of general formula (10) can be obtained by reacting a compound of general formula (9) with 1 to 5 equivalents of a reducing agent in a solvent such as ethanol or methanol and at a temperature from 0° C. to the boiling point of the solvent used.

Examples of reducing agents include reducing metals such as iron powder, zinc powder or tin powder, and metal hydrides such as $NaBH_4$.

Step 6: A compound of general formula (4) can be obtained by reacting a compound of general formula (10) with isothiocyanate in the presence of a halogenating agent (see, for example, Synthesisi-stugard, p. 970 (2000); Synthetic Communication, p. 256 (1986)).

For example, a compound of general formula (4) can be obtained by reacting a compound of general formula (10) with 1 to 5 equivalents of isothiocyanate and 1 to 5 equivalents of a halogenating agent in a solvent such as acetic acid at a temperature from 0° C. to the boiling point of the solvent used.

Examples of halogenating agents include iodine and bromine.

Examples of isothiocyanates include sodium isothiocyanate and lead isothiocyanate.

A compound of general formula (9) can also be synthesized from a compound of general formula (7) as indicated by the following reaction scheme:

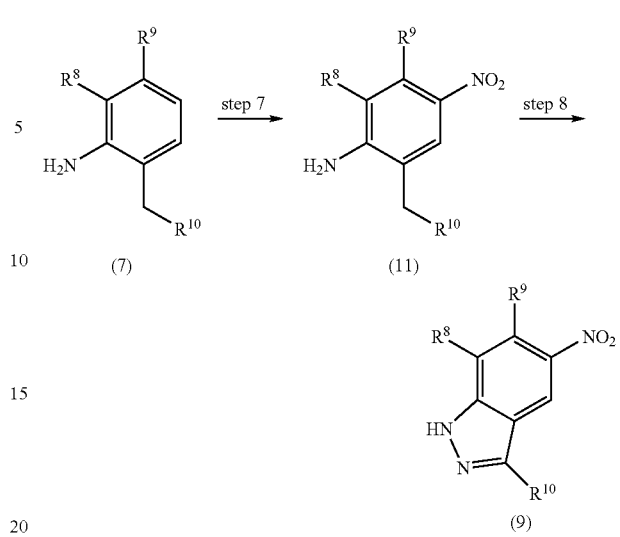

wherein, $R^8$, $R^9$ and $R^{10}$ are as defined above.

Step 7: A compound of general formula (11) can be obtained by applying a compound of general formula (7) to a nitration reaction in the same manner as step 4.

Step 8: A compound of general formula (9) can be obtained by applying a compound of general formula (11) and a nitrous acid compound to the same procedure as step 3.

A compound of general formula (5) can be obtained by reacting a compound of general formula (12) with a compound of general formula (13) in the presence of a copper catalyst and base and in an inert solvent as indicated by the following reaction scheme (step 9) (see, for example Organic Letters, Vol. 3, p. 2583 (2001)):

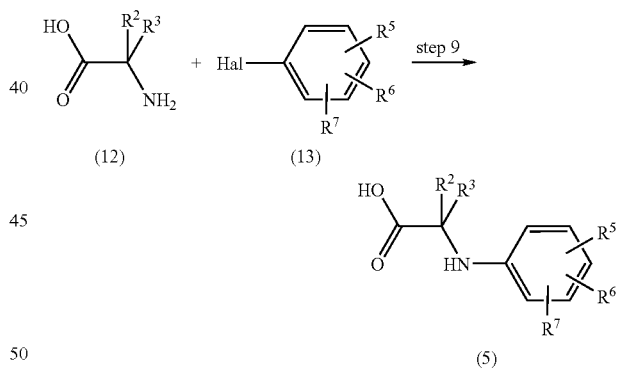

wherein, $R^2$, $R^3$, $R^5$, $R^6$ and $R^7$ are as defined above, and Hal represents a halogen atom such as a chlorine, bromine or iodine atom.

Examples of solvents used in the reaction between a compound of general formula (12) and a compound of general formula (13) are indicated below:

sulfoxide-based solvents as exemplified by dimethylsulfoxide, amide-based solvents as exemplified by dimethylformamide or dimethylacetamide, ether-based solvents as exemplified by ethyl ether, dimethoxyethane, tetrahydrofuran or cyclopentyl methyl ether, halogen-based solvents as exemplified by dichloromethane, chloroform or dichloroethane, nitrile-based solvents as exemplified by acetonitrile or propionitrile, ketone-based solvents as exemplified by acetone, methyl ethyl ketone or methyl isobutyl ketone, aromatic hydrocarbon-based solvents as exemplified by benzene or toluene, hydrocarbon-based solvents as exemplified by hexane or heptane and ester-based solvents as exemplified by ethyl acetate. In addition, the reaction can also be carried out under solvent-free conditions. Preferable examples are amide-based solvents.

Examples of copper catalysts include copper iodide, copper chloride, copper bromide, copper acetate and copper sulfate. A preferable example is copper iodide.

Examples of bases include trialkylamines as exemplified by triethylamine or ethyldiisopropylamine, pyridine-based amines such as pyridine, 2,6-lutidine, 2,6-di-t-butylpyridine or 2,6-di-t-butyl-4-methylpyridine, metal alcolates such as potassium t-butoxide or sodium methoxide, and inorganic bases as exemplified by sodium hydroxide, potassium hydroxide, potassium carbonate, potassium acetate or cesium acetate, and preferable examples are potassium acetate and cesium acetate.

The reaction temperature is normally −80° C. to the reflux temperature of the reaction solvent used, and is preferably 0 to 120° C.

The molar ratio of the reaction raw materials in terms of the ratio of the compound of general formula (13) to the compound of general formula (12) is within the range of 0.5 to 20.0 and is preferably within the range of 1.0 to 10.0.

A compound of general formula (5) can also be obtained by reacting a compound of general formula (14) with a compound of general formula (15) in an inert solvent and in the presence of a base as necessary (see, for example, Journal of organic Chemistry, Vol. 19, p. 1802 (1954)), followed by deprotecting the protective groups as necessary (step 10):

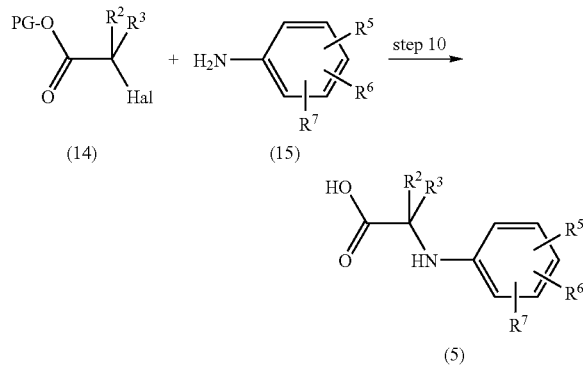

wherein, $R^2$, $R^3$, $R^5$, $R^6$ and $R^7$ are as defined above, Hal represents a halogen atom such as a chlorine, bromine or iodine atom, and PG represents a functional group such as a methyl group, ethyl group, t-butyl group or benzyl group typically known as a protective group of a carboxylic acid in organic synthesis reactions.

Examples of solvents used in the reaction between a compound of general formula (14) and a compound of general formula (15) are indicated below:

sulfoxide-based solvents as exemplified by dimethylsulfoxide, amide-based solvents as exemplified by dimethylformamide or dimethylacetamide, ether-based solvents as exemplified by ethyl ether, dimethoxyethane, tetrahydrofuran or cyclopentyl methyl ether, halogen-based solvents as exemplified by dichloromethane, chloroform or dichloroethane, nitrile-based solvents as exemplified by acetonitrile or propionitrile, ketone-based solvents as exemplified by acetone, methyl ethyl ketone or methyl isobutyl ketone, aromatic hydrocarbon-based solvents as exemplified by benzene or toluene, hydrocarbon-based solvents as exemplified by hexane or heptane, ester-based solvents as exemplified by ethyl acetate, and alcohol-based solvents as exemplified by methanol, ethanol or ethylene glycol. Moreover, mixtures of each solvent with water and biphasic solvents can also be used. In addition, the reaction can also be carried out under solvent-free conditions. Preferable examples are alcohol-based solvents, halogen-based solvents and biphasic mixed solvents of halogen-based solvents and water.

Although a base may not be added, examples of bases added as necessary include trialkylamines as exemplified by triethylamine or ethyldiisopropylamine, pyridine-based amines such as pyridine, 2,6-lutidine, 2,6-di-t-butylpyridine or 2,6-di-t-butyl-4-methylpyridine, metal alcolates such as potassium t-butoxide or sodium methoxide, and inorganic bases as exemplified by sodium hydroxide, potassium hydroxide or potassium carbonate, and preferably base is either not added or potassium t-butoxide or trialkylamines is added if added.

The reaction temperature is normally −80° C. to the reflux temperature of the reaction solvent used, and is preferably −10 to 150° C.

The molar ratio of the reaction raw materials in terms of the ratio of the compound of general formula (14) to the compound of general formula (15) is within the range of 0.5 to 20.0 and is preferably within the range of 1.0 to 10.0.

A phase transfer catalyst such as tetrabutylammonium bromide, or an additive such as sodium iodide for the purpose of enhancing halogen reactivity, may be added to the above reaction as necessary.

The deprotection reaction can be carried out by performing a typically known deprotection reaction on the corresponding protective groups (see, for example, Protective Groups in Organic Synthesis, Third edition, T. W. Greene, ed., John Wiley & Sons Inc. (1999)).

Production Example 2

In addition, a compound of general formula (1a) can be synthesized from a compound of general formula (4) as indicated by the following reaction scheme:

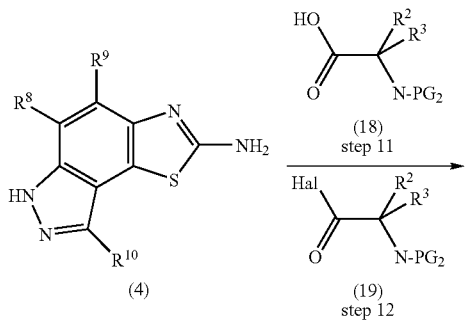

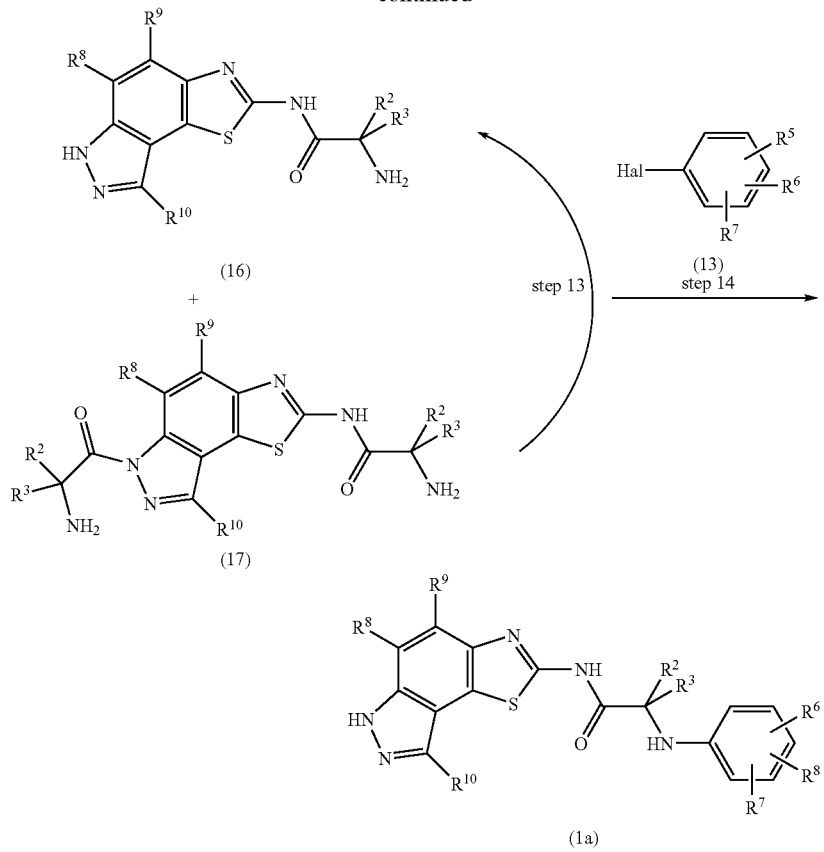

wherein, $R^2$, $R^3$, $R^5$, $R^6$, $R^7$, $R^8$, $R^9$ and $R^{10}$ are as defined above, Hal represents a halogen atom such as a chlorine, bromine or iodine atom, and $PG_2$ is a functional group typically known as an amine protective group in organic synthesis reactions.

Examples of protective groups represented by $PG_2$ used as amine protective groups include typically known acyl-based protective groups such as an acetyl group, Boc group or Cbz group, and alkyl-based protective groups such as a methyl group, and preferable examples include acyl-based protective groups.

Step 11: A compound of general formula (16) can be obtained by a dehydration-condensation reaction between a compound of general formula (4) and a compound of general formula (18) in an inert solvent, followed by deprotecting the protective groups as necessary. (That is, it can be obtained by synthesizing an amide in accordance with the procedure of the previously described step 1, followed by deprotecting the protective groups as necessary.)

Examples of solvents used in the reaction between a compound of general formula (4) and a compound of general formula (18) are indicated below:

sulfoxide-based solvents as exemplified by dimethylsulfoxide, amide-based solvents as exemplified by dimethylformamide or dimethylacetamide, ether-based solvents as exemplified by ethyl ether, dimethoxyethane, tetrahydrofuran or cyclopentyl methyl ether, halogen-based solvents as exemplified by dichloromethane, chloroform or dichloroethane, nitrile-based solvents as exemplified by acetonitrile or propionitrile, ketone-based solvents as exemplified by acetone, methyl ethyl ketone or methyl isobutyl ketone, aromatic hydrocarbon-based solvents as exemplified by benzene or toluene, hydrocarbon-based solvents as exemplified by hexane or heptane, and ester-based solvents as exemplified by ethyl acetate. In addition, the reaction can also be carried out under solvent-free conditions. Preferable examples are amide-based solvents.

The reaction temperature is normally −80° C. to the reflux temperature of the reaction solvent used, and is preferably −10 to 80° C.

The molar ratio of the reaction raw materials in terms of the ratio of the compound of general formula (18) to the compound of general formula (4) is within the range of 0.5 to 20.0 and is preferably within the range of 1.0 to 10.0.

As the dehydration-condensation agent, dicyclohexyl carbodiimide (DCC), diisopropyl carbodiimide (DIPC), N-ethyl-N'-3-dimethylaminoproyl carbodiimide (EDC=WSCI) or its hydrochloride (WSCI.HCl), benzotriazol-1-yl-tris(dimethylamino)phosphonium hexafluorophosphate (BOP) or diphenylphosphorylazide can be used alone. Alternatively those can be used in combination with N-hydroxysuccinimide (HONSu), 1-hydroxybenzotriazole (HOEt) or 3-hydroxy-4-oxo-3,4-dihydro-1,2,3-benzotriazine (HOObt). The dehydration-condensation agent is not limited to those indicated above, and a typically known dehydration-condensation agent can be used. Additives are also not limited to those indicated above, and reagents typically recognized to have effects can be used. The combination of WSCI.HCl and HOBt is used preferably.

The deprotection reaction can be carried out by performing a typically known deprotection reaction on the corresponding protective groups (see, for example, Protective Groups in Organic Synthesis, Third edition, T. W. Greene, ed., John Wiley & Sons Inc. (1999)).

Step 12: In addition, a compound of general formula (16) can be obtained by reacting a compound of general formula (4) with a compound of general formula (19) in the presence of base as necessary and in an inert solvent (see, for example, Bioorganic & Medicinal Chemistry Letters, Vol. 15, p. 1417 (2005)), followed by carrying out a deprotection reaction as necessary.

Examples of solvents used in the reaction between a compound of general formula (4) and a compound of general formula (19) are indicated below:

sulfoxide-based solvents as exemplified by dimethylsulfoxide, amide-based solvents as exemplified by dimethylformamide or dimethylacetamide, ether-based solvents as exemplified by ethyl ether, dimethoxyethane, tetrahydrofuran or cyclopentyl methyl ether, halogen-based solvents as exemplified by dichloromethane, chloroform or dichloroethane, nitrile-based solvents as exemplified by acetonitrile or propionitrile, ketone-based solvents as exemplified by acetone, methyl ethyl ketone or methyl isobutyl ketone, aromatic hydrocarbon-based solvents as exemplified by benzene or toluene, hydrocarbon-based solvents as exemplified by hexane or heptane, ester-based solvents as exemplified by ethyl acetate and alcohol-based solvents as exemplified by methanol, ethanol or ethylene glycol. In addition, the reaction can also be carried out under solvent-free conditions. Preferable examples are ether-based solvents.

Examples of bases include trialkylamines as exemplified by triethylamine or ethyldiisopropylamine, pyridine-based amines such as pyridine, 2,6-lutidine, 2,6-di-t-butylpyridine or 2,6-di-t-butyl-4-methylpyridine, metal alcolates such as potassium t-butoxide or sodium methoxide, and inorganic bases as exemplified by sodium hydroxide, potassium hydroxide or potassium carbonate, and preferable examples are trialkylamines.

The reaction temperature is normally −80° C. to the reflux temperature of the reaction solvent used, and is preferably −10 to 80° C.

The molar ratio of the reaction raw materials in terms of the ratio of the compound of general formula (19) to the compound of general formula (4) is within the range of 0.5 to 20.0 and is preferably within the range of 1.0 to 10.0.

The deprotection reaction can be carried out by performing a typically known deprotection reaction on the corresponding protective groups (see, for example, Protective Groups in Organic Synthesis, Third edition, T. W. Greene, ed., John Wiley & Sons Inc. (1999)).

Although a compound of general formula (17) may be formed along with a compound of general formula (16) depending on the reaction conditions and types of substituents, a compound of general formula (17) can be converted to a compound of general formula (16) by treating in a solvent in the presence of base as necessary.

Step 13: A compound of general formula (16) can be synthesized in accordance with the procedure of the previously described step 2.

Step 14: A compound of general formula (1a) can be obtained by reacting a compound of general formula (16) with a compound of general formula (13) in the presence of a copper catalyst and a base and in an inert solvent. (That is, it can be obtained by synthesizing using a method in accordance with step 9.)

Examples of solvents used in the reaction between a compound of general formula (16) and a compound of general formula (13) are indicated below:

sulfoxide-based solvents as exemplified by dimethylsulfoxide, amide-based solvents as exemplified by dimethylformamide or dimethylacetamide, ether-based solvents as exemplified by ethyl ether, dimethoxyethane, tetrahydrofuran or cyclopentyl methyl ether, halogen-based solvents as exemplified by dichloromethane, chloroform or dichloroethane, nitrile-based solvents as exemplified by acetonitrile or propionitrile, ketone-based solvents as exemplified by acetone, methyl ethyl ketone or methyl isobutyl ketone, aromatic hydrocarbon-based solvents as exemplified by benzene or toluene, hydrocarbon-based solvents as exemplified by hexane or heptane and ester-based solvents as exemplified by ethyl acetate. In addition, the reaction can also be carried out under solvent-free conditions. Preferable examples are amide-based solvents.

Examples of copper catalysts include copper iodide, copper chloride, copper bromide, copper acetate and copper sulfate.

Examples of bases include trialkylamines as exemplified by triethylamine or ethyldiisopropylamine, pyridine-based amines such as pyridine, 2,6-lutidine, 2,6-di-t-butylpyridine or 2,6-di-t-butyl-4-methylpyridine, metal alcolates such as potassium t-butoxide or sodium methoxide, and inorganic bases as exemplified by sodium hydroxide, potassium hydroxide, potassium carbonate, potassium acetate or cesium acetate, and preferable examples are potassium acetate and cesium acetate.

The reaction temperature is normally −80° C. to the reflux temperature of the reaction solvent used, and is preferably −10 to 120° C.

The molar ratio of the reaction raw materials in terms of the ratio of the compound of general formula (13) to the compound of general formula (16) is within the range of 0.5 to 20.0 and is preferably within the range of 1.0 to 10.0.

Production Example 3

Moreover, a compound of general formula (1a) can be synthesized from a compound of general formula (4) as indicated by the following reaction scheme:

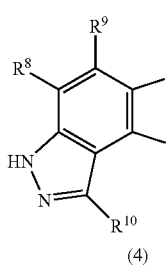

(4)

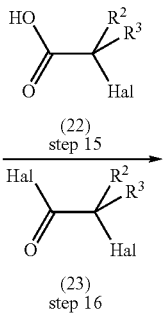

(22)
step 15

(23)
step 16

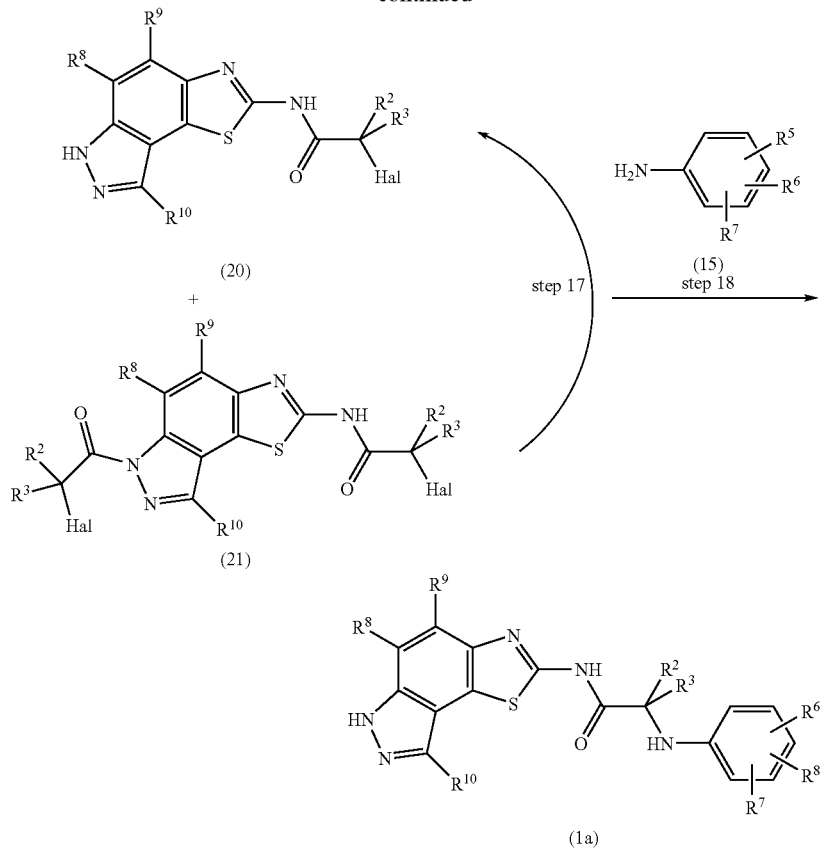

wherein, $R^2$, $R^3$, $R^5$, $R^6$, $R^7$, $R^8$, $R^9$ and $R^{10}$ are as defined above, and Hal represents a halogen atom such as a chlorine, bromine or iodine atom.

Step 15: A compound of general formula (20) can be obtained by reacting a compound of general formula (4) with a compound of general formula (22) in the presence of a dehydration-condensation agent and in an inert solvent as indicated by, for example, the aforementioned reaction scheme.

(That is, it can be synthesized by carrying out a procedure in accordance with step 1.)

Examples of solvents used in the reaction between a compound of general formula (4) and a compound of general formula (22) are indicated below:

sulfoxide-based solvents as exemplified by dimethylsulfoxide, amide-based solvents as exemplified by dimethylformamide or dimethylacetamide, ether-based solvents as exemplified by ethyl ether, dimethoxyethane, tetrahydrofuran or cyclopentyl methyl ether, halogen-based solvents as exemplified by dichloromethane, chloroform or dichloroethane, nitrile-based solvents as exemplified by acetonitrile or propionitrile, ketone-based solvents as exemplified by acetone, methyl ethyl ketone or methyl isobutyl ketone, aromatic hydrocarbon-based solvents as exemplified by benzene or toluene, hydrocarbon-based solvents as exemplified by hexane or heptane, and ester-based solvents as exemplified by ethyl acetate. In addition, the reaction can also be carried out under solvent-free conditions. Preferable examples are amide-based solvents.

The reaction temperature is normally −80° C. to the reflux temperature of the reaction solvent used, and is preferably −10 to 80° C.

The molar ratio of the reaction raw materials in terms of the ratio of the compound of general formula (22) to the compound of general formula (4) is within the range of 0.5 to 20.0 and is preferably within the range of 1.0 to 10.0.

As dehydration-condensation agents, dicyclohexyl carbodiimide (DCC), diisopropyl carbodiimide (DIPC), N-ethyl-N'-3-dimethylaminoproyl carbodiimide (EDC=WSCI) or its hydrochloride (WSCI.HCl), benzotriazol-1-yl-tris(dimethylamino)phosphonium hexafluorophosphate (BOP) or diphenylphosphorylazide can be used alone. Alternatively those can be used in combination with N-hydroxysuccinimide (HONSu), 1-hydroxybenzotriazole (HOBt) or 3-hydroxy-4-oxo-3,4-dihydro-1,2,3-benzotriazine (HOObt). The dehydration-condensation agent is not limited to those indicated above, and a typically known dehydration-condensation agent can be used. Additives are also not limited to those indicated above, and reagents typically recognized to have effects can be used. The combination of WSCI.HCl and HOBt is used preferably.

Step 16: In addition, a compound of general formula (20) can be obtained by reacting a compound of general formula (4) with a compound of general formula (23) in an inert solvent and in the presence of a base as necessary. (That is, it can be synthesized by carrying out a procedure in accordance with step 12.)

Examples of solvents used in the reaction between a compound of general formula (4) and a compound of general formula (23) are indicated below:

sulfoxide-based solvents as exemplified by dimethylsulfoxide, amide-based solvents as exemplified by dimethylformamide or dimethylacetamide, ether-based solvents as exemplified by ethyl ether, dimethoxyethane, tetrahydrofuran or cyclopentyl methyl ether, halogen-based solvents as exemplified by dichloromethane, chloroform or dichloroethane, nitrile-based solvents as exemplified by acetonitrile or propionitrile, ketone-based solvents as exemplified by acetone, methyl ethyl ketone or methyl isobutyl ketone, aromatic hydrocarbon-based solvents as exemplified by benzene or toluene, hydrocarbon-based solvents as exemplified by hexane or heptane, ester-based solvents as exemplified by ethyl acetate and alcohol-based solvents as exemplified by methanol, ethanol or ethylene glycol. In addition, the reaction can also be carried out under solvent-free conditions. Preferable examples are ether-based solvents and amide-based solvents.

Examples of bases include trialkylamines as exemplified by triethylamine or ethyldiisopropylamine, pyridine-based amines such as pyridine, 2,6-lutidine, 2,6-di-t-butylpyridine or 2,6-di-t-butyl-4-methylpyridine, and inorganic bases as exemplified by sodium hydroxide, potassium hydroxide or potassium carbonate, and preferable examples are trialkylamines.

The reaction temperature is normally −80° C. to the reflux temperature of the reaction solvent used, and is preferably −10 to 80° C.

The molar ratio of the reaction raw materials in terms of the ratio of the compound of general formula (23) to the compound of general formula (4) is within the range of 0.5 to 20.0 and is preferably within the range of 1.0 to 10.0.

Although a compound of general formula (21) may be formed along with a compound of general formula (20) depending on the reaction conditions and types of substituents, a compound of general formula (21) can be converted to a compound of general formula (20) by treating in a solvent in the presence of base as necessary.

Step 17: A compound of general formula (20) can be synthesized in accordance with the procedure of the previously described step 2.

Step 18: A compound of general formula (1a) can also be obtained by reacting a compound of general formula (20) with a compound of general formula (15) in an inert solvent and in the presence of base as necessary (see, for example, Journal of Organic Chemistry, Vol. 19, p. 1802 (1954)).

(That is, it can be synthesized by carrying out a procedure in accordance with step 10).

Examples of solvents used in the reaction between a compound of general formula (20) and a compound of general formula (15) are indicated below:

sulfoxide-based solvents as exemplified by dimethylsulfoxide, amide-based solvents as exemplified by dimethylformamide or dimethylacetamide, ether-based solvents as exemplified by ethyl ether, dimethoxyethane, tetrahydrofuran or cyclopentyl methyl ether, halogen-based solvents as exemplified by dichloromethane, chloroform or dichloroethane, nitrile-based solvents as exemplified by acetonitrile or propionitrile, ketone-based solvents as exemplified by acetone, methyl ethyl ketone or methyl isobutyl ketone, aromatic hydrocarbon-based solvents as exemplified by benzene or toluene, hydrocarbon-based solvents as exemplified by hexane or heptane, ester-based solvents as exemplified by ethyl acetate, and alcohol-based solvents as exemplified by methanol, ethanol or ethylene glycol. In addition, the reaction can also be carried out under solvent-free conditions. Preferable examples are alcohol-based solvents.

Examples of bases include trialkylamines as exemplified by triethylamine or ethyldiisopropylamine, pyridine-based amines such as pyridine, 2,6-lutidine, 2,6-di-t-butylpyridine or 2,6-di-t-butyl-4-methylpyridine, metal alcolates such as potassium t-butoxide or sodium methoxide, and inorganic bases as exemplified by sodium hydroxide, potassium hydroxide or potassium carbonate, and preferable examples include trialkylamines.

The reaction temperature is normally −80° C. to the reflux temperature of the reaction solvent used, and is preferably −10 to 150° C.

The molar ratio of the reaction raw materials in terms of the ratio of the compound of general formula (15) to the compound of general formula (20) is within the range of 0.5 to 20.0 and is preferably within the range of 1.0 to 10.0.

Moreover, a compound of general formula (20) can be synthesized from a compound of general formula (4) as indicated by the following reaction scheme:

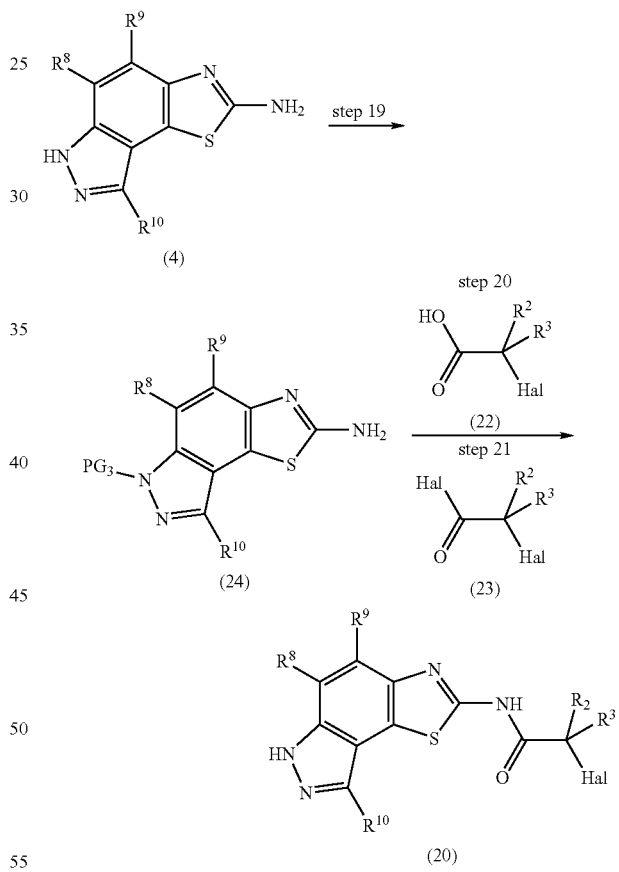

wherein, $R^2$, $R^3$, $R^5$, $R^6$, $R^7$, $R^8$, $R^9$ and $R^{10}$ are as defined above, Hal represents a halogen atom such as a chlorine, bromine or iodine atom, and $PG_3$ is a functional group typically known as an amine protective group in organic synthesis reactions.

Step 19: A compound of general formula (24) can be synthesized from a compound of general formula (4) by carrying out a reaction for introducing a protective group (see, for example, Protective Groups in Organic Synthesis, Third Edition, T. W. Green ed., John Wiley & Sons Inc.), and further carrying out a deprotection reaction of the primary amino group at position 2 as necessary.

Examples of protective groups represented by $PG_3$ used as amino group protective groups include typically known acyl-based protective groups such as an acetyl group, Boc group or Cbz group, and alkyl-based protective groups such as a methyl group, and preferable examples include acyl-based protective groups.

Step 20: A compound of general formula (20) can be obtained by reacting a compound of general formula (24) with a compound of general formula (22) in the presence of a dehydration-condensation agent and in an inert solvent followed by deprotecting the protective group at position 6.

(That is, it can be obtained by synthesizing an amide using a method in accordance with step 1, followed by deprotecting the protective group at position 6.)

Examples of solvents used in the reaction between a compound of general formula (24) and a compound of general formula (22) are indicated below:

sulfoxide-based solvents as exemplified by dimethylsulfoxide, amide-based solvents as exemplified by dimethylformamide or dimethylacetamide, ether-based solvents as exemplified by ethyl ether, dimethoxyethane, tetrahydrofuran or cyclopentyl methyl ether, halogen-based solvents as exemplified by dichloromethane, chloroform or dichloroethane, nitrile-based solvents as exemplified by acetonitrile or propionitrile, ketone-based solvents as exemplified by acetone, methyl ethyl ketone or methyl isobutyl ketone, aromatic hydrocarbon-based solvents as exemplified by benzene or toluene, hydrocarbon-based solvents as exemplified by hexane or heptane, and ester-based solvents as exemplified by ethyl acetate. In addition, the reaction can also be carried out under solvent-free conditions. Preferable examples are amide-based solvents.

The reaction temperature is normally −80° C. to the reflux temperature of the reaction solvent used, and is preferably −10 to 80° C.

The molar ratio of the reaction raw materials in terms of the ratio of the compound of general formula (22) to the compound of general formula (24) is within the range of 0.5 to 20.0 and is preferably within the range of 1.0 to 10.0.

As the dehydration-condensation agent, dicyclohexyl carbodiimide (DCC), diisopropyl carbodiimide (DIPC), N-ethyl-N'-3-dimethylaminoproyl carbodiimide (EDC=WSCI) or its hydrochloride (WSCI.HCl), benzotriazol-1-yl-tris(dimethylamino)phosphonium hexafluorophosphate (BOP) or diphenylphosphorylazide can be used alone. Alternatively those can be used in combination with N-hydroxysuccinimide (HONSu), 1-hydroxybenzotriazole (HOBt) or 3-hydroxy-4-oxo-3,4-dihydro-1,2,3-benzotriazine (HOObt). The dehydration-condensation agent is not limited to those indicated above, and a typically known dehydration-condensation agent can be used. Additives are also not limited to those indicated above, and reagents typically recognized to have effects can be used. The combination of WSCI.HCl and HOBt is used preferably.

The deprotection reaction can be carried out by performing a typically known deprotection reaction on the corresponding protective groups (see, for example, Protective Groups in Organic Synthesis, Third edition, T. W. Greene, ed., John Wiley & Sons Inc. (1999)).

Step 21: In addition, a compound of general formula (20) can be obtained by reacting a compound of general formula (24) with a compound of general formula (23) in the presence of base and in an inert solvent followed by deprotecting the amino group at position 6 as necessary. (That is, it can be obtained by synthesizing an amide using a method in accordance with step 12, followed by deprotecting the amino group at position 6 as necessary).

Examples of solvents used in the reaction between a compound of general formula (24) and a compound of general formula (23) are indicated below:

sulfoxide-based solvents as exemplified by dimethylsulfoxide, amide-based solvents as exemplified by dimethylformamide or dimethylacetamide, ether-based solvents as exemplified by ethyl ether, dimethoxyethane, tetrahydrofuran or cyclopentyl methyl ether, halogen-based solvents as exemplified by dichloromethane, chloroform or dichloroethane, nitrile-based solvents as exemplified by acetonitrile or propionitrile, ketone-based solvents as exemplified by acetone, methyl ethyl ketone or methyl isobutyl ketone, aromatic hydrocarbon-based solvents as exemplified by benzene or toluene, hydrocarbon-based solvents as exemplified by hexane or heptane, ester-based solvents as exemplified by ethyl acetate and alcohol-based solvents as exemplified by methanol, ethanol or ethylene glycol. In addition, the reaction can also be carried out under solvent-free conditions. Preferable examples are ether-based solvents.

Examples of bases include trialkylamines as exemplified by triethylamine or ethyldiisopropylamine, pyridine-based amines such as pyridine, 2,6-lutidine, 2,6-di-t-butylpyridine or 2,6-di-t-butyl-4-methylpyridine, and inorganic bases as exemplified by sodium hydroxide, potassium hydroxide or potassium carbonate, and preferable examples are trialkylamines.

The reaction temperature is normally −80° C. to the reflux temperature of the reaction solvent used, and is preferably −10 to 80° C.

The molar ratio of the reaction raw materials in terms of the ratio of the compound of general formula (23) to the compound of general formula (24) is within the range of 0.5 to 20.0 and is preferably within the range of 1.0 to 10.0.

The deprotection reaction can be carried out by performing a typically known deprotection reaction on the corresponding protective groups (see, for example, Protective Groups in Organic Synthesis, Third edition, T. W. Greene, ed., John Wiley & Sons Inc. (1999)).

The following indicates examples of other methods for synthesizing a compound of general formula (4).

A compound of general formula (4) can also be synthesized from a compound of general formula (25) and hydrazine in accordance with a method described in the literature (see, for example, Journal of Medicinal Chemistry, Vol. 47, p. 6435 (2004)).

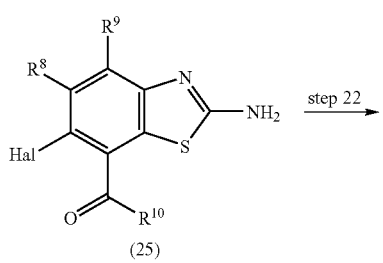

-continued

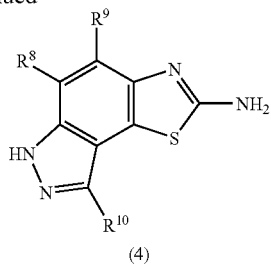

(4)

In the formulas, $R^8$, $R^9$ and $R^{10}$ are as defined above, and Hal represents a halogen atom such as a chlorine atom, bromine atom or iodine atom.

A compound of general formula (4) can also be synthesized from a compound of general formula (26) and ammonia in accordance with a method described in the literature (see, for example, Tetrahedron Letters, Vol. 45, p. 6295 (2004)).

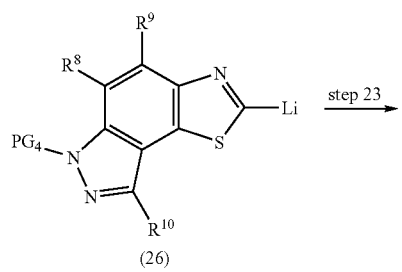

(26)

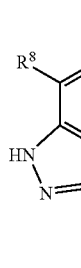

(4)

In the formulas, $R^8$, $R^9$ and $R^{10}$ are as defined above, and $PG_4$ is a functional group typically known as an amine protective group in organic synthesis reactions.

Examples of protective groups represented by $PG_4$ used as amine protective groups include typically known acyl-based protective groups such as an acetyl group, Boc group or Cbz group, and alkyl-based protective groups such as a methyl group, and preferable examples include acyl-based protective groups.

A compound of general formula (4) can also be synthesized from a compound of general formula (27) in accordance with a method described in the literature (see, for example, Tetrahedron, Vol. 54, p. 3197 (1998)).

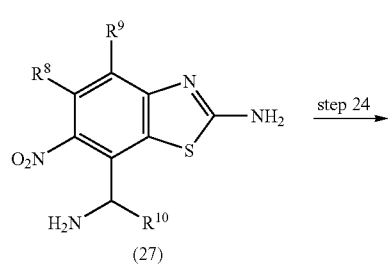

(27)

-continued

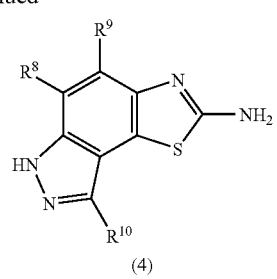

(4)

In the formulas, $R^8$, $R^9$ and $R^{10}$ are as defined above.

A compound of general formula (4) can also be synthesized from a compound of general formula (28) in accordance with a method described in the literature (see, for example, Journal of Heterocyclic Chemistry, Vol. 1, p. 239 (1964)).

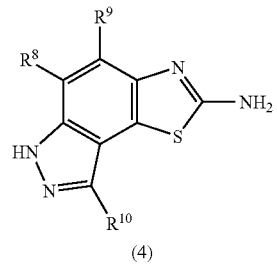

(28)

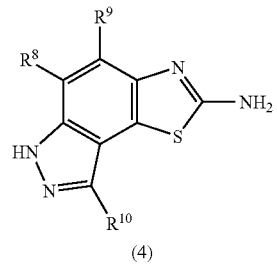

(4)

In the formulas, $R^8$, $R^9$ and $R^{10}$ are as defined above.

A compound of general formula (4) can also be synthesized from a compound of general formula (29) in accordance with a method described in the literature (see, for example, Justus Liebigs Annalen der Chemie, Vol. 681, p. 45 (1965)).

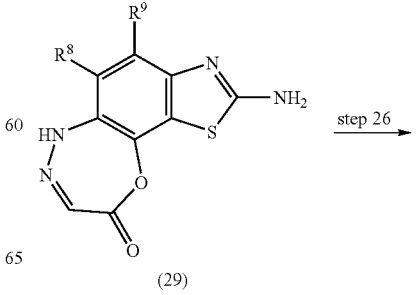

(29)

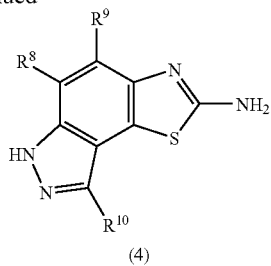

(4)

In the formulas, $R^8$, $R^9$ and $R^{10}$ are as defined above.

A compound of general formula (4) can also be synthesized from a compound of general formula (30) and ammonia in accordance with a method described in the literature (see, for example, European Journal of Medicinal Chemistry, Vol. 13, p. 171 (1978)).

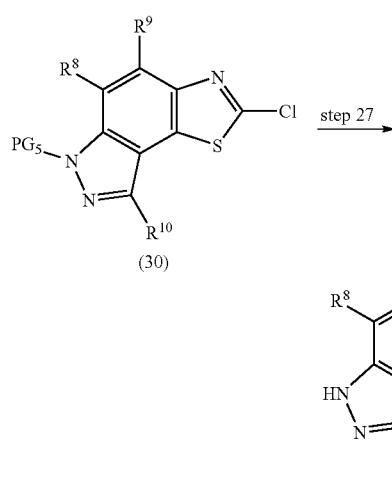

In the formulas, $R^8$, $R^9$ and $R^{10}$ are as defined above, and $PG_5$ is a functional group typically known as an amine protective group in organic synthesis reactions.

Examples of protective groups represented by $PG_5$ used as amine protective groups include typically known acyl-based protective groups such as an acetyl group, Boc group or Cbz group, and alkyl-based protective groups such as a methyl group, and preferable examples include acyl-based protective groups.

A compound of general formula (4) can also be synthesized from a compound of general formula (31) in accordance with a method described in the literature (see, for example, Journal of Chemical Research Synopses, 1986, p. 136).

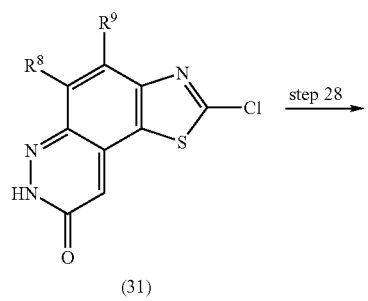

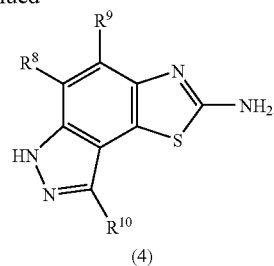

(4)

In the formulas, $R^8$, $R^9$ and $R^{10}$ are as defined above.

A compound of general formula (4) can also be synthesized from a compound of general formula (32) by a photo-reaction.

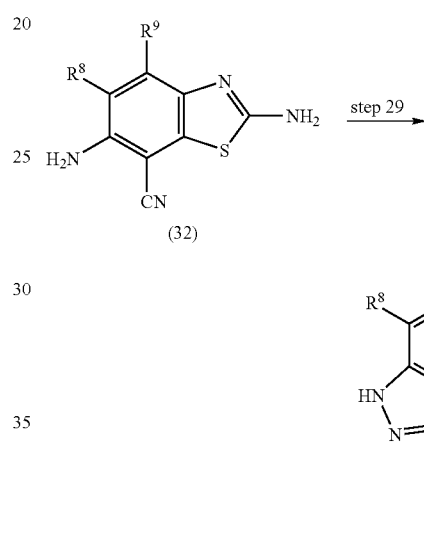

In the formulas, $R^8$, $R^9$ and $R^{10}$ are as defined above.

A compound of general formula (4) can also be synthesized from a compound of general formula (33) by a reduction reaction followed by treatment with base.

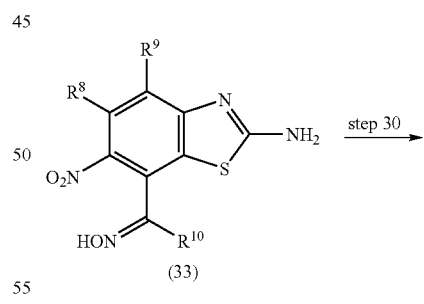

In the formulas, $R^8$, $R^9$ and $R^{10}$ are as defined above.

The following indicates reference examples for other methods of synthesizing a compound of general formula (1).

A compound of general formula (1a) can also be synthesized from a compound of general formula (34) and hydrazine in accordance with a method described in the literature (see, for example, Journal of Medicinal Chemistry, Vol. 47, p. 6435 (2004)).

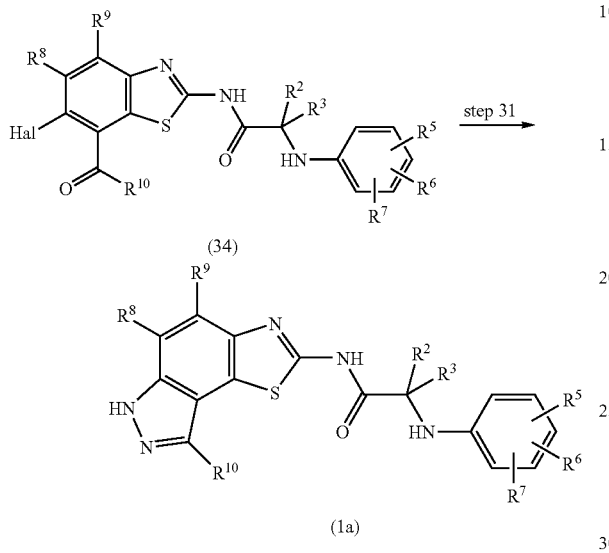

In the formulas, $R^2$, $R^3$, $R^5$, $R^6$, $R^7$, $R^8$, $R^9$ and $R^{10}$ are as defined above, and Hal represents a halogen atom such as a chlorine atom, bromine atom or iodine atom.

A compound of general formula (1a) can also be synthesized from a compound of general formula (35) in accordance with a method described in the literature (see, for example, Synthetic Communications, Vol. 23, p. 2347 (1993)).

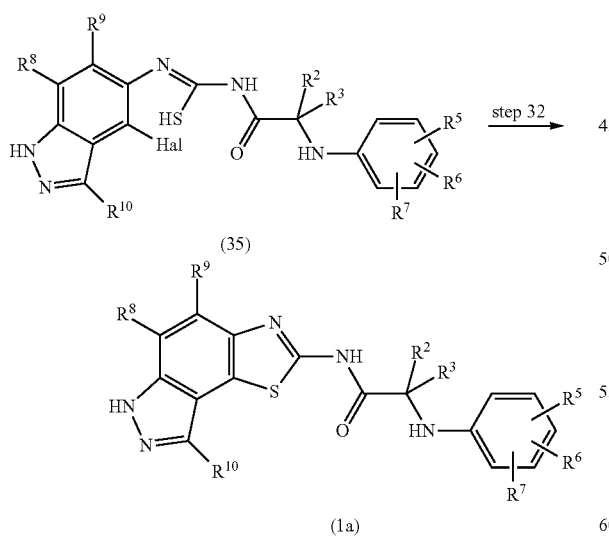

In the formulas, $R^2$, $R^3$, $R^5$, $R^6$, $R^7$, $R^8$, $R^9$ and $R^{10}$ are as defined above, and Hal represents a halogen atom such as a chlorine atom, bromine atom or iodine atom.

A compound of general formula (1a) can also be synthesized from a compound of general formula (36) and a compound of general formula (37) in accordance with a method described in the literature (see, for example, Revue Roumaine de Chemie, Vol. 24, p. 393 (1988)).

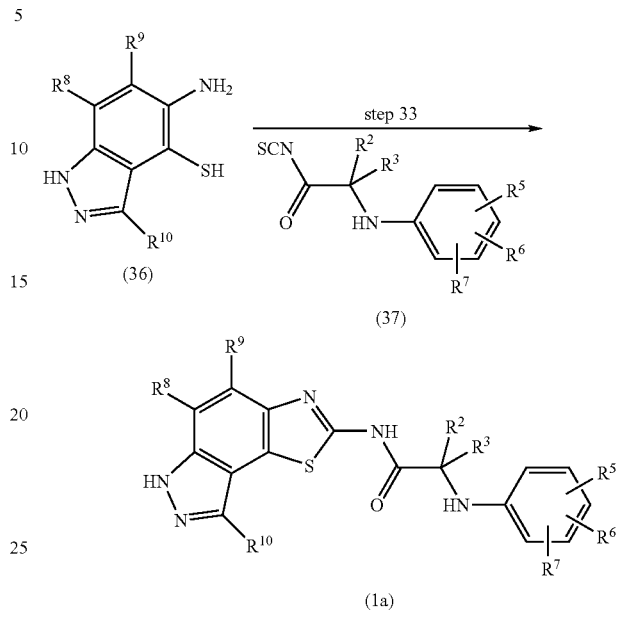

In the formulas, $R^2$, $R^3$, $R^5$, $R^6$, $R^7$, $R^8$, $R^9$ and $R^{10}$ are as defined above.

A compound of general formula (1a) can also be synthesized from a compound of general formula (38) and a compound of general formula (39), and further if necessary, reacting a compound of general formula (39') in the presence of base.

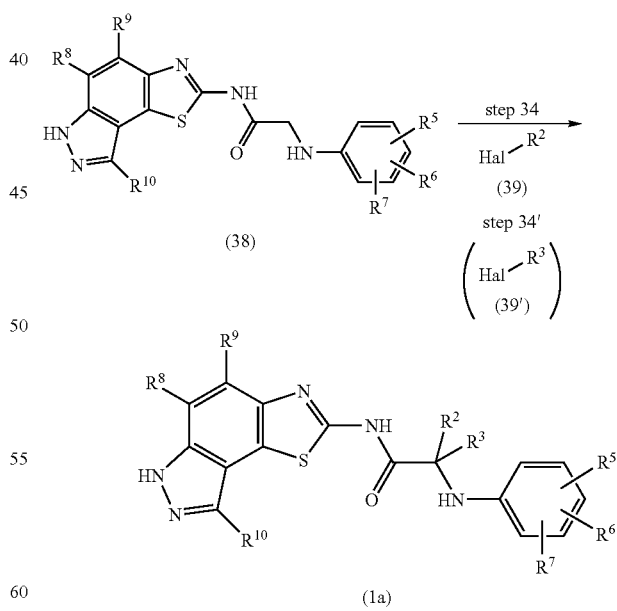

In the formulas, $R^2$, $R^3$, $R^5$, $R^6$, $R^7$, $R^8$, $R^9$ and $R^{10}$ are as defined above.

A compound of general formula (1a) can also be synthesized by treating a compound of general formula (40) in the presence of a Grubbs catalyst.

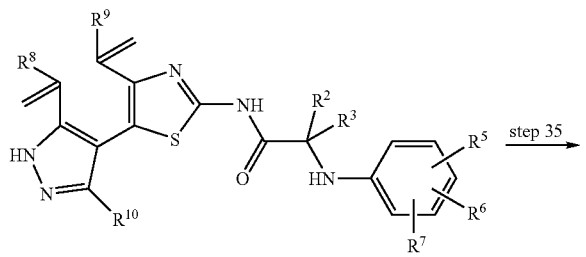

(40)

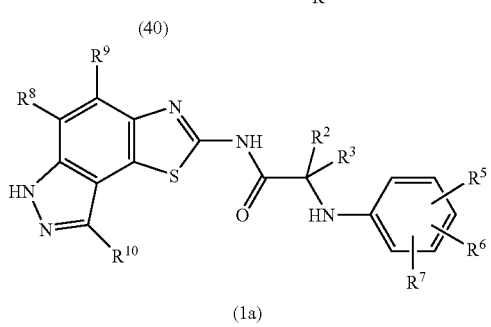

(1a)

In the formulas, $R^2$, $R^3$, $R^5$, $R^6$, $R^7$, $R^8$, $R^9$ and $R^{10}$ are as defined above.

A compound of general formula (1a) can also be synthesized by applying a compound of general formula (41) and a compound of general formula (42) to a Diels-Alder reaction.

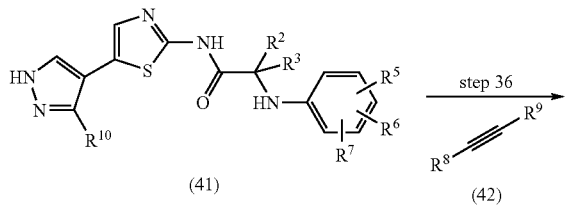

(41)      (42)

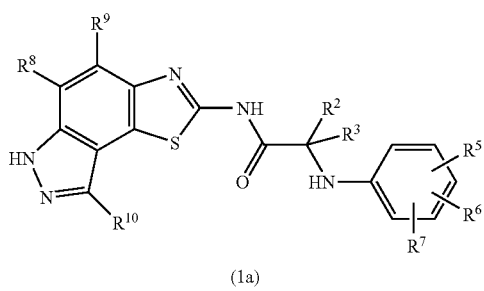

(1a)

In the formulas, $R^2$, $R^3$, $R^5$, $R^6$, $R^7$, $R^8$, $R^9$ and $R^{10}$ are as defined above.

In addition, in the production methods described above, a compound of general formula (1) of the present invention can be synthesized using methods in accordance with each step by using a compound of the following general formula (43) instead of a compound of general formula (5) in step 1, by using a compound of the following formula (44) instead of a compound of general formula (13) in step 9, and by using a compound of the following formula (45) instead of a compound of general formula (15) in step 10.

(43)

(44)

(45)

In the formulas, $R^2$ and $R^3$ are as defined above, Hal represents a halogen atom such as a chlorine atom, bromine atom or iodine atom, and Heterocyclyl represents a $C_{4-9}$ heterocyclic group. In addition, a $C_{4-9}$ heterocyclic group is as defined above and is optionally substituted with substituents $R^5$, $R^6$ and $R^7$ at those locations able to be substituted in the $C_{4-9}$ heterocyclic group, and the $R^5$, $R^6$ and $R^7$ are as defined above.

These compounds can also be obtained by utilizing other typically known organic chemistry reactions in addition to those described above.

The present invention also relates to a pharmaceutical composition comprising as an active ingredient thereof at least one type of α-amino acid derivative of the aforementioned formula (1), or a pharmaceutically acceptable salt, prodrug or solvate thereof.

As previously described, the inventors have found that a compound of general formula (1) has potent βARK1 inhibitory activity. The expressed amounts of βARK1 mRNA are increased considerably in the hearts of patients following heart failure, and cardiac βAR is widely known to be desensitized (see, for example, the aforementioned Non-Patent Documents 1 and 2). Similar effects are also obtained in various heart failure animal models, and phosphorylation and desensitization of cardiac βAR by βARK1 are believed to have the possibility of being a factor responsible for exacerbating the pathology of heart failure.

Since conventional drugs for the treatment of heart failure, as exemplified by cardiotonics, β-blockers, inhibitors of angiotensin-converting enzyme, angiotensin II antagonists and calcium antagonists, have disadvantages such as causing an increase in mortality rate due to long-term administration of cardiotonics, resulting in insufficient effects of inhibitors of angiotensin-converting enzyme and angiotensin II antagonists, and requiring hospitalized monitoring due to the negative inotropic action of B-blockers, a drug is sought that is safer and more highly effective.

In order to solve these problems, the inventors conducted exploratory research on compounds having βARK1 inhibitory activity, and have found that compounds of general formula (1) have potent βARK1 inhibitory activity.

This technology is useful for the purpose of preventing and treating heart failure, for which phosphorylation and desensitization of cardiac βAR by βARK1 are considered to have the possibility of being an exacerbating factor, and preventing exacerbation of prognosis based on heart failure pathology.

Thus, the present invention relates to a βARK1 inhibitor or medicament for preventing or treating heart failure comprising as an active ingredient thereof at least one an α-amino acid derivative of the aforementioned formula (1), or a pharmaceutically acceptable salt, prodrug or solvate thereof. In addition, the present invention relates to a method for preventing or treating heart failure by administering the inhibitor/medicament to mammals, including humans. Moreover, the present invention relates to the use of an α-amino acid derivative of formula (1) above for the manufacture of a medicament for preventing or treating heart failure.

Particularly preferred α-amino acid derivatives of the aforementioned formula (1) as an active ingredient of a βARK1 inhibitor or medicament for the prevention or treatment of heart failure are compounds of formula (3):

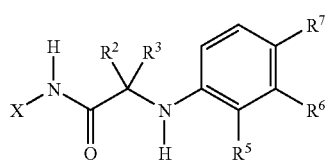

(3)

wherein, at least one of $R^5$, $R^6$ and $R^7$ is a hydrogen atom, while the remaining two each independently represent groups selected from the group consisting of a fluorine atom, chlorine atom, hydroxyl group, methoxy group, methyl group, —O(CH$_2$)$_3$SO$_2$NH$_2$, —O(CH$_2$)$_3$CONH$_2$, —O(CH$_2$)$_3$COOH, —COOH, —COOMe, —COOEt, —COO(i-Pr), —CONH$_2$, —CONHMe, —CONHEt, —CONMe$_2$, —CONEtMe, —CONH(i-Pr), —CONH(c-Pr), —SO$_2$NH$_2$, —NHSO$_2$Me, CONHCH$_2$CONH$_2$, —CONH(CH$_2$)$_2$CONH$_2$, —CONH(CH$_2$)$_3$CONH$_2$, —CONHCH$_2$COOH, —CONH(CH$_2$)$_2$COOH, —CONH(CH$_1$)$_3$COOH, —CONHCH$_2$COO(CH$_2$)$_2$OH, 2-oxo-1-imidazolyl group, —NHCOMe, —NHCOEt, —NHCO(c-Pr), —NHCOt-Bu, —NHCOOMe, —NHCOOEt, —NHCOO(t-Bu), —NHCOO(c-Pr), —NHCO$_2$CH$_2$OH, —NHCO$_2$ (CH$_2$)$_2$OH, —NHCO$_2$ (CH$_2$)$_3$OH, nitro group and —NHCONHMe.

More preferable compounds are those of formula (3) above in which at least one of $R^5$, $R^6$ and $R^7$ is a hydrogen atom, while the remaining two each independently represent groups selected from the group consisting of a fluorine atom, chlorine atom, hydroxyl group, methoxy group, —NHCOMe, —NHCOEt, —COOMe, —COOEt, —CONH$_2$, —CONHMe, —CONHEt, —CONH(c-Pr), —SO$_2$NH$_2$, —CONHCH$_2$CONH$_2$, —CONHCH$_2$COOH, —CONH(CH$_2$)$_2$COOH, —CONH(CH$_2$)$_3$COOH and a 2-oxo-1-imidazolyl group.

Moreover, the following lists examples of compounds that are preferable for the βARK1 inhibitor or medicament for preventing or treating heart failure of the present invention.

Compounds of Table 1: compounds nos. 1 to 10, 13, 15, 19, 21 to 24, 26, 29, 30, 32 to 35, 38, 42, 43, 46, 48 to 59, 65, 67, 69 to 71, 73 to 75, 78 to 81, 83 to 96, 103 to 105, 108 to 110, 112 to 123, 125 to 131 and 133 to 144.

Although the following indicates specific examples of compounds that can be used particularly preferably for the βARK1 inhibitor or medicament for preventing or treating heart failure of the present invention, the present invention is not limited thereto.

2-(4-chloro-3-hydroxyphenylamino)-N-(6H-pyrazolo[4',3':3,4]benzo[1,2-d]thiazol-2-yl)-acetamide,
2-(3-hydroxyphenylamino)-2-methyl-N-(6H-pyrazolo[4',3':3,4]benzo[1,2-d]thiazol-2-yl)-propionamide,
2-(4-chlorophenylamino)-3-hydroxy-N-(6H-pyrazolo[4',3':3,4]benzo[1,2-d]thiazol-2-yl)-propionamide,
2-(4-chlorophenylamino)-2-methyl-N-(6H-pyrazolo[4',3':3,4]benzo[1,2-d]thiazol-2-yl)-propionamide,
2-(4-chlorophenylamino)-N-(6H-pyrazolo[4',3':3,4]benzo[1,2-d]thiazol-2-yl)-propionamide,
2-(3-acetylamino-4-chlorophenylamino)-N-(6H-pyrazolo[4',3':3,4]benzo[1,2-d]thiazol-2-yl)-acetamide,
1-(4-chlorophenylamino)-N-(6H-pyrazolo[4',3':3,4]benzo[1,2-d]thiazol-2-yl)-cyclopropanecarboxamide,
2-chloro-5-[1-(6H-pyrazolo[4',3':3,4]benzo[1,2-d]thiazol-2-ylcarbamoyl)-cyclopropylamino]-benzoic acid ethyl ester,
2-(3-acetylamino-4-chlorophenylamino)-2-methyl-N-(6H-pyrazolo[4',3':3,4]benzo[1,2-d]thiazol-2-yl)-propionamide,
1-(3-acetylamino-4-fluorophenylamino)-N-(6H-pyrazolo[4',3':3,4]benzo[1,2-d]thiazol-2-yl)-cyclopropane-carboxamide,
1-(4-fluoro-3-propionylamino-phenylamino)-N-(6H-pyrazolo[4',3':3,4]benzo[1,2-d]thiazol-2-yl)cyclopropane-carboxamide,
2-(4-chloro-3-propionylamino-phenylamino)-2-methyl-N-(6H-pyrazolo[4',3':3,4]benzo[1,2-d]thiazol-2-yl)-propionamide,
2-(3-acetylamino-4-chlorophenylamino)-2-methyl-N-(4-trifluoromethyl-(6H-pyrazolo[4',3':3,4]benzo[1,2-d]thiazol-2-yl)-propionamide,
2-chloro-N-methyl-5-[1-(6H-pyrazolo[4',3':3,4]benzo[1,2-d]thiazol-2-ylcarbamoyl)-cyclopropylamino]-benzamide,
2-chloro-N-methyl-5-[1-methyl-1-(4-trifluoromethyl)-6H-pyrazolo[4',3':3,4]benzo[1,2-d]thiazol-2-ylcarbamoyl-ethylamino]-benzamide,
2-(4-chloro-3-propionylamino-phenylamino)-2-methyl-N-(4-trifluoromethyl)-6H-pyrazolo[4',3':3,4]benzo[1,2-d]thiazol-2-yl)-propionamide,
2-chloro-5-[1-methyl-1-(4-trifluoromethyl-6H-pyrazolo[4',3':3,4]benzo[1,2-d]thiazol-2-ylcarbamoyl)-ethylamino]-benzamide,
1-(4-chlorophenylamino)-N-(4-methyl-6H-pyrazolo[4',3':3,4]benzo[1,2-d]thiazol-2-yl)-cyclopropanecarboxamide,
N-ethyl-2-fluoro-5-[1-methyl-1-(4-trifluoromethyl)-6H-pyrazolo[4',3':3,4]benzo[1,2-d]thiazol-2-ylcarbamoyl)-ethylamino]-benzamide,
2-chloro-N-ethyl-5-[1-methyl-1-(4-trifluoromethyl)-6H-pyrazolo[4',3':3,4]benzo[1,2-d]thiazol-2-ylcarbamoyl)-ethylamino]-benzamide,
2-(3-acetylamino-4-chlorophenylamino)-2-phenyl-N-(4-trifluoromethyl-6H-pyrazolo[4',3':3,4]benzo[1,2-d]thiazol-2-yl)-acetamide,
2-chloro-N-cyclopropyl-5-[1-methyl-1-(4-trifluoro-methyl-6H-pyrazolo[4',3':3,4]benzo[1,2-d]thiazol-2-ylcarbamoyl)-ethylamino]-benzamide,
2-(4-fluoro-3-propionylamino-phenylamino)-2-methyl-N-(4-trifluoromethyl-6H-pyrazolo[4',3':3,4]benzo[1,2-d]thiazol-2-yl)-propionamide,
2-(3-acetylamino-4-fluorophenylamino)-2-methyl-N-(4-trifluoromethyl-6H-pyrazolo[4',3':3,4]benzo[1,2-d]thiazol-2-yl)-propionamide,
2-methyl-2-(3-sulfamoylphenylamino)-N-(4-trifluoro-methyl-6H-pyrazolo[4',3':3,4]benzo[1,2-d]thiazol-2-yl)-propionamide,
N-carbamoylmethyl-2-chloro-5-[1-methyl-1-(4-trifluoro-methyl-6H-pyrazolo[4',3':3,4]benzo[1,2-d]thiazol-2-ylcarbamoyl)-ethylamino]-benzamide,
3-{2-chloro-5-[1-methyl-1-(4-trifluoromethyl-6H-pyrazolo[4',3':3,4]benzo[1,2-d]thiazol-2-ylcarbamoyl)-ethylamino]-benzoylamino}-propionic acid
2-(4-chloro-3-hydroxyphenylamino)-2-methyl-N-(4-trifluoromethyl-6H-pyrazolo[4',3':3,4]benzo[1,2-d]thiazol-2-yl)-propionamide,
4-{2-chloro-5-[1-methyl-1-(4-trifluoromethyl-6H-pyrazolo[4',3':3,4]benzo[1,2-d]thiazol-2-ylcarbamoyl)-ethylamino]-benzoylamino}-acetic acid, {2-chloro-5-[1-methyl-1-(4-trifluormethyl-6H-pyrazolo[4',3':3,4]benzo[1,2-d]thiazol-2-ylcarbamoyl)-ethylamino]-benzoylamino}-butyric acid, and 2-[4-chloro-3-(2-oxo-2,3-dihydroimidazol-1-yl)-phenylamino]-2-methyl-N-(4-trifluoromethyl-6H-pyrazolo[4',3':3,4]benzo[1,2-d]thiazol-2-yl)-propionamide.

Moreover, the inventors have found that compounds of formula (1) of the present invention have antitumor activity in addition to βARK1 inhibitory activity, and have dual inhibitory activity on Aurora kinase and CDK in particular, and are useful for cell proliferative diseases such as cancer.

Thus, the present invention includes a step comprising administrating an antitumor agent comprising an α-amino acid derivative as an active ingredient to a mammal in need of the prevention or treatment of cancer.

In a preferred embodiment, the present invention provides a method for preventing or treating cancer in mammals by administering a selective Aurora/CDK dual inhibitor. A selective Aurora/CDK dual inhibitor refers to that which contains as an active ingredient thereof a compound that simultaneously inhibits Aurora and CDK without substantially inhibiting enzymes involved in other cell proliferation.

The antitumor agent of the present invention is particularly effective for patients highly expressing Aurora and CDK.

Examples of cancer for which the antitumor agent of the present invention can be used preferably include lung cancer, non-small-cell lung cancer (NSCLC), bone cancer, pancreatic cancer, skin cancer, head and neck cancers, melanomas in the skin or eye, uterine cancer, ovarian cancer, rectal cancer, cancers of the anal region, gastric cancer, colon cancer, breast cancer, gynecological cancers (such as uterine sarcoma, tubal carcinoma, endometrial cancer, cervical cancer, vaginal cancer or vulvar cancer), Hodgkin's disease, esophageal cancer, small intestinal cancer, endocrine cancers (such as thyroid cancer, parathyroid cancer or adrenal cancer), soft tissue cancer, urethral cancer, penile cancer, prostate cancer, chronic or acute leukemia, lymphocytic lymphosarcoma, bladder cancer, renal and ureteral cancer (such as renal cell carcinoma or renal pelvic cancer), pediatric tumors, malignant tumors of the central nervous system (such as primary CNS lymphoma), spinal cancer, brain stem tumors or pituitary adenoma, Barrett's esophagus (precancer syndrome), skin neoplasms, psoriasis, mycosis, fungoides, prostatomegaly, human papilloma virus (HPV) and other mammalian diseases, and is particularly preferably used for the treatment of colon cancer, rectal cancer, lung cancer, breast cancer, ovarian cancer, prostate cancer and leukemia.

In addition, although the antitumor agent of the present invention contains an effective amount of a compound of formula (1), or a salt, prodrug or solvate thereof, and a pharmaceutically acceptable carrier, if necessary, it may also contain other chemotherapeutic agents.

The chemotherapeutic agent may be any such agent selected from the group consisting of cell division inhibitors, alkylating agents, metabolism inhibitors, intercalating antibiotics, growth factor inhibitors, cell cycle inhibitors, enzymes, enzyme inhibitors, aromatase inhibitors, topoisomerase inhibitors, biological response modifiers, anti-hormone agents, anti-estrogen agents, anti-androgen agents and vascularization inhibitors.

Particularly preferred α-amino acid derivatives of the aforementioned formula (1) as an active ingredient of such a dual Aurora/CDK inhibitor or antitumor agent are compounds of formula (3):

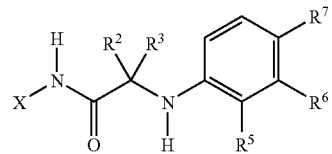

(3)

wherein, at least one of $R^5$, $R^6$ and $R^7$ is a hydrogen atom, while the remaining two each independently represent groups selected from the group consisting of a fluorine atom, chlorine atom, methyl group, hydroxyl group, methoxy group, hydroxymethyl group, —O(CH$_2$)$_k$SO$_2$NH$_2$, —OCH$_2$CH(OH)CH$_2$OH, —COOH, —COOMe, —COOEt, —COO(i-Pr), —CONHOBn, —CONH$_2$, —CONHMe, —CONHEt, —CONMe$_2$, —CONEt$_2$, —CONH(c-Pr), —NH$_2$, —NHCOMe, —NHCOEt, —NHCO(c-Pr), —NHCO(t-Bu), —NHCOOMe, —NHSO$_2$Me, —SO$_2$NH$_2$, —SO$_2$NHMe, —NO$_2$, —CONHCH$_2$COOH, —NHCO$_2$(CH$_2$)$_2$OH, —CONH(CH$_2$)$_2$COOH, —CONH(CH$_2$)$_3$COOH, —CONHCH$_2$CONH$_2$, —CONH(CH$_2$)$_2$CONH$_2$, —CONH(CH$_2$)$_3$SO$_2$NH$_2$, —CONHCH$_2$CO$_2$(CH$_2$)$_2$OH, —NHCONHMe, —CON(Me)OMe and a 2-oxo-1-imidazolyl group.

Examples of more preferable compounds include those of formula (3) in which at least one of $R^5$, $R^6$ and $R^7$ is a hydrogen atom, while the remaining two each independently represent groups selected from the group consisting of a fluorine atom, chlorine atom, hydroxyl group, methoxy group, —OCH$_2$CH(OH)CH$_2$OH, —CONHMe, —CONHEt, —CONH(c-Pr), —NHCOMe, —NHCOEt, —SO$_2$NH$_2$, —CONHCH$_2$COOH, —CONH(CH$_2$)$_3$COOH and —CONHCH$_2$CONH$_2$.

Moreover, the following lists examples of compounds that are preferable for the dual Aurora/CDK inhibitor or antitumor agent of the present invention:

Compounds of Table 1: compounds nos. 2, 6, 16, 22, 23, 33, 35, 53, 55, 60, 75, 81, 82, 84 to 86, 95, 98, 99, 101, 102, 109, 117, 120, 122, 126, 128, 129, 131, 135 to 139, 144 and 145.

Although the following indicates specific examples of compounds able to be used particularly preferably for the dual Aurora/CDK inhibitor or antitumor agent of the present invention, the present invention is not limited thereto.

2-(3-acetylamino-4-chlorophenylamino)-2-methyl-N-(6H-pyrazolo[4',3':3,4]benzo[1,2-d]thiazol-2-yl)-propionamide, 2-[4-chloro-3-(2,3-dihydroxy-propoxy)-phenylamino]-2-methyl-N-(4-trifluoromethyl-6H-pyrazolo[4',3':3,4]benzo[1,2-d]thiazol-2-yl)-propionamide, 2-(3-methoxyphenylamino)-N-(6H-pyrazolo[4',3':3,4]benzo[1,2-d]thiazol-2-yl)-propionamide, 2-(4-chlorophenylamino)-2-methyl-N-(6H-pyrazolo[4',3':3,4]benzo[1,2-d]thiazol-2-yl)-propionamide, 2-(3-acetylamino-4-chlorophenylamino)-N-(6H-pyrazolo[4',3':3,4]benzo[1,2-d]thiazol-2-yl)-acetamide, 1-(3-acetylamino-4-fluorophenylamino)-N-(6H-pyrazolo[4',3':3,4]benzo[1,2-d]thiazol-2-yl)-cyclopropane-carboxamide, 2-chloro-N-methyl-5-[1-(6H-pyrazolo[4',3':3,4]benzo[1,2-d]thiazol-2-ylcarbamoyl)-cyclopropylamino]-benzamide, 2-chloro-N-methyl-5-[1-methyl-1-(4-trifluoromethyl-6H-pyrazolo[4',3':3,4]benzo[1,2-d]thiazol-2-ylcarbamoyl)-ethylamino]-benzamide, 2-chloro-N-ethyl-5-[1-methyl-1-(4-trifluoromethyl-6H-pyrazolo[4',3':3,4]benzo[1,2-d]thiazol-2-ylcarbamoyl)-ethylamino]-benzamide, 2-methyl-2-(3-sulfamoylphenylamino)-N-(4-trifluoro-methyl-6H-pyrazolo[4',3':3,4]benzo[1,2-d]thiazol-2-yl)-propionamide, N-carbamoylmethyl-2-chloro-5-[1-methyl-1-(4-trifluoromethyl-6H-pyrazolo[4',3':3,4]benzo[1,2-d]thiazol-2-ylcarbamoyl)-ethylamino]-benzamide, and 4-{2-chloro-5-[1-methyl-1-(4-trifluoromethyl-6H-pyrazolo[4',3':3,4]benzo[1,2-d]thiazol-2-ylcarbamoyl)-ethylamino]-benzoylamino}-butyric acid.

The following lists examples of most preferable compounds:

2-[4-chloro-3-(2,3-dihydroxy-propoxy)-phenylamino]-2-methyl-N-(4-trifluoromethyl-6H-pyrazolo[4',3':3,4]benzo[1,2-d]thiazol-2-yl)-propionamide, 2-(4-chlorophenylamino)-2-methyl-N-(6H-pyrazolo[4',3':3,4]benzo[1,2-d]thiazol-2-yl)-propionamide, 2-chloro-N-methyl-5-[1-(6H-pyrazolo[4',3':3,4]benzo[1,2-d]thiazol-2-ylcarbamoyl)-cyclopropylamino]-benzamide, and 2-chloro-N-methyl-5-[1-methyl-1-(4-trifluoromethyl-6H-pyrazolo[4',3':3,4]benzo[1,2-d]thiazol-2-ylcarbamoyl)-ethylamino]-benzamide.

The present invention provides a pharmaceutical composition or veterinary pharmaceutical composition comprising an effective amount of a compound of formula (1) for the treatment of these diseases.

In the case of a using a compound as claimed in the present invention as a therapeutic agent of those diseases, examples of the administration method thereof include oral, rectal, parenteral (intravenous, intramuscular or subcutaneous), intracisternal, intravaginal, intraperitoneal, intravesical and local (infusion, powder, ointment, gel or cream) administration, and inhalation (intraoral or nasal spray). Examples of dosage forms include tablets, capsules, granules, powders, grains, pills, aqueous or non-aqueous oral solutions, suspensions and parenteral solutions filled into containers suitable for packaging into individual doses. In addition, the dosage form can also be adapted to various administration methods including controlled-release preparations in the manner of subcutaneous implants.

A compound of formula (1) of the present invention, or a salt, prodrug or solvate thereof, can be administered orally or parenterally in the form of a pharmaceutical composition also comprising additives including pharmaceutically acceptable carriers such as an excipient, binder, diluent, stabilizer, lubricant, corrective, disintegration agent, coating agent, colorant, antioxidant, buffer, aqueous solvent, oily solvent, isotonic agent, dispersant, preservative, dissolving assistant, fluidizer, pain reliever, pH adjuster, antiseptic or base. Examples of oral preparations of the above pharmaceutical composition include granules, powders, tablets, hard capsules, soft capsules, syrups, emulsions and suspensions, while examples of parenteral preparations include injection preparations such as subcutaneous injection preparations, intravenous injection preparations, intramuscular injection preparations or intraperitoneal injection preparations; transcutaneous preparations such as ointments, creams or lotions; suppositories such as rectal suppositories or vaginal suppositories; and, transnasal preparations. These preparations can be produced according to known methods ordinarily used in formulation processes.

Examples of excipients used in a pharmaceutical composition of the present invention include sugars such as lactose, saccharose, glucose, D-mannitol or sorbitol; celluloses and derivatives thereof such as crystalline cellulose, hydroxypropyl cellulose, hydroxypropyl methylcellulose or methylcellulose; starches and derivatives thereof such as cornstarch, potato starch, α-starch, dextrin, β-cyclodextrin, sodium carboxymethyl starch or hydroxypropyl starch; silicates such as synthetic aluminum silicate, magnesium aluminosilicate, calcium silicate or magnesium silicate; phosphates such as calcium phosphate; carbonates such as calcium carbonate; sulfates such as calcium sulfate; and, tartaric acid, potassium hydrogen tartrate and magnesium hydroxide.

Examples of binders include agar, stearyl alcohol, gelatin, tragacanth, polyvinyl alcohol, polyvinyl pyrrolidone; celluloses and derivatives thereof such as crystalline cellulose, hydroxypropyl cellulose, hydroxypropyl methylcellulose or methylcellulose; starches and derivatives thereof such as cornstarch, potato starch, α-starch, dextrin, β-cyclodextrin, sodium carboxymethyl starch or hydroxypropyl starch; and sugars such as lactose, saccharose, glucose, D-mannitol or sorbitol.

Examples of stabilizers include hydrogenated oils, sesame oil, sodium chondroitin sulfate, dibutylhydroxytoluene, adipic acid, ascorbic acid, L-ascorbic acid, stearic acid ester, sodium L-ascorbate, L-aspartic acid, sodium L-aspartate, sodium acetyltryptophanate, acetanilide, aprotinin solution, aminoethyl sulfonate, aminoacetic acid, DL-alanine, L-alanine; parahydroxybenzoic esters such as methyl parahydroxybenzoate or propyl parahydroxybenzoate; alcohols such as chlorobutanol, benzyl alcohol or phenyl ethyl alcohol; benzalkonium chloride; phenols such as phenol or cresol; sorbic acid; sulfites such as sodium bisulfite or sodium sulfite; and, edetates such as sodium edetate or tetrasodium edetate.

Examples of lubricants include powdered gum arabic, cocoa butter, calcium carmellose, sodium carmellose, calopeptide, hydrated silicon dioxide, hydrated amorphous silicon oxide, dry aluminum hydroxide gel, glycerin, light liquid paraffin, crystalline cellulose, hydrogenated oil, synthetic aluminum silicate, sesame oil, wheat starch, talc, macrogols, phosphoric acid; stearic acids such as stearic acid, calcium stearate or magnesium stearate; waxes such as bleached beeswax or carnauba wax; sulfates such as sodium sulfate; silicates such as magnesium silicate or light silicic anhydride; and lauryl sulfates such as sodium lauryl sulfate.

Examples of correctives include ascorbic acid, L-aspartic acid, sodium L-aspartate, magnesium L-aspartate, aspartame, tea of heaven, tea of heaven extract, powdered tea of heaven, aminoethylphosphonate, aminoacetic acid, DL-alanine, sodium saccharin, dl-menthol, 1-menthols; and sugars such as lactose, saccharose, glucose or D-mannitol.

Examples of disintegration agents include agar, gelatin, tragacanth, adipic acid, alginic acid, sodium alginate; celluloses and derivatives thereof such as crystalline cellulose, hydroxypropyl cellulose, hydroxypropyl methylcellulose or methylcellulose; carbonates such as calcium carbonate, sodium bicarbonate or magnesium carbonate; and starches and derivatives thereof such as cornstarch, potato starch, α-starch, dextrin, β-cyclodextrin, sodium carboxymethyl starch or hydroxypropyl starch.

Examples of coating agents include shellac, polyvinyl pyrrolidones, polyethylene glycol, macrogols, methacrylic acid copolymers, liquid paraffin, Eudragit; and celluloses and cellulose derivative such as cellulose acetate, hydroxypropyl cellulose, cellulose acetate phthalate or hydroxypropyl methylcellulose.

Examples of colorants include indigo carmine, caramel and riboflavin.

Examples of buffers include aminoacetic acid, L-arginine, benzoic acid, sodium benzoate, aluminum chloride, potassium chloride, sodium chloride, dry sodium sulfite, dry sodium carbonate, dilute hydrochloric acid, citric acid, calcium citrate, sodium citrate, disodium citrate, calcium gluconate, L-glutamic acid, sodium L-glutamate, creatinine, chlorobutanol, crystalline sodium dihydrogen phosphate, disodium succinate, acetic acid, potassium acetate, sodium acetate, tartaric acid, sodium bicarbonate, sodium carbonate, triethanolamine, lactic acid, sodium acetate solution, glacial acetic acid, boric acid, maleic acid, anhydrous citric acid, anhydrous sodium citrate, anhydrous sodium acetate, anhydrous sodium carbonate, anhydrous sodium hydrogen phosphate, anhydrous trisodium phosphate, anhydrous sodium dihydrogen phosphate, dl-malic acid, phosphoric acid, trisodium phosphate, sodium hydrogen phosphate, dipotassium phosphate, potassium hydrogen phosphate, sodium dihydrogen phosphate and sodium dihydrogen phosphate monohydrate.

Examples of aqueous solvents include distilled water, physiological saline and Ringer's solution.

Examples of oily solvents include propylene glycol; and vegetable oils such as olive oil, sesame oil, cottonseed oil or corn oil.

Examples of isotonic agents include potassium chloride, sodium chloride, glycerin, sodium bromide, D-sorbitol, nicotinic amide, glucose and boric acid.

Examples of dispersants include gum arabic, propylene glycol alginic acid ester, sorbitan sesquioleate, D-sorbitol, tragacanth, methylcellulose, aluminum monostearate, aminoalkyl methacrylate copolymer RS, lactose, concentrated glycerin, propylene glycol, macrogols, sodium lauryl sulfate; and stearates such as zinc stearate or magnesium stearate and salts thereof.

Examples of preservatives include benzalkonium chloride, benzethonium chloride, dry sodium sulfite, dry sodium sulfate, sodium dehydroacetate, phenol, formalin, phosphoric acid, benzoin, thimerosal, thymol, sodium dehydroacetate; alcohols such as chlorobutanol, phenethyl alcohol, propylene glycol or benzyl alcohol; and parahydroxybenzoic esters such as isobutyl parahydroxybenzoate, ethyl parahydroxybenzoate or methyl parahydroxybenzoate.

Examples of dissolving assistants include sodium benzoate, ethylenediamine, citric acid, sodium citrate, glycerin, sodium acetate, sodium salicylate, sorbitan sesquioleate, nicotinic amide, glucose, benzyl alcohol, polyvinyl pyrrolidones, acetone, ethanol, isopropanol, D-sorbitol, sodium bicarbonate, sodium carbonate, lactose, urea and saccharose.

Examples of fluidizers include hydrated silicon dioxide, talc, anhydrous ethanol, crystalline cellulose, synthetic aluminum silicate, potassium hydrogen phosphate; and stearates such as calcium stearate or magnesium stearate and salts thereof.

Examples of pain relievers include benzalkonium chloride, procaine hydrochloride, meprylcaine hydrochloride, lidocaine hydrochloride and lidocaine.

Examples of pH adjusters include hydrochloric acid, citric acid, succinic acid, acetic acid, boric acid, maleic acid and sodium hydroxide.

Examples of antiseptics include benzoic acid, sodium benzoate, cetyl pyridinium chloride, salicylic acid, sodium salicylate, sorbic acid, potassium sorbate, thymol, methyl paraoxybenzoate and butyl paraoxybenzoate.

Examples of bases include glycerin, stearyl alcohol, polyethylene glycols, propylene glycol, cetanol, pork fat, white Vaseline, paraffin, bentonite, lanolin fatty acid isopropyl ester, Vaseline, polysorbates, macrogols, lauryl alcohol, sodium lauryl sulfate, ethyl linoleate, sodium hydrogen phosphate, rosin; and, vegetable oils such as olive oil, sesame oil or wheat germ oil.

Although varying according to the form thereof, the amount of compound of formula (1) contained in a pharmaceutical composition of the present invention is preferably about 0.1 to 100% by weight based on the total amount of the pharmaceutical composition. In addition, although variable over a broad range according to the type of administration control (such as warm-blooded animals including humans), type of disease to be treated, degree of symptoms, age, gender, administration method, physician's diagnosis and the like, the dosage of a pharmaceutical composition of the present invention in terms of, for example, the adult dosage of a compound of formula (1), is preferably about 0.1 to 2000 mg/kg per day for either oral or parenteral administration. Furthermore, the above dosage refers to the value per unit body weight of the administered subject. In addition, in the present invention, the above dosage may be administered in a single dose or may be divided among several doses for 1 to 7 days.

Example

In the following, the present inventions will be illustrated by Examples, but the present inventions are not limited to these Examples.

Synthesis Example

Reference Example A

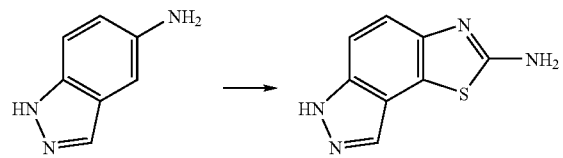

2.0 g (15 mmol) of 5-aminoindazole and 4.9 g (60.5 mmol) of sodium thiocyanate were suspended in 10 ml of acetic acid, and 2.4 g (15 mmol) of bromine was added dropwise to the suspension under ice-cooling. The reaction mixture was allowed to warm to room temperature, and it was stirred overnight. The reaction mixture was poured into water, and the resulting crystals were collected by filtration to give 3.1 g of 6H-pyrazolo[4',3':3,4]benzo[1,2-d]thiazol-2-ylamine.

MASS (ESI+) m/z=191 [M+H]$^+$ $^1$H-NMR (300 MHz, DMSO-d$_6$) δ (ppm) 8.07 (1H, s), 7.45 (1H, d, J=8.8 Hz), 7.36 (1H, d, J=9.0 Hz), 7.30 (2H, brs)

Reference Example B

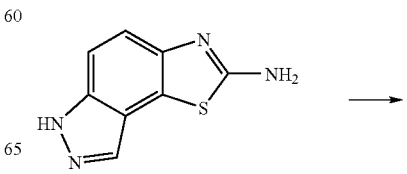

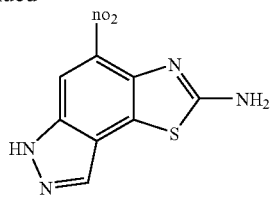

Under ice-cooling, 184 mg (2.17 mmol) of sodium nitrate was added to a mixture of 191 mg (1.01 mmol) of 6H-pyrazolo[4',3':3,4]benzo[1,2-d]thiazol-2-ylamine and 3 ml of concentrated sulfuric acid, and the mixture was stirred for 0.5 hours. The reaction mixture was poured onto ice, and the precipitated solid was collected by filtration, and then washed with water and methanol to give 160 mg (yield: 68%) of 4-nitro-6H-pyrazolo[4',3':3,4]benzo[1,2-d]thiazol-2-ylamine.

MASS (ESI+) m/z=236 (M+H)$^+$ $^1$H-NMR (300 MHz, DMSO-$d_6$) δ (ppm) 8.48 (1H, s), 8.26 (1H, s)

Reference Example C

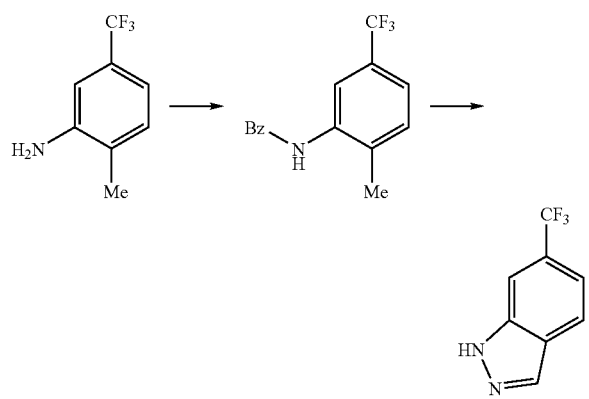

Under ice-cooling, 4.0 ml (34.5 mmol) of benzoyl chloride was added dropwise to a mixture of 4.97 g (28.8 mmol) of 3-amino-4-methyl-benzotrifluoride and 10 ml of pyridine. After stirring the mixture at room temperature for 1 hour, the solvent was removed under reduced pressure, and water was added to the residue. The precipitated solid was collected by filtration and then washed with water and a 50% aqueous methanol solution to give 8.04 g of 3-benzoylamino-4-methyl-benzotrifluoride.

A mixture of 8.04 g of 3-benzoylamino-4-methyl-benzotrifluoride, 40 ml of acetic acid and 20 ml of acetic anhydride was cooled with ice, and the mixture was stirred for 14 hours while bubbling through $N_2O_3$ gas, according to a method described in Organic Synthesis, vol. 42, page 69 (1962). After completion of the reaction was confirmed by HPLC, the reaction mixture was poured into 70 g of ice and 50 ml of water, the mixture was stirred under ice-cooling for 1 hour, and the mixture was filtered. The resulting solid was washed with water and dried under reduced pressure. Thereafter, 50 ml of benzene was added to the mixture and the mixture was stirred at room temperature for 24 hours. The reaction mixture was cooled with ice, 20 ml of 2M hydrochloric acid was added to the mixture to isolate the organic layer. Thereafter, the organic layer was extracted with 5M hydrochloric acid. Concentrated ammonia water was added to the combined aqueous layers until the pH reached 10 or higher. The precipitated solid was collected by filtration and then washed with water to give 1.18 g (yield: 22%, two steps) of 6-trifluoromethylindazole.

MASS (ESI+) m/z=187 (M+H)$^+$ $^1$H-NMR (300 MHz, CDCl$_3$) δ (ppm) 8.19 (1H, s), 7.90 (1H, d, J=8.5 Hz), 7.84 (1H, s), 7.42 (1H, d, J=8.5 Hz), 7.30 (2H, brs)

Reference Example D

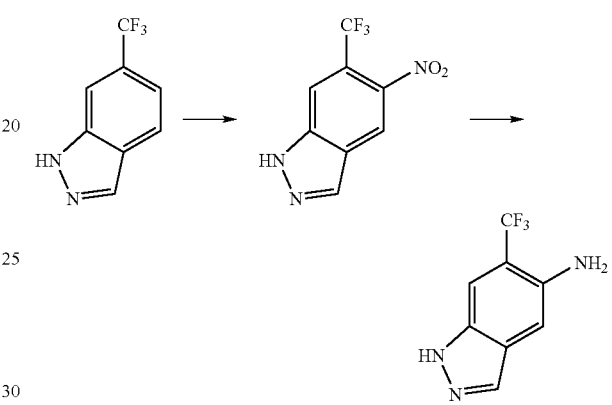

Under ice-cooling, 1.01 g (12.0 mmol) of sodium nitrate was added to a mixture of 1.54 g (8.29 mmol) of 6-trifluoromethylindazole and 5 ml of concentrated sulfuric acid, and the mixture was stirred for 1 hour. The reaction mixture was poured onto ice and after ammonia water was added dropwise to the mixture under ice-cooling until pH reached 10 or higher, the precipitated solid was collected by filtration and then washed with water, followed by drying. The resulting crude product was dissolved in 50 ml of methanol, activated carbon was added to the mixture, and the mixture was filtered. 0.20 g of 5% Palladium-on-carbon was added to the filtrate, and the mixture was stirred under a hydrogen atmosphere at room temperature for 14 hours. The mixture was filtered through Celite and the filtrate was concentrated under reduced pressure to give 1.57 g (yield: 94%, two steps) of 5-amino-6-trifluoromethylindazole.

MASS (ESI+) m/z=202 (M+H)$^+$ $^1$H-NMR (300 MHz, CD$_3$OD) δ (ppm) 7.89 (1H, s), 7.72 (1H, s), 7.20 (1H, s)

Reference Example E

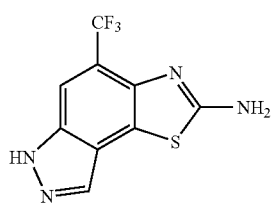

4-Trifluoromethyl-6H-pyrazolo[4',3':3,4]benzo[1,2-d]thiazol-2-ylamine was synthesized from 5-amino-6-trifluoromethylindazole according to the synthesis method described in Reference example A (yield: 88%).

MASS (ESI+) m/z=259 (M+H)+

$^1$H-NMR (300 MHz, DMSO-$d_6$) δ (ppm) 8.24 (1H, s), 7.78 (1H, s), 7.73 (2H, s)

Reference Example F

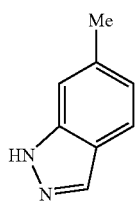

6-Methylindazole was synthesized from 2,5-dimethylaniline according to the synthesis method described in Reference example C (yield: 30%, two steps).

MASS (ESI+) m/z=133 (M+H)+

$^1$H-NMR (300 MHz, CDCl$_3$) δ (ppm) 8.02 (1H, s), 7.64 (1H, d, J=8.2 Hz), 7.28 (1H, s), 7.01 (1H, d, J=8.2 Hz), 2.49 (3H, s)

Reference Example G

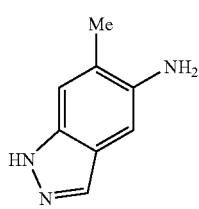

5-Amino-6-methylindazole was synthesized from 6-methylindazole according to the synthesis method described in Reference example D (yield: 89%, two steps).

MASS (ESI+) m/z=148 (M+H)+

Reference Example H

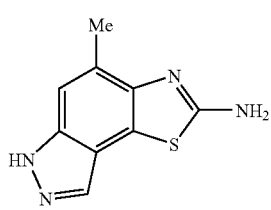

4-Methyl-6H-pyrazolo[4',3':3,4]benzo[1,2-d]thiazol-2-ylamine was synthesized from 5-amino-6-methylindazole according to the synthesis method described in Reference example A (yield: 79%).

MASS (ESI+) m/z=205 (M+H)+

$^1$H-NMR (300 MHz, DMSO-$d_6$) δ (ppm) 7.97 (1H, s), 7.32 (1H, s) 7.23 (1H, s), 2.57 (3H, s)

Reference Example I

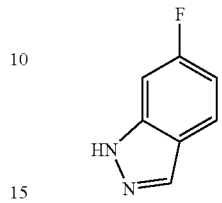

6-Fluoroindazole was synthesized from 5-fluoro-2-methylaniline according to the synthesis method described in Reference example C (yield: 27%, two steps).

MASS (ESI+) m/z=137 (M+H)+

$^1$H-NMR (300 MHz, CDCl$_3$) δ (ppm) 8.09 (1H, s), 7.71 (1H, dd, J=8.8, 5.2 Hz), 7.16 (1H, brd, J=8.5 Hz), 6.96 (1H, td, J=8.8, 1.8 Hz)

Reference Example J

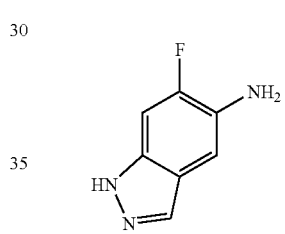

5-Amino-6-fluoroindazole was synthesized from 6-fluoroindazole using concentrated nitric acid instead of sodium nitrate according to the synthesis method described in Reference example D (yield: 93%, two steps).

MASS (ESI+) m/z=152 (M+H)+

Reference Example K

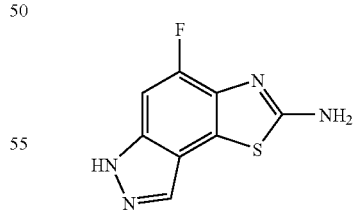

4-Flucro-6H-pyrazolo[4',3':3,4]benzo[1,2-d]thiazol-2-ylamine was synthesized from 5-amino-6-fluoroindazole according to the synthesis method described in Reference example A (yield: 26%)

MASS (ESI+) m/z=209 (M+H)+

$^1$H-NMR (300 MHz, DMSO-$d_6$) δ (ppm) 8.09 (1H, s), 7.54 (2H, s), 7.26 (1H, d, J=10.7 Hz)

Reference Example L

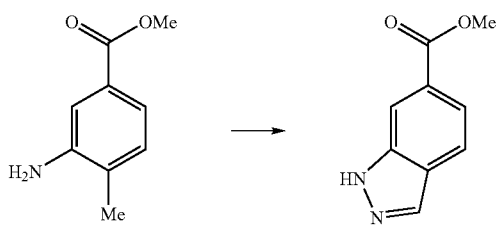

2.47 g (34.5 mmol) of sodium nitrite was dissolved in 3.8 ml of water, and it was added dropwise to a mixture of 5.64 g (34.1 mmol) of methyl 3-amino-4-methyl-benzoate and 140 ml of acetic acid under ice-cooling. After the temperature of the reaction mixture was allowed to warm to room temperature and the mixture was stirred overnight, water was added to the mixture and the mixture was extracted with ethyl acetate. The organic layer was washed with water and brine, and then dried over magnesium sulfate and filtered. The solvent was distilled off to give 4.83 g (yield: 80%) of methyl indazole-6-carboxylate.

MASS (ESI+) m/z=177 (M+H)$^+$

Reference Example M

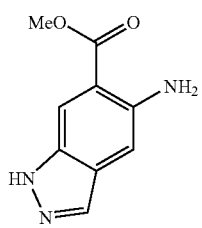

Methyl 5-aminoindazole-6-carboxylate was synthesized from methyl indazole-6-carboxylate using concentrated nitric acid instead of sodium nitrate according to the synthesis method described in Reference example D (yield: 92%, two steps).

MASS (ESI+) m/z=192 (M+H)$^+$, 160

$^1$H-NMR (400 MHz, DMSO-d$_6$) δ (ppm) 8.00 (1H, s), 7.85 (1H, s), 6.99 (1H, s), 6.03 (2H, brs), 3.85 (3H, s)

Reference Example N

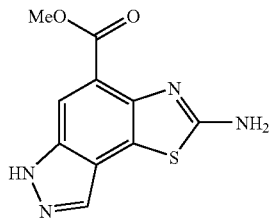

Methyl 2-amino-6H-pyrazolo[4',3':3,4]benzo[1,2-d]thiazol-4-carboxylate was synthesized from methyl 5-aminoindazole-6-carboxylate according to the synthesis method described in Reference example A (yield: 30%).

MASS (ESI+) m/z=249 (M+H)$^+$ $^1$H-NMR (300 MHz, DMSO-d$_6$) δ (ppm) 8.18 (1H, s), 7.85 (1H, s), 7.68 (2H, brs), 3.86 (3H, s)

Reference Example P

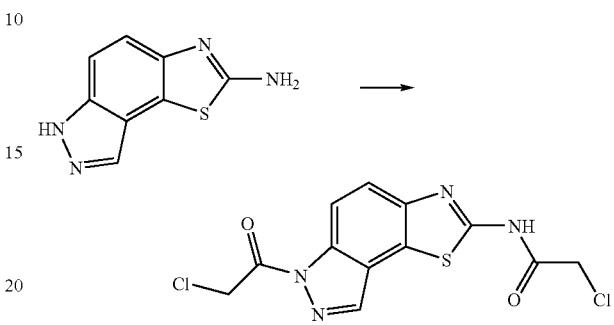

0.5 g (2.6 mmol) of 6H-pyrazolo[4',3':3,4]benzo[1,2-d]thiazol-2-ylamine and 0.36 g (3.2 mmol) of chloroacetyl chloride were dissolved in 5 ml of tetrahydrofuran, and 0.4 g (4.0 mmol) of triethylamine was added dropwise to the mixture under ice-cooling. After the mixture was allowed to warm to room temperature and was stirred overnight, 4 ml of water was added to the mixture to quench the reaction. The reaction mixture was extracted with 4 ml of ethyl acetate twice, dried over 3 g of anhydrous magnesium sulfate, and then concentrated under reduced pressure. The crude product was purified by silica gel column chromatography (hexan/ethyl acetate=1/1) to give 0.3 g (yield: 33%) of 2-chloro-N-[6-(2-chloroacetyl)-6H-pyrazolo[4',3':3,4]benzo[1,2-d]thiazol-2-yl]-acetamide as an intermediate.

MASS (ESI+) m/z=343, 345, 347 [M+H]$^+$

Reference Example Q

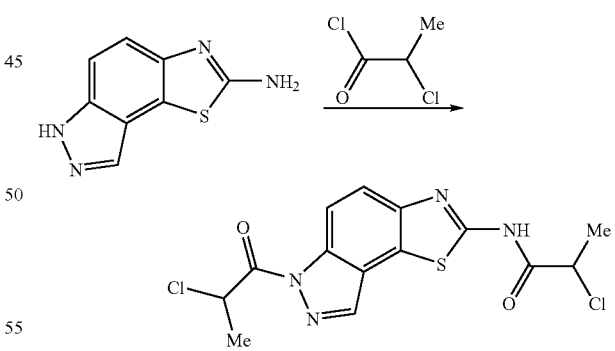

0.49 g (2.6 mmol) of 6H-pyrazolo[4',3':3,4]benzo[1,2-d]thiazol-2-yl-amine and 0.33 g (2.6 mmol) of 2-chloropropionyl chloride were dissolved in 5 ml of tetrahydrofuran, and 0.39 g (4.0 mmol) of triethylamine was added dropwise to the mixture under ice-cooling. After the mixture was allowed to warm to room temperature and was stirred overnight, 4 ml of water was added to the mixture to quench the reaction. The mixture was extracted with 4 ml of ethyl acetate twice, dried over 3 g of anhydrous magnesium sulfate, and then concentrated under reduced pressure. The crude product was purified by silica gel column chromatography (hexane/ethyl acetate=1/1) to give 0.37 g (yield: 38.7%) of 2-chloro-N-[6-(2-chloropropionyl)-6H-pyrazolo[4',3':3,4]benzo[1,2-d]thiazol-2-yl]-propionamide.

MASS (ESI+) m/z=370, 372, 374 [M+H]+

Reference Example R

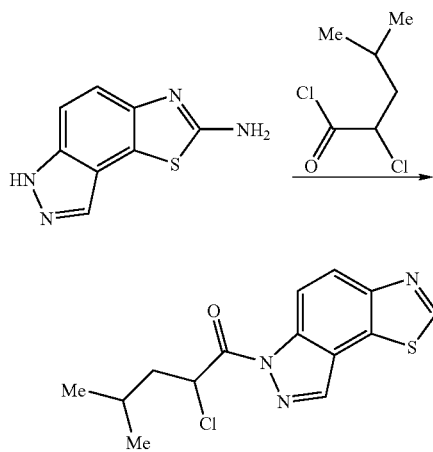

1.0 g (6.7 mmol) of 2-chloro-4-methyl-n-valeric acid was reacted with 2.5 ml (34 mmol) of thionyl chloride under refluxing of 5 ml of toluene to prepare the corresponding acid chloride. After the solvent was distilled off under reduced pressure, 1.3 g (6.8 mmol) of 6H-pyrazolo[4',3':3,4]benzo[1,2-d]thiazol-2-ylamine and 10 ml of tetrahydrofuran were added to the mixture, 1.0 g (9.9 mmol) of triethylamine was added dropwise to the mixture under ice-cooling. After the mixture was allowed to warm to room temperature and was stirred overnight, 10 ml of water was added to the mixture to quench the reaction. The mixture was extracted with 20 ml of ethyl acetate twice, dried over 5 g of anhydrous magnesium sulfate, and then concentrated under reduced pressure. The crude product was purified by silica gel column chromatography (hexane/ethyl acetate=1/1) to give 0.42 g (yield: 13.5%) of 2-chloro-4-methyl-valeric acid [6-(2-chloro-4-methyl-pentanoyl)-6H-pyrazolo[4',3':3,4]benzo[1,2-d]thiazol-2-yl]amide.

MASS (ESI+) m/z=454, 456, 457 [M+H]+

Reference Example S

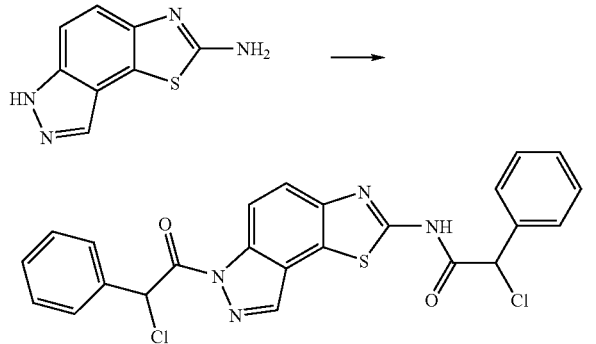

0.50 g (2.6 mmol) of 6H-pyrazolo[4',3':3,4]benzo[1,2-d]thiazol-2-ylamine and 1.5 g (7.9 mmol) of α-chlorophenylacetyl chloride were dissolved in 10 ml of tetrahydrofuran, and 1.3 g (12.9 mmol) of triethylamine was added dropwise to the mixture under ice-cooling. After the mixture was allowed to warm to room temperature and was stirred overnight, 10 ml of water was added to the mixture to quench the reaction. The reaction mixture was extracted with 20 ml of ethyl acetate twice, dried over 5 g of anhydrous magnesium sulfate, and then concentrated under reduced pressure. The crude product was purified by silica gel column chromatography (hexane/ethyl acetate=1/1) to give 1.3 g (yield: 100%) of 2-chloro-N-[6-(2-chloro-2-phenylacetyl)-6H-pyrazolo[4',3':3,4]benzo[1,2-d]thiazol-2-yl]-2-phenylacetamide.

Reference Example T

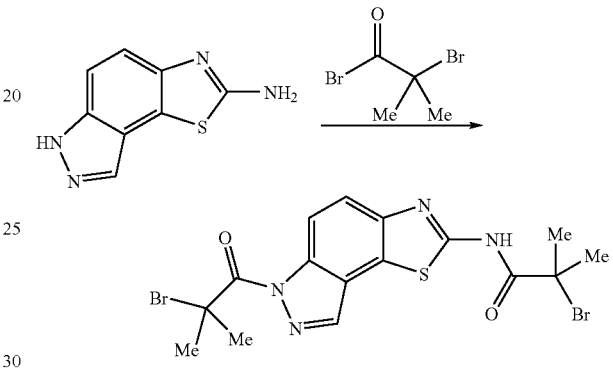

0.50 g (2.6 mmol) of 6H-pyrazolo[4',3':3,4]benzo[1,2-d]thiazol-2-ylamine and 1.82 g (7.9 mmol) of bromoisobutyryl bromide were dissolved in 5 ml of tetrahydrofuran, and 1.1 g (10.9 mmol) of triethylamine was added dropwise to the mixture under ice-cooling. After the mixture was allowed to warm to room temperature and was stirred overnight, 4 ml of water was added to the mixture to quench the reaction. The reaction mixture was extracted with 4 ml of ethyl acetate twice, dried over 3 g of anhydrous magnesium sulfate, and then concentrated under reduced pressure. The crude product was washed with methanol to give 0.43 g (yield: 33%) of 2-bromo-N-[6-(2-bromo-2-methyl-propionyl)-6H-pyrazolo[4',3':3,4]benzo[1,2-d]thiazol-2-yl]-2-methyl propionamide.

MASS (ESI+) m/z=487, 489, 491 [M+H]+

Reference Example U

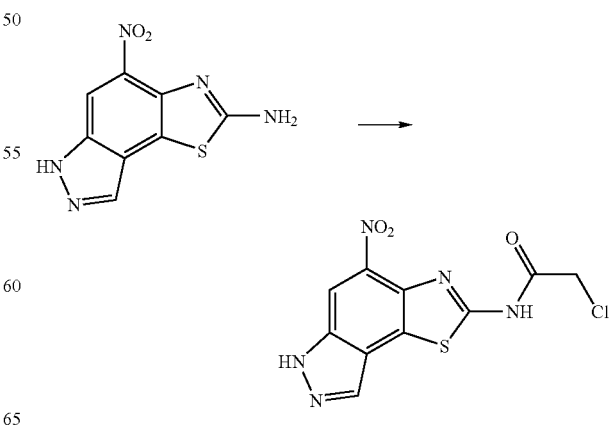

0.45 ml (3.23 mmol) of triethylamine was added dropwise to a mixture of 0.15 g (0.65 mmol) of 4-nitro-6H-pyrazolo[4', 3':3,4]benzo[1,2-d]thiazol-2-ylamine, 0.15 ml (1.88 mmol) of chloroacetyl chloride and 8 ml of tetrahydrofuran under ice-cooling. The mixture was stirred at 70° C. overnight and after the completion of the reaction was confirmed by HPLC, it was cooled to room temperature, and water was added to the mixture. The precipitated solid was washed with water and methanol to give 0.15 g (yield: 73%) of chloro-N-4-nitro-6H-pyrazolo[4',3':3,4]benzo[1,2-d]thiazol-2-yl)-acetamide.

MASS (ESI+) m/z=312, 314 (M+H)$^+$

Reference Example V

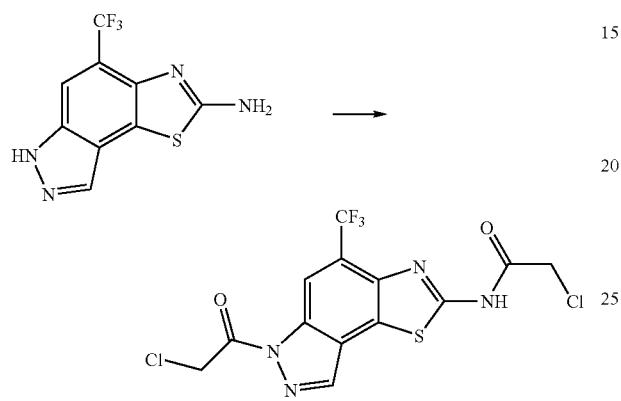

A mixture of 0.26 g (1.00 mmol) of 4-trifluoromethyl-6H-pyrazolo[4',3':3,4]benzo[1,2-d]thiazol-2-ylamine, 1.0 ml (12.6 mmol) of chloroacetyl chloride and 4 ml of 1,4-dioxane was heated under reflux for 3 hours. After the completion of the reaction was confirmed by HPLC, the reaction mixture was cooled to room temperature and poured into ice-water. The precipitated solid was collected by filtration and was washed with water to give 0.34 g (yield: 77%) of 2-chloro-N-[6-(2-chloro-acetyl)-4-trifluoromethyl-6H-pyrazolo[4',3':3,4]benzo[1,2-d]thiazol-2-yl]-acetamide.

MASS (ESI+) m/z=411, 413, 415 (M+H)$^+$

Reference Example W

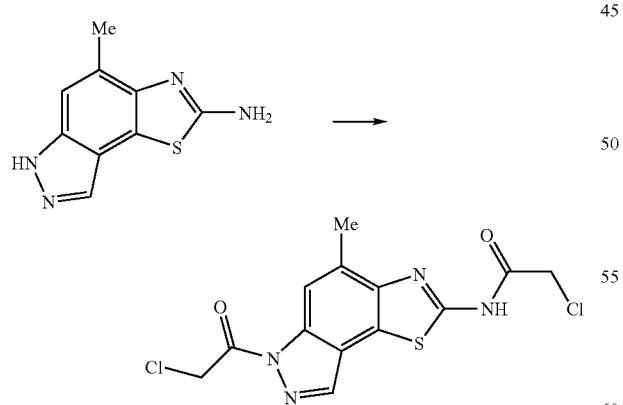

2-chloro-N-[6-(2-chloro-acetyl)-4-methyl-6H-pyrazolo[4',3':3,4]benzo[1,2-d]thiazol-2-yl]-acetamide was synthesized from 4-methyl-6H-pyrazolo[4',3':3,4]benzo[1,2-d]thiazol-2-ylamine according to the synthesis method described in Reference example U (yield: 90%).

MASS (ESI+) m/z=357, 359, 361 (M+H)$^+$

Reference Example X

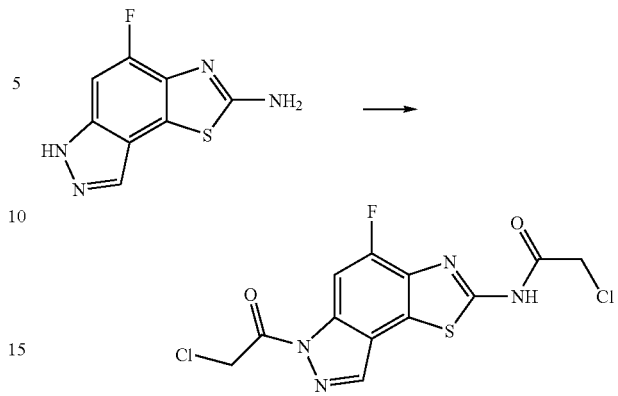

2-chloro-N-[6-(2-chloro-acetyl)-4-fluoro-6H-pyrazolo[4',3':3,4]benzo[1,2-d]thiazol-2-yl]-acetamide was synthesized from 4-fluoro-6H-pyrazolo[4',3':3,4]benzo[1,2-d]thiazol-2-ylamine according to the synthesis method described in Reference example U.

MASS (ESI+) m/z=361, 363, 365 (M+H)$^+$

Reference Example Y

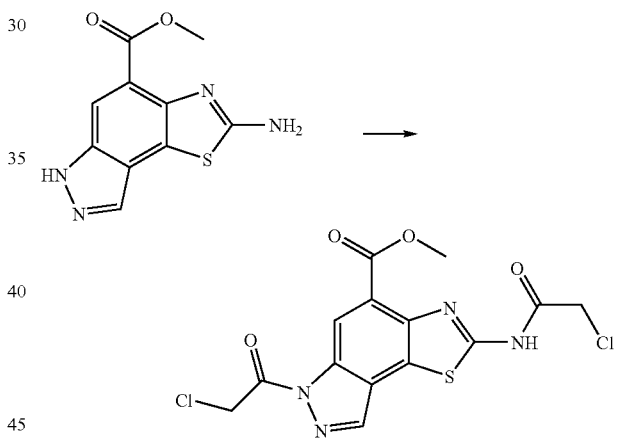

Methyl 6-(2-chloro-acetyl)-2-(2-chloro-acetylamino)-6H-pyrazolo[4',3':3,4]benzo[1,2-d]thiazole-4-carboxylate was synthesized from methyl 2-amino-6H-pyrazolo[4',3':3,4]benzo[1,2-d]thiazole-4-carboxylate according to the synthesis method described in Reference example U (yield: 83%).

MASS (ESI+) m/z=401, 403, 405 (M+H)$^+$

Reference Example Z

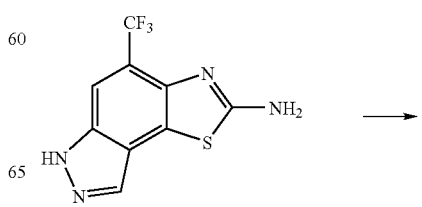

-continued

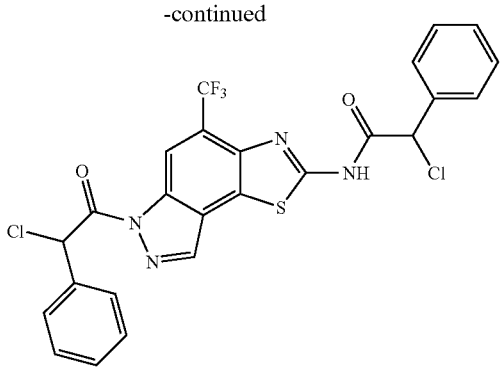

A mixture of 1.01 g (3.91 mmol) of 4-trifluoromethyl-6H-pyrazolo[4',3':3,4]benzo[1,2-d]thiazol-2-ylamine, 2.21 g (11.7 mmol) of chlorophenylacetyl chloride and 30 ml of 1,4-dioxane was heated under reflux for 3 hours. After the completion of the reaction was confirmed by HPLC, the reaction mixture was cooled to room temperature and was poured into ice-water. A saturated aqueous sodium hydrogen carbonate solution and ethyl acetate were added to the mixture and after the mixture was stirred, two layers were separated. The aqueous layer was extracted with ethyl acetate, the combined organic layers were washed with water and brine, and dried over magnesium sulfate, followed by filtration and concentration. The resulting crude product was purified by silica gel chromatography (hexane/ethyl acetate=10/1-2/1) to give 2.15 g (yield: 98%) of 2-chloro-N-[6-(2-chloro-2-phenylacetyl)-4-trifluoromethyl-6H-pyrazolo[4',3':3,4]benzo[1,2-d]thiazol-2-yl]-2-phenylacetamide.

MASS (ESI+) m/z=563, 565, 567 [M+H]+

Reference Example AA

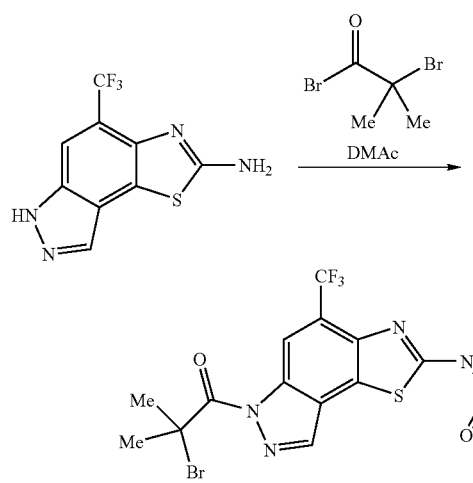

To a mixture of 5.6 g of 4-trifluoromethyl-6H-pyrazolo[4',3':3,4]benzo[1,2-d]thiazol-2-ylamine and 50 ml of dimethylacetamide was added dropwise 8.1 ml of 2-bromoisobutyryl bromide, and the mixture was heated at 40° C. for 2 hours. After the completion of the reaction was confirmed by HPLC, 150 ml of water was added to the mixture under ice-cooling, and the mixture was filtered. The solid collected by filtration was washed with water and methanol to give 10.7 g (yield: 88%) of 2-bromo-N-[6-(2-bromo-2-methyl-propionyl)-4-trifluoromethyl-6H-pyrazolo[4',3':3,4]benzo[1,2-d]thiazol-2-yl]-2-methyl-propionamide as a pale yellow solid.

MASS (ESI+) m/z=555, 557, 559 [M+H]+

$^1$H-NMR (300 MHz, CDCl$_3$) δ (ppm) 8.94 (1H, s), 8.40 (1H, s), 2.33 (6H, s), 2.12 (6H, s)

Reference Example AB

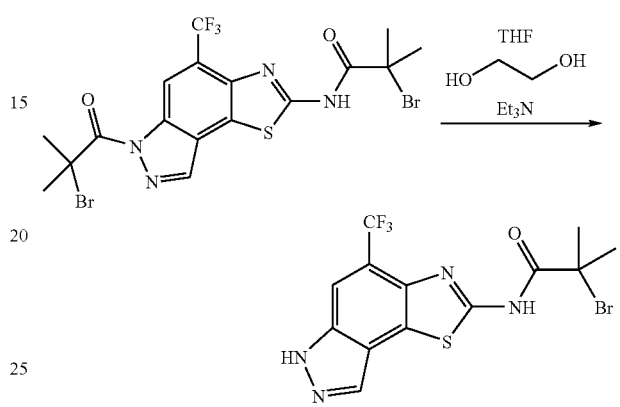

A mixture of 4.32 g of 2-bromo-N-[6-(2-bromo-2-methyl-propionyl)-4-trifluoromethyl-6H-pyrazolo[4',3':3,4]benzo[1,2-d]thiazol-2-yl]-2-methyl-propionamide, 25 ml of tetrahydrofuran, 10 ml of ethyleneglycol and 1.30 ml of triethylamine was stirred at room temperature for 14 hours. After the completion of the reaction was confirmed by HPLC, water and ethyl acetate were added and then portioned. The ethyl acetate layer was washed with 1M hydrochoric acid, water and brine and dried over magnesium sulfate, filtered, and then concentrated to dryness under reduced pressure. Hexane was added to the residue and the solid was collected by filtration to give 2.87 g (yield: 91%) of 2-bromo-2-methyl-N-(4-trifluoromethyl-6H-pyrazolo[4',3':3,4]benzo[1,2-d]thiazol-2-yl)-propionamide as a pale yellow solid.

MASS (ESI+) m/z=407, 409 [M+H]+

$^1$H-NMR (300 MHz, DMSO-d$_6$) δ (ppm) 8.53 (1H, s), 8.04 (1H, s), 2.10 (6H, s)

Synthesis Example 1

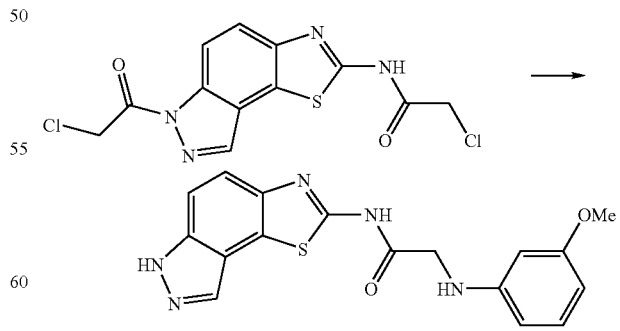

0.15 g (0.56 mmol) of 2-chloro-N-[6-(2-chloro-acetyl)-6H-pyrazolo[4',3':3,4]benzo[1,2-d]thiazol-2-yl]-acetamide, 0.2 g (1.63 mmol) of m-anisidine and 0.1 g (0.67 mmol) of sodium iodide were heated under reflux in 4 ml of n-propanol.

After the completion of the reaction was confirmed by HPLC, 4 ml of water and 4 ml of ethyl acetate were added to the mixture, and then portioned to isolate the organic layer. After 1 g of magnesium sulfate was added to dry it, it was concentrated under reduced pressure. The crude product was purified by silica gel column chromatography (hexane/ethyl acetate=1/1) to give 3.77 mg (yield: 1.9%) of the desired compound.

MASS (ESI+) m/z=354 [M+H]$^+$, 231, 191

$^1$H-NMR (300 MHz, DMSO-d$_6$) δ (ppm) 12.43 (1H, brs), 8.31 (1H, s), 7.75 (2H, d, J=8.7 Hz), 7.61 (2H, d, J=9.0 Hz), 7.00 (1H, dd, J=8.7, 8.1 Hz), 6.18-6.23 (4H, m), 4.08 (2H, d, J=3 Hz), 3.66 (3H, s)

The following compounds were obtained by the similar process using the corresponding aniline.

Synthesis Example 2

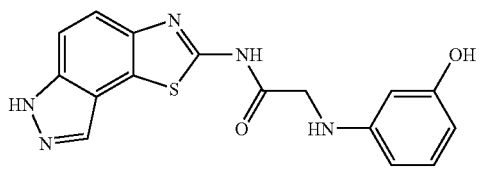

Yield: 2.2%
MASS (ESI+) m/z=340 [M+H]$^+$, 232, 191, 122
$^1$H-NMR (300 MHz, DMSO-d$_6$) δ (ppm) 12.38 (1H, brs), 9.02 (1H, brs), 7.75 (1H, d, J=8.7 Hz), 7.61 (1H, d, J=8.7 Hz), 6.87 (1H, dd, J=7.8, 8.4 Hz), 6.01-6.09 (4H, m), 4.03 (2H, d, J=6.6 Hz)

Synthesis Example 3

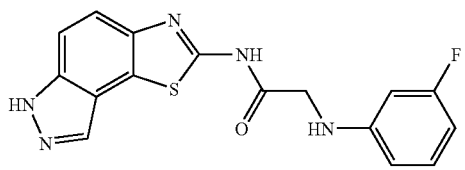

Yield: 2.3%
MASS (ESI+) m/z=342 [M+H]$^+$, 231, 191
$^1$H-NMR (300 MHz, DMSO-d$_6$) δ (ppm) 12.48 (1H, brs), 8.32 (1H, d, J=1.2 Hz), 7.75 (1H, d, J=8.7 Hz), 7.62 (1H, d, J=8.7 Hz), 7.07-7.15 (1H, m), 6.33-6.47 (4H, m), 4.21 (2H, s)

Synthesis Example 4

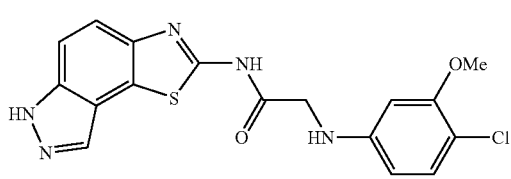

Yield: 1.4%
MASS (ESI+) m/z=388[M+H]$^+$, 295, 191
$^1$H-NMR (300 MHz, DMSO-d$_6$) δ (ppm) 12.48 (1H, brs), 8.32 (1H, s), 7.76 (1H, d, J=9.0 Hz), 7.62 (1H, d, J=9.0 Hz), 7.10 (1H, d, J=8.7 Hz), 6.45 (1H, d, J=2.4 Hz), 6.34 (1H, t, J=6.6 Hz), 6.18 (1H, dd, J=8.7, 2.4 Hz), 4.13 (2H, d, J=6.0 Hz), 3.78 (3H, s)

Synthesis Example 5

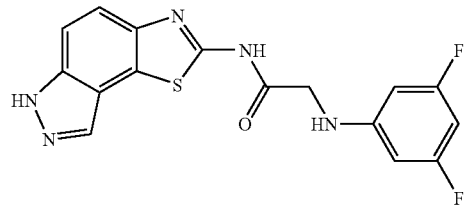

Yield: 0.9%
MASS (ESI+) m/z=360 [M+H]$^+$, 295, 191

Synthesis Example 6

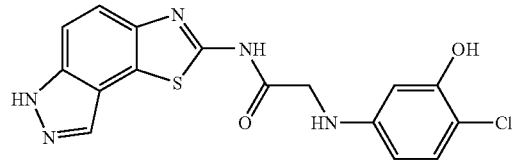

Yield: 0.8%
MASS (ESI+) m/z=374 [M+H]$^+$, 294, 191
$^1$H-NMR (300 MHz, DMSO-d$_6$) δ (ppm) 12.43 (1H, s), 9.72 (1H, s), 8.32 (1H, s), 7.75 (1H, d, J=9.0 Hz), 7.62 (1H, d, J=9.0 Hz), 7.00 (1H, d, J=8.4 Hz), 6.23 (1H, d, J=2.7 Hz), 6.11 (1H, dd, J=9.0, 2.7 Hz), 4.04 (2H, s), 3.48 (1H, brs)

Synthesis Example 7

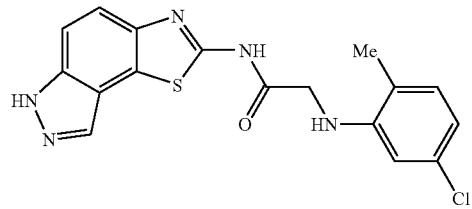

Yield: 3.2%
MASS (ESI+) m/z=372 [M+H]$^+$, 191

Synthesis Example 8

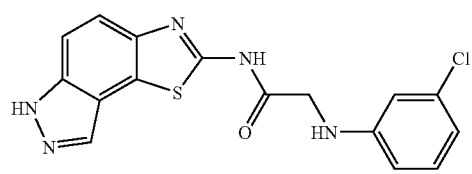

Yield: 1.6%
MASS (ESI+) m/z=358 [M+H]$^+$, 231, 191
$^1$H-NMR (300 MHz, DMSO-d$_6$) δ (ppm) 8.42 (1H, s), 7.86 (1H, d, 8.7 Hz), 7.72 (1H, d, J=9.0 Hz), 7.21 (1H, dd, J=8.1, 7.8 Hz), 6.77 (1H, s), 6.69 (2H, dd, J=6.9, 7.8 Hz), 6.59 (1H, t, J=6.6 Hz), 4.23 (2H, d, J=6.3 Hz)

Synthesis Example 9

Yield: 1.6%

MASS (ESI+) m/z=358 [M+H]$^+$, 231, 191

$^1$H-NMR (300 MHz, DMSO-d$_6$) δ (ppm) 12.45 (1H, s), 8.30 (1H, s), 7.74 (1H, d, J=8.7 Hz), 7.60 (1H, d, J=8.7 Hz), 7.12 (2H, d, J=9.0 Hz), 6.62 (2H, d, J=8.7 Hz), 6.34 (1H, m), 4.09 (2H, d, J=6.3 Hz)

Synthesis Example 10

Yield: 20%

MASS (ESI+) m/z=396 [M+H]$^+$

Synthesis Example 11

Yield: 4%

MASS (ESI+) m/z=339 [M+H]$^+$, 191

Synthesis Example 12

Yield: 2%

$^1$H-NMR (300 MHz, DMSO-d$_6$) δ (ppm) 8.24 (1H, s), 7.84 (1H, d, J=8.0 Hz), 7.62 (1H, d, J=8.0 Hz), 7.43 (1H, t, J=8.0 Hz), 7.12-7.26 (3H, m), 6.84 (1H, brd, J=8.0 Hz), 6.34 (1H, brt, J=5.8 Hz), 3.93 (2H, brd, J=5.8 Hz)

Synthesis Example 13

Yield: 2.2%

MASS (ESI+) m/z=364 [M+H]$^+$, 224, 191, 146

$^1$H-NMR (300 MHz, DMSO-d$_6$) δ (ppm) 8.30 (1H, s), 7.78 (1H, s), 7.74 (1H, d, J=9.5 Hz), 7.62 (2H, d, J=9.5 Hz), 7.32 (1H, d, J=9.0 Hz), 6.94 (1H, d, J=9.0 Hz), 6.64 (1H, s), 4.11 (2H, s)

Synthesis Example 14

Yield: 1%

MASS (ESI+) m/z=417 [M+H]$^+$ $^1$H-NMR (300 MHz, DMSO-d$_6$) δ (ppm) 9.51 (1H, s), 8.31 (1H, s), 7.74 (1H, d, J=8.8 Hz), 7.60 (1H, d, J=8.8 Hz), 7.03 (1H, t, J=8.0 Hz), 6.50 (1H, brs), 6.44 (1H, d, J=8.0 Hz), 6.35 (1H, d, J=8.0 Hz), 6.27 (1H, t, J=6.1 Hz), 4.07 (2H, brd, J=6.1 Hz), 3.04 (3H, s)

Synthesis Example 15

Yield: 3%

MASS (ESI+) m/z=364 [M+H]$^+$ $^1$H-NMR (300 MHz, DMSO-d$_6$) δ (ppm) 8.33 (1H, s), 7.76 (1H, s), 7.74 (1H, d, J=9.0 Hz), 7.61 (1H, d, J=9.0 Hz), 7.45 (1H, d, J=9.0 Hz), 6.65 (1H, dd, J=9.0, 1.0 Hz), 6.45-6.35 (2H, m), 4.15 (2H, brd, J=6.1 Hz)

Synthesis Example 16

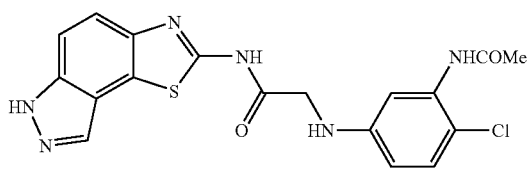

Yield: 3%
MASS (ESI+) m/z=415, 417 [M+H]+
1H-NMR (300 MHz, DMSO-d$_6$) δ (ppm) 9.26 (1H, s), 8.30 (1H, s), 7.74 (1H, d, J=8.8 Hz), 7.63 (1H, d, J=8.8 Hz), 7.16 (1H, d, J=8.8 Hz), 7.04 (1H, brs), 6.48-6.31 (2H, m), 4.08 (2H, d, J=6.1 Hz), 2.04 (3H, s)

Synthesis Example 17

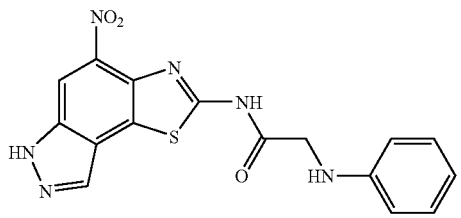

Yield: 4%
MASS (ESI+) m/z=369 [M+H]+

Synthesis Example 18

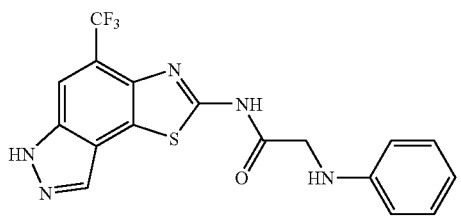

Yield: 77%
MASS (ESI+) m/z=392 [M+H]+
1H-NMR (300 MHz, DMSO-d$_6$) δ (ppm) 8.51 (1H, s), 8.02 (1H, s), 7.10 (1H, t, J=8.0 Hz), 6.65-6.53 (3H, m), 4.13 (2H, s)

Synthesis Example 19

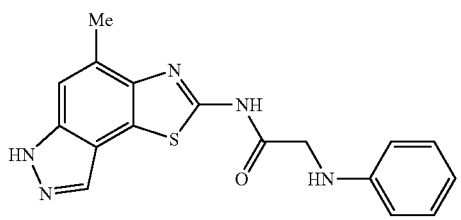

Yield: 7%
MASS (ESI+) m/z=338 [M+H]+
1H-NMR (300 MHz, DMSO-d$_6$) δ (ppm) 8.22 (1H, s), 7.42 (1H, s), 7.10 (2H, t, J=8.0 Hz), 6.65-6.53 (3H, m), 4.08 (2H, d, J=6.3 Hz), 2.67 (3H, s)

Synthesis Example 20

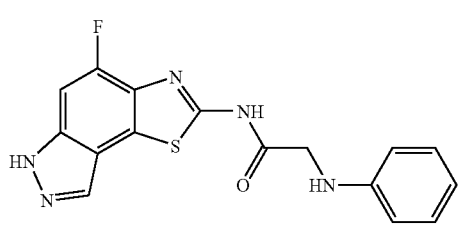

Yield: 52%
MASS (ESI+) m/z=342 [M+H]+
1H-NMR (300 MHz, DMSO-d$_6$) δ (ppm) 8.40 (1H, s), 7.47 (1H, d, J=11.6 Hz), 7.10 (2H, t, J=7.5 Hz), 6.64-6.53 (3H, m), 4.10 (2H, s)

Synthesis Example 21

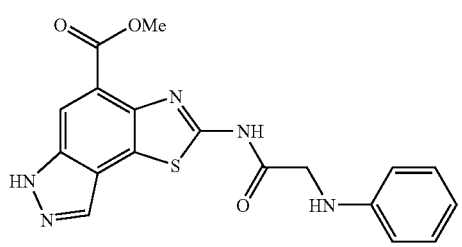

Yield: 7%
MASS (ESI+) m/z=382 [M+H]+
1H-NMR (300 MHz, DMSO-d$_6$) δ (ppm) 8.44 (1H, s), 8.06 (1H, s), 7.09 (2H, t, J=8.0 Hz), 6.66-6.53 (3H, m), 4.11 (2H, s), 3.92 (3H, s)

Synthesis Example 22

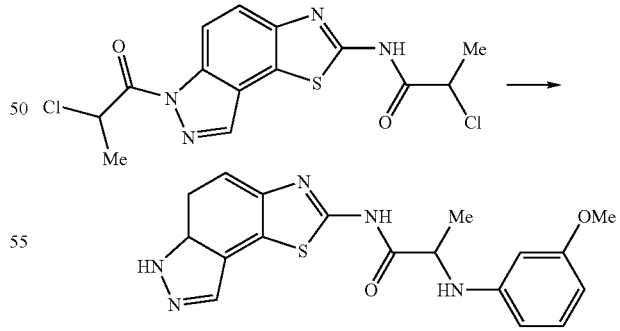

The desired compound was obtained by carrying out the similar procedures to Synthesis example 1 from 0.15 g (0.40 mmol) of 2-chloro-N-[6-(2-chloropropionyl)-6H-pyrazolo[4',3':3,4]benzo[1,2-d]thiazol-2-yl]-propionamide and 0.26 g (2.4 mmol) of m-anisidine.
Yield: 2.8%
MASS (ESI+) m/z=368 [M+H]+, 191, 150

¹H-NMR (300 MHz, DMSO-d₆) δ (ppm) 8.31 (1H, s), 7.75 (1H, d, J=9.0 Hz), 7.61 (1H, d, J=8.7 Hz), 6.98 (1H, dd, J=7.8, 7.8 Hz), 6.09-6.24 (4H, m), 4.28 (1H, m), 3.65 (3H, s), 1.45 (3H, d, J=6.6 Hz)

The following compounds were obtained by the similar process using the corresponding aniline.

Synthesis Example 23

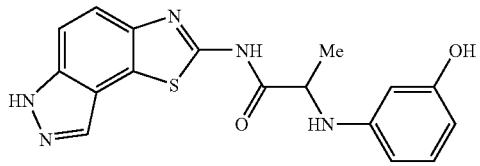

Yield: 2.3%

MASS (ESI+) m/z=354 [M+H]⁺, 191, 136

¹H-NMR (300 MHz, DMSO-d₆) δ (ppm) 12.43 (1H, s), 9.03 (1H, s), 8.31 (1H, s), 7.75 (1H, d, J=9.0 Hz), 7.61 (1H, d, J=9.0 Hz), 6.85 (1H, dd, J=7.8, 7.8 Hz), 6.10-5.96 (3H, m), 4.12-4.28 (1H, m), 1.04 (3H, d, J=6.0 Hz)

Synthesis Example 24

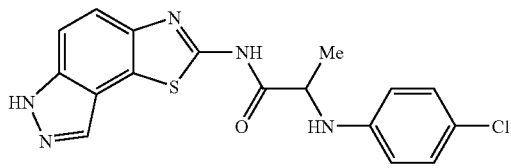

Yield: 2.1%

MASS (ESI+) m/z=372 [M+H]⁺, 232, 191

¹H-NMR (300 MHz, DMSO-d₆) δ (ppm) 8.30 (1H, s), 7.74 (1H, d, J=9.0 Hz), 7.59 (1H, d, J=9.0 Hz), 7.12 (2H, d, J=8.8 Hz), 6.62 (2H, d, J=8.8 Hz), 4.22-4.34 (1H, m), 1.46 (3H, d, J=6.9 Hz)

Synthesis Example 25

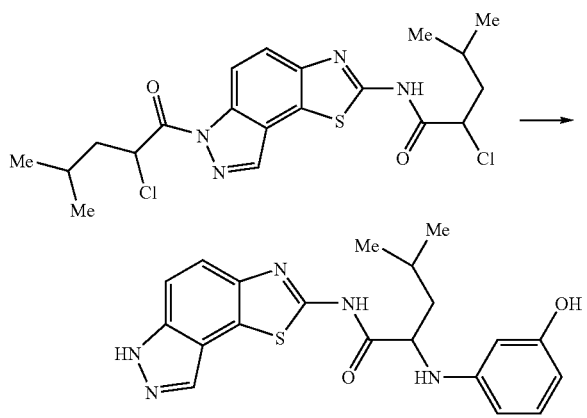

The desired compound was obtained by carrying out the similar procedures to Synthesis example 1 from 0.2 g (0.44 mmol) of 2-chloro-4-methyl-valeric acid [6-(2-chloro-4-methyl-pentanoyl)-6H-pyrazolo[4',3':3,4]benzo[1,2-d]thiazol-2-yl]-amide and 0.14 g (1.3 mmol) of 3-hydroxyaniline.

Yield: 2.5%

MASS (ESI+) m/z=396 [M+H]⁺, 232, 178

¹H-NMR (300 MHz, DMSO-d₆) δ (ppm) 9.02 (1H, s), 8.31 (1H, s), 7.75 (1H, d, J=9.0 Hz), 7.62 (1H, d, J=8.7 Hz), 6.85 (1H, dd, J=7.8, 8.1 Hz), 6.10-6.15 (2H, m), 6.01 (1H, d, J=8.1 Hz), 5.87 (1H, d, J=9.0 Hz), 4.19 (1H, m), 3.57-3.65 (1H, m), 1.60-1.79 (1H, m), 1.04 (6H, d, J=6.0 Hz), 0.95 (2H, dd, J=18.3, 6.3 Hz)

The following compound was obtained by the similar process using the corresponding aniline.

Synthesis Example 26

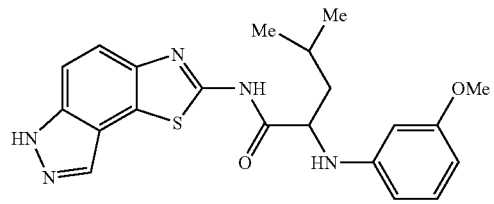

Yield: 1.8%

MASS (ESI+) m/z=410 [M+H]⁺, 192

¹H-NMR (300 MHz, DMSO-d₆) δ (ppm) 8.31 (1H, s), 7.75 (1H, d, J=9.3 Hz), 7.62 (1H, d, J=8.7 Hz), 6.98 (1H, dd, J=8.1, 7.8 Hz), 6.26-6.29 (2H, m), 6.15 (1H, dd, J=8.1, 2.1 Hz), 6.05 (1H, d, J=9.0 Hz), 4.20-4.32 (1H, m), 3.65 (3H, s), 1.56-1.81 (3H, m), 0.96 (6H, dd, J=19.5, 6.3 Hz)

Synthesis Example 27

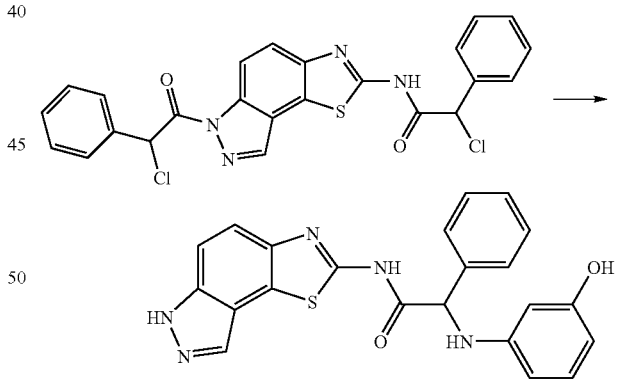

The desired compound was obtained by carrying out the similar procedures to Synthesis example 1 from 0.2 g (0.40 mmol) of 2-chloro-N-[6-(2-chloro-2-phenylacetyl)-6H-pyrazolo[4',3':3,4]benzo[1,2-d]thiazol-2-yl]-2-phenylacetamide and 0.25 g (2.3 mmol) of 3-hydroxyaniline.

Yield: 16.9%

MASS (ESI+) m/z=416 [M+H]⁺, 191

¹H-NMR (300 MHz, DMSO-d₆) δ (ppm) 9.04 (1H, s), 8.29 (1H, s), 7.74 (1H, d, J=9.0 Hz), 7.59-7.64 (3H, m), 7.32-7.43 (3H, m), 6.85 (1H, dd, J=8.1, 7.5 Hz), 6.37 (1H, d, J=8.1 Hz), 6.20 (1H, d, J=7.8 Hz), 6.15 (1H, s), 6.03 (1H, d, J=8.1 Hz), 5.38 (1H, d, J=7.5 Hz)

The following compounds were obtained by the similar process using the corresponding aniline.

Synthesis Example 28

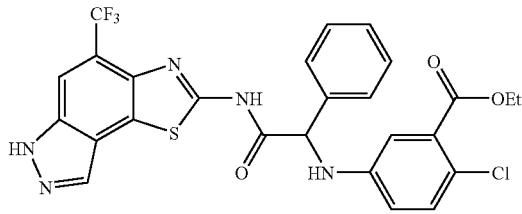

Yield: 6.0%
MASS (ESI+) m/z=574 [M+H]$^+$

Synthesis Example 29

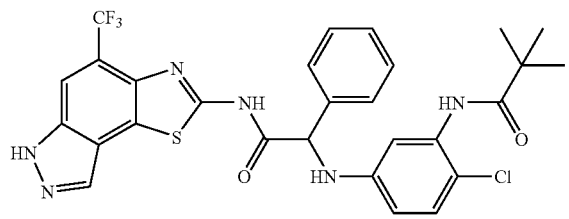

Yield: 3.9%
MASS (ESI+) m/z=601 [M]$^+$

Synthesis Example 30

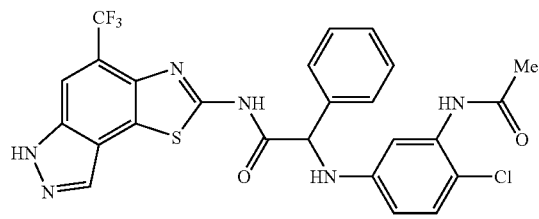

Yield: 4.6%
MASS (ESI+) m/z=559 [M+H]$^+$

Synthesis Example 31

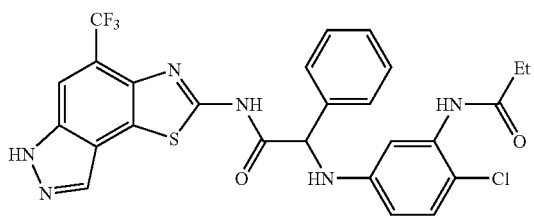

Yield: 1.3%
MASS (ESI+) m/z=573 [M+H]$^+$

Synthesis Example 32

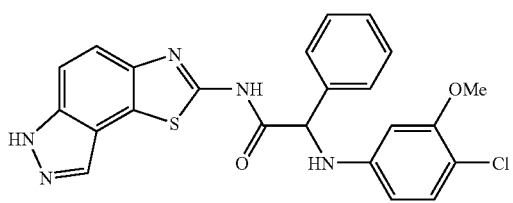

Yield: 1.5%
MASS (ESI+) m/z=464 [M+H]$^+$, 308, 232, 191

Synthesis Example 33

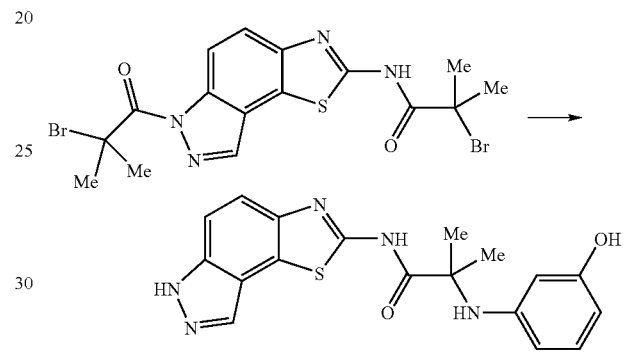

0.2 g (0.4 mmol) of 2-bromo-N-[6-(2-bromo-2-methyl-propionyl)-6H-pyrazolo[4',3':3,4]benzo[1,2-d]thiazol-2-yl]-2-methyl-propionamide, 0.26 g (2.4 mmol) of 3-hydroxyaniline and 0.1 g (0.7 mmol) of sodium iodide were heated at 130° C. in 4 ml of ethylene glycol. After the completion of the reaction was confirmed by HPLC, the reaction mixture was cooled to room temperature, and 4 ml of water was added to the mixture. The mixture was extracted with 4 ml of ethyl acetate twice, dried over 3 g of anhydrous magnesium sulfate, and then concentrated under reduced pressure. The crude product was purified by silica gel column chromatography (hexane/ethyl acetate=1/1) to give 4.6 mg (yield: 3.1%) of the desired compound.

MASS (ESI+) m/z=368 [M+H]$^+$, 259, 191, 150
$^1$H-NMR (300 MHz, DMSO-d$_6$) δ (ppm) 11.94 (1H, s), 9.02 (1H, s), 8.31 (1H, s), 7.67 (1H, d, J=9.0 Hz), 7.59 (1H, d, J=8.7 Hz), 6.82 (1H, dd, J=7.5, 8.7 Hz), 5.95-6.01 (3H, m), 5.73 (1H, brs), 3.32 (6H, s)

The following compounds were obtained by the similar process using the corresponding aniline.

Synthesis Example 34

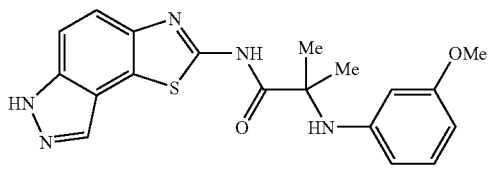

Yield: 2.0%
MASS (ESI+) m/z=382 [M+H]⁺, 259, 191, 164
¹H-NMR (300 MHz, DMSO-d₆) δ (ppm) 12.06 (1H, s), 8.32 (1H, s), 7.68 (1H, d, J=8.7 Hz), 7.59 (1H, d, J=9.0 Hz), 6.96 (1H, dd, J=7.8, 8.1 Hz), 6.06-6.16 (4H, m), 3.60 (3H, s), 3.34 (6H, s)

Synthesis Example 35

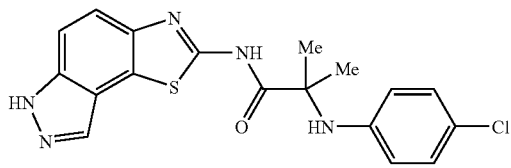

Yield: 2.0%
MASS (ESI+) m/z=386 [M+H]⁺, 259, 231, 168
¹H-NMR (300 MHz, DMSO-d₆) δ (ppm) 8.31 (1H, s), 7.68 (1H, d, J=8.8 Hz), 7.59 (1H, d, J=8.8 Hz), 7.09 (2H, d, J=8.8 Hz), 6.48 (2H, d, J=8.8 Hz), 6.11 (1H, s), 1.54 (6H, s)

Synthesis Example 36

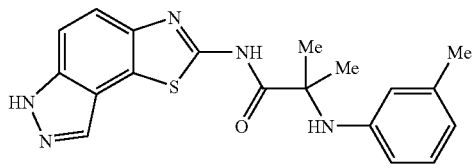

Yield: 5%
MASS (ESI+) m/z=366 [M+H]⁺

Synthesis Example 37

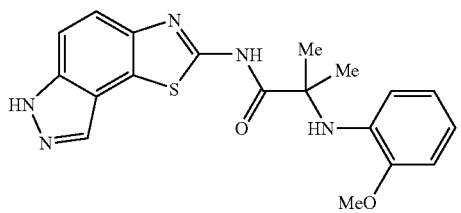

Yield: 5%
MASS (ESI+) m/z=382 [M+H]⁺

Synthesis Example 38

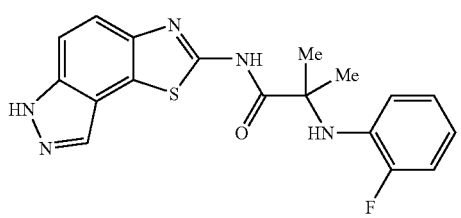

Yield: 3%
MASS (ESI+) m/z=370 [M+H]⁺, 191

Synthesis Example 39

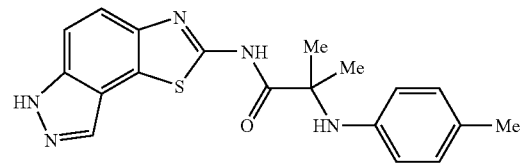

Yield: 10.4%
MASS (ESI+) m/z=366 [M+H]⁺, 231

Synthesis Example 40

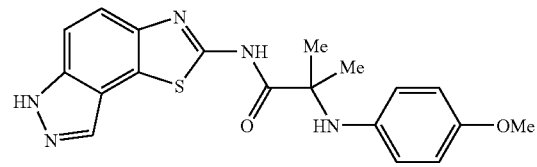

Yield: 4.7%
MASS (ESI+) m/z=382 [M+H]⁺, 231

Synthesis Example 41

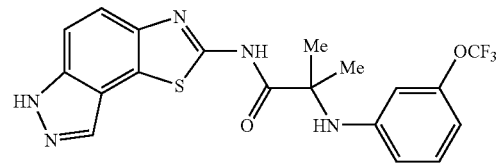

Yield: 1.1%
MASS (ESI+) m/z=436 [M+H]⁺, 259, 231

Synthesis Example 42

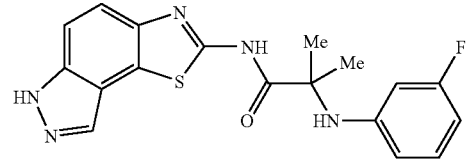

Yield: 1.3%
MASS (ESI+) m/z=370 [M+H]⁺, 259, 231, 152

Synthesis Example 43

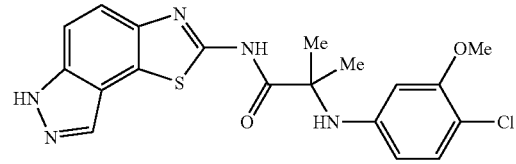

Yield: 2%
MASS (ESI+) m/z=416, 418 [M+H]⁺

Synthesis Example 44

Yield: 2%
MASS (ESI+) m/z=458, 460 [M+H]$^+$

Synthesis Example 45

Yield: 3%
MASS (ESI+) m/z=410 [M+H]$^+$, 191

Synthesis Example 46

Yield: 5.2%
MASS (ESI+) m/z=382 [M+H]$^+$, 341, 231

Synthesis Example 47

Yield: 3.5%
MASS (ESI+) m/z=472 [M+H]$^+$, 259, 231

Synthesis Example 48

Yield: 2.6%
MASS (ESI+) m/z=386 [M+H]$^+$, 259, 231, 130

Synthesis Example 49

Yield: 4.9%
MASS (ESI+) m/z=442 [M+H]$^+$, 259, 196, 155

Synthesis Example 50

Yield: 3%
MASS (ESI+) m/z=459 [M+H]$^+$, 191

Synthesis Example 51

A mixture of 181 mg of 2-bromo-N-[6-(2-bromo-2-methyl-propionyl)-4-trifluoromethyl-6H-pyrazolo[4',3':3,4]benzo[1,2-d]thiazol-2-yl]-2-methyl-propionamide, 211 mg of 4-chloro-3-methoxyaniline, 100 mg of sodium iodide and 4.0 ml of ethylene glycol was heated at 130° C. for 6 hours. The mixture was cooled to room temperature, water was added to the mixture, and the precipitated solid was collected by filtration. The crude product was purified by silica gel column chromatography (chloroform:methanol=100:1-10:1) to give 12 mg (yield: 8%) of the desired compound.

MASS (ESI+) m/z=484, 486 [M+H]$^+$

The following compounds were obtained by the similar process using the corresponding aniline.

Synthesis Example 52

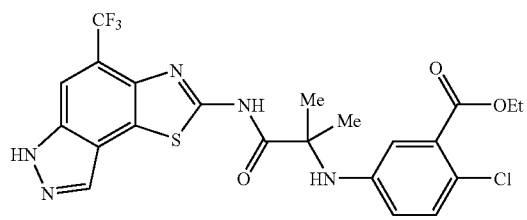

Yield: 14%
MASS (ESI+) m/z=526, 528 [M+H]$^+$

Synthesis Example 53

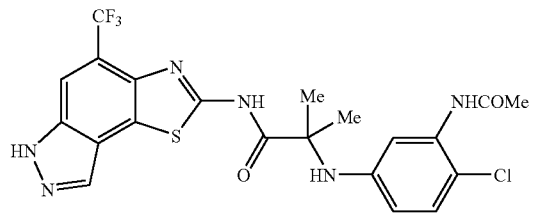

Yield: 11%
MASS (ESI+) m/z=511, 513 [M+H]$^+$

Synthesis Example 54

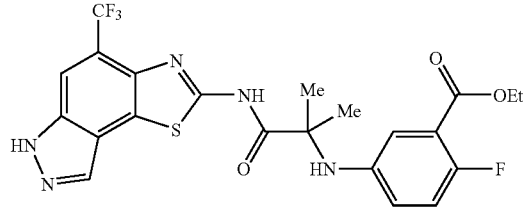

Yield: 10%
MASS (ESI+) m/z=510 [M+H]$^+$

Synthesis Example 55

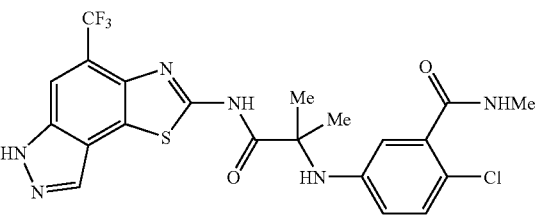

Yield: 4%
MASS (ESI+) m/z=511, 513 [M+H]$^+$
$^1$H-NMR (500 MHz, DMSO-d$_6$) δ (ppm) 8.51 (1H, s), 8.21 (1H, brs), 7.99 (1H, s), 7.14 (1H, d, J=8.9 Hz), 6.55 (1H, s), 6.45 (1H, d, J=8.9 Hz), 6.20 (1H, s), 2.68 (3H, d, J=4.6 Hz), 1.57 (6H, s)

Synthesis Example 56

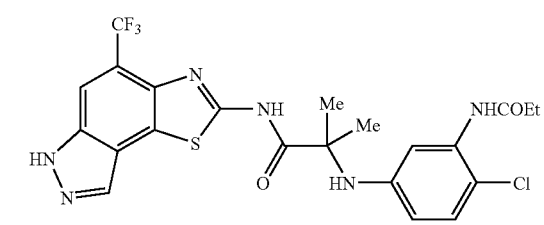

Yield: 11%
MASS (ESI+) m/z=525, 527 [M+H]$^+$

Synthesis Example 57

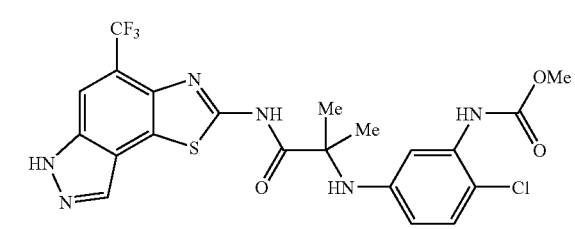

Yield: 13%
MASS (ESI+) m/z=527 [M+H]$^+$, 327

Synthesis Example 58

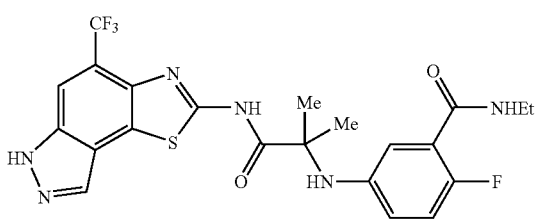

Yield: 6%
MASS (ESI+) m/z=509 [M+H]$^+$, 327

Synthesis Example 59

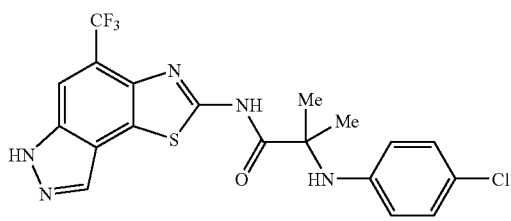

Yield: 5.3%
MASS (ESI+) m/z=454 [M+H]⁺, 327, 299, 168
$^1$H-NMR (300 MHz, DMSO-$d_6$) δ (ppm) 8.50 (1H, s), 7.99 (1H, s), 7.10 (2H, d, J=8.8 Hz), 6.49 (2H, d, J=8.8 Hz), 1.56 (6H, s)

Synthesis Example 60

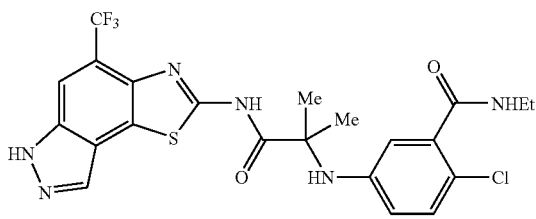

Yield: 1.5%
MASS (ESI+) m/z=525 [M+H]⁺
$^1$H-NMR (500 MHz, DMSO-$d_6$) δ (ppm) 8.49 (1H, s), 8.26 (1H, t, J=5.5 Hz), 7.80 (1H, s), 7.12 (1H, d, J=8.9 Hz), 6.56 (1H, s), 6.42 (1H, d, J=8.9 Hz), 6.20 (1H, s), 3.16 (2H, m), 1.56 (6H, s), 1.02 (3H, t, J=5.9 Hz)

Synthesis Example 61

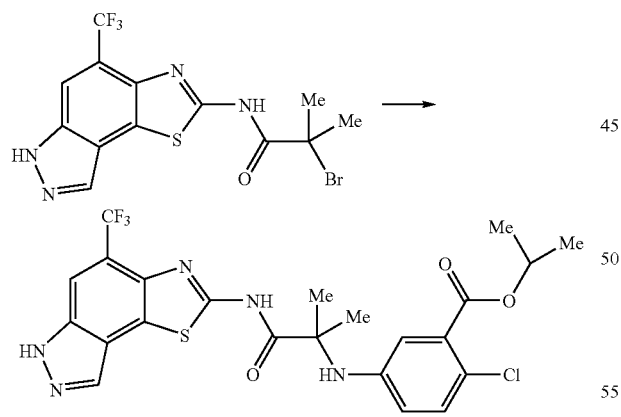

0.1 g (0.25 mmol) of 2-bromo-2-methyl-N-(4-trifluoromethyl-6H-pyrazolo[4',3':3,4]benzo[1,2-d]thiazol-2-yl)-propionamide, 0.13 g (0.89 mmol) of isopropyl 2-chloro-5-aminobenzoate were heated at 100° C. in 4 ml of ethylene glycol. After the completion of the reaction was confirmed by HPLC, the reaction mixture was cooled to room temperature, and 4 ml of water was added to the mixture. The mixture was extracted with 4 ml of ethyl acetate twice, dried over 3 g of anhydrous magnesium sulfate, and then concentrated under reduced pressure. The crude product was purified by silica gel column chromatography (hexane/ethyl acetate=1/1) to give 5.4 mg (yield: 4.1%) of the desired compound.
MASS (ESI+) m/z=540 [M+H]⁺, 470, 327, 254

The following compounds were obtained by the similar process using the corresponding aniline.

Synthesis Example 62

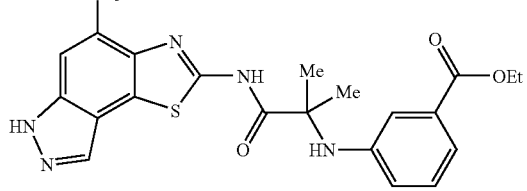

Yield: 4.1%
MASS (ESI+) m/z=492 [M+H]⁺, 206

Synthesis Example 63

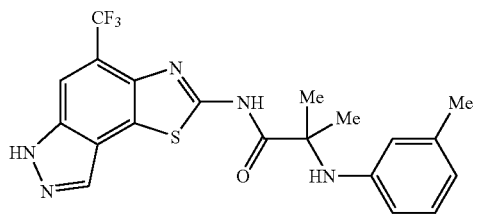

Yield: 5.3%
MASS (ESI+) m/z=434 [M+H]⁺, 327, 148

Synthesis Example 64

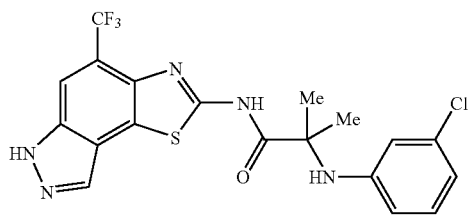

Yield: 4.5%
MASS (ESI+) m/z=454 [M+H]⁺, 327, 299, 168

Synthesis Example 65

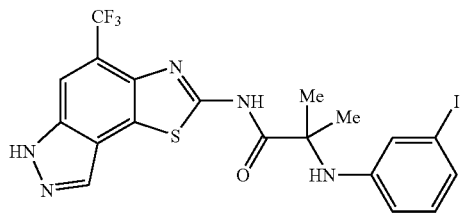

Yield: 4.5%
MASS (ESI+) m/z=546 [M+H]⁺, 327, 260

Synthesis Example 66

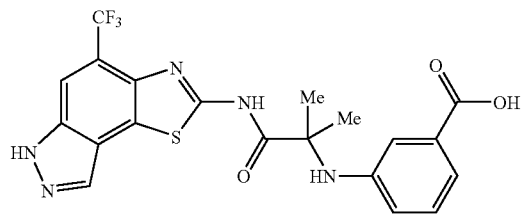

Yield: 3.8%
MASS (ESI+) m/z=464 [M+H]⁺, 178

Synthesis Example 67

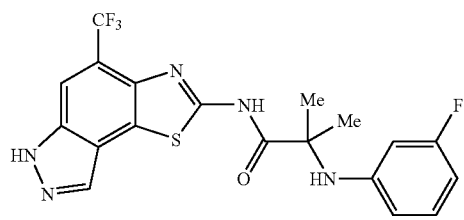

Yield: 4.6%
MASS (ESI+) m/z=438 [M+H]⁺, 327, 299, 259, 152

Synthesis Example 68

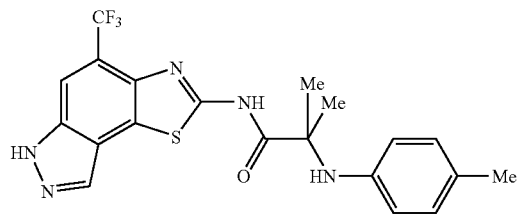

Yield: 5.9%
MASS (ESI+) m/z=434 [M+H]⁺, 327, 148

Synthesis Example 69

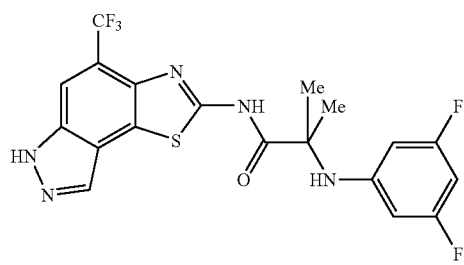

Yield: 1.9%
MASS (ESI+) m/z=456 [M+H]⁺, 299, 170

Synthesis Example 70

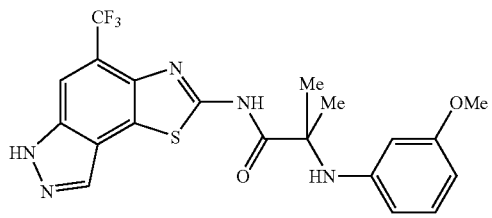

Yield: 3.7%
MASS (ESI+) m/z=450 [M+H]⁺, 259, 192, 164

Synthesis Example 71

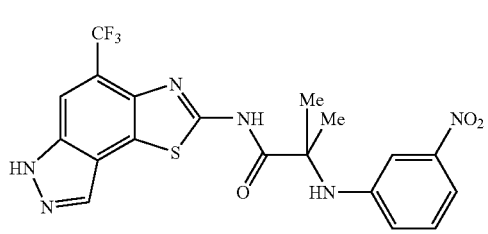

Yield: 3.6%
MASS (ESI+) m/z=465 [M+H]⁺, 299

Synthesis Example 72

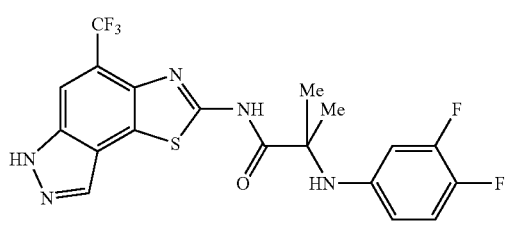

Yield: 3.7%
MASS (ESI+) m/z=456 [M+H]⁺, 299, 259, 170

Synthesis example 73

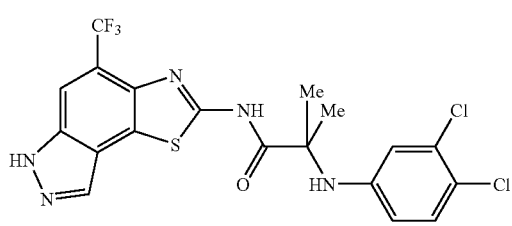

Yield: 3.7%
MASS (ESI+) m/z=488 [M]⁺, 328, 299, 259

Synthesis Example 74

Yield: 3.9%
MASS (ESI+) m/z=438 [M+H]+, 299, 259, 152

Synthesis Example 75

Yield: 3.4%
MASS (ESI+) m/z=537 [M+H]+, 327, 240

Synthesis Example 76

Yield: 3.5%
MASS (ESI+) m/z=509 [M+H]+, 223

Synthesis Example 77

Yield: 3.7%
MASS (ESI+) m/z=553 [M]+, 267

Synthesis Example 78

Yield: 4.5%
MASS (ESI+) m/z=491 [M+H]+, 389, 259, 205

Synthesis Example 79

Yield: 3.5%
MASS (ESI+) m/z=513 [M+H]+, 327, 227

Synthesis Example 80

Yield: 3.7%
MASS (ESI+) m/z=537 [M+H]+, 328, 251

Synthesis Example 81

Yield: 2.7%
MASS (ESI+) m/z=495 [M+H]+, 209

Synthesis Example 82

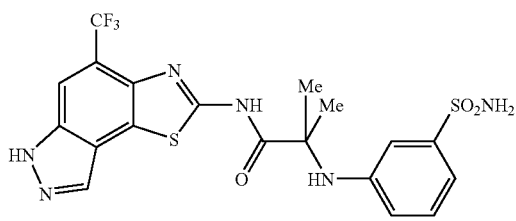

Yield: 3.8%
MASS (ESI+) m/z=499 [M+H]+, 327
1H-NMR (400 MHz, DMSO-d6) δ (ppm) 8.47 (1H, s), 7.95 (1H, s), 7.19 (1H, t, J=8.0 Hz), 7.17 (2H, s), 7.03 (1H, d, J=2.0 Hz), 6.98 (1H, d, J=8.0 Hz), 6.52 (1H, dd, J=8.0, 2.0 Hz), 6.30 (1H, brs), 1.56 (6H, s)

Synthesis Example 83

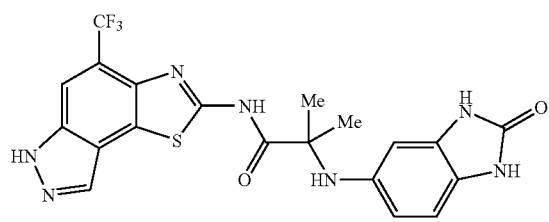

Yield: 3.1%
MASS (ESI+) m/z=476 [M+H]+, 190

Synthesis Example 84

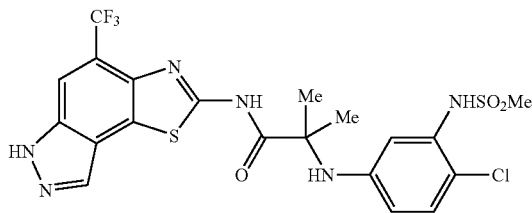

Yield: 3.6%
MASS (ESI+) m/z=547 [M+H]+, 327, 260

Synthesis Example 85

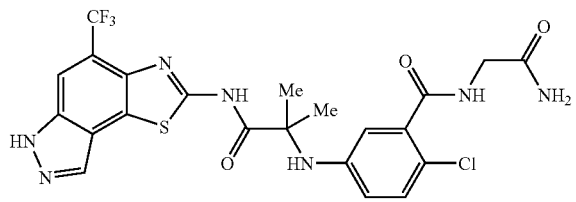

Yield; 3.2%
MASS (ESI+) m/z=554 [M+H]+, 537, 480, 327, 240
1H-NMR (300 MHz, DMSO-d6) δ (ppm); 12.43 (1H, brs), 8.51 (1H, s), 8.41 (1H, t, J=5.7 Hz), 8.00 (1H, s), 7.15 (1H, d, J=8.7 Hz), 7.12-7.18 (2H, m), 6.74 (1H, d, J=3.0 Hz), 6.41 (1H, dd, J=8.7, 2.7 Hz), 6.26 (1H, brs), 3.75 (1H, d, J=5.7 Hz), 3.31-3.75 (2H, m), 1.58 (6H, s)

Synthesis Example 86

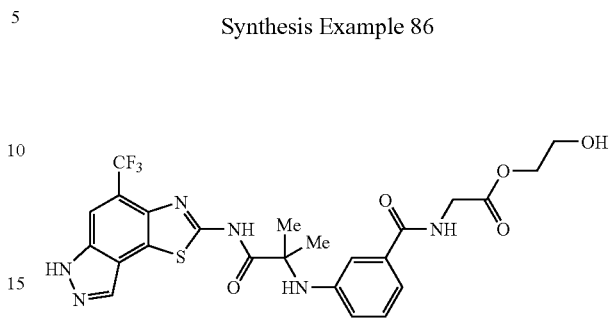

Yield: 0.8%
MASS (ESI+) m/z=565 [M+H]+

Synthesis Example 87

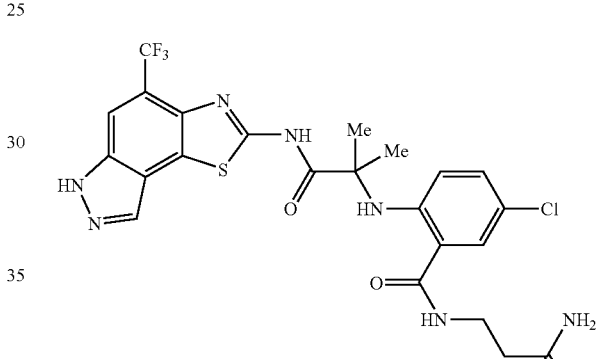

Yield: 3.9%
MASS (ESI+) m/z=568 [M+H]+

Synthesis Example 88

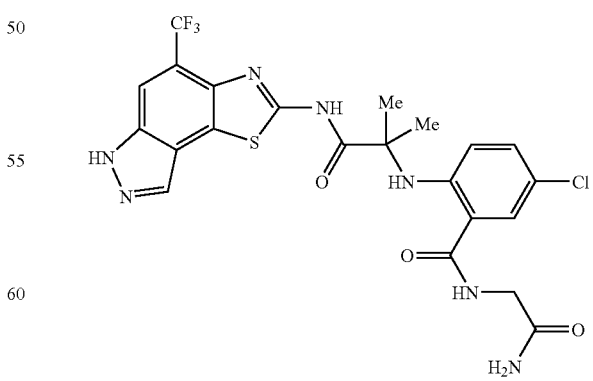

Yield: 3.1%
MASS (ESI+) m/z=554 [M+H]+

Synthesis Example 89

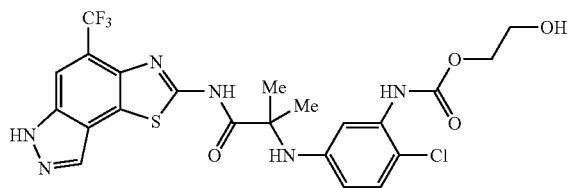

Yield: 3.1%
MASS (ESI+) m/z=557 [M+H]+, 495, 328, 271

Synthesis Example 90

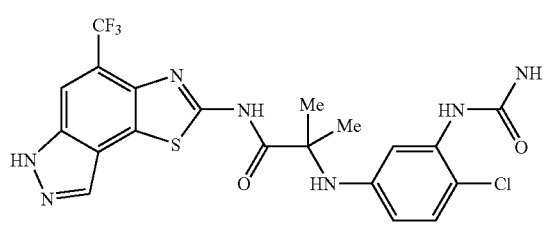

Yield: 3.8%
MASS (ESI+) m/z=526 [M+H]+, 328, 240

Synthesis Example 91

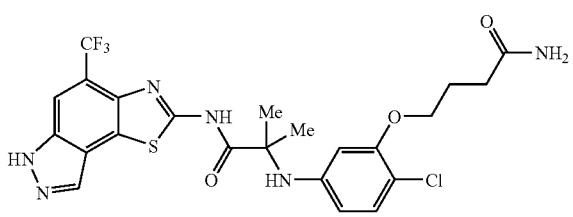

Yield: 5.9%
MASS (ESI+) m/z=555 [M+H]+, 470, 327, 299

Synthesis Example 92

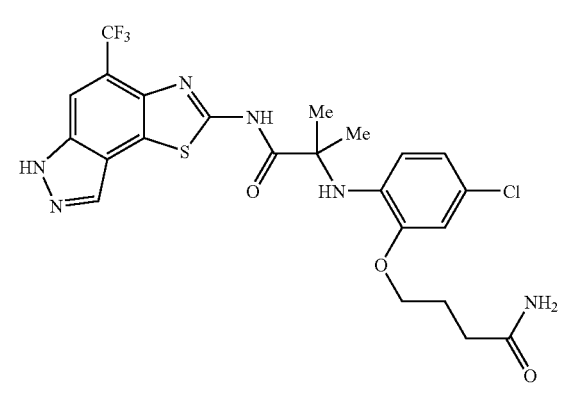

Yield: 5.1%
MASS (ESI+) m/z=555 [M+H]+, 328

Synthesis Example 93

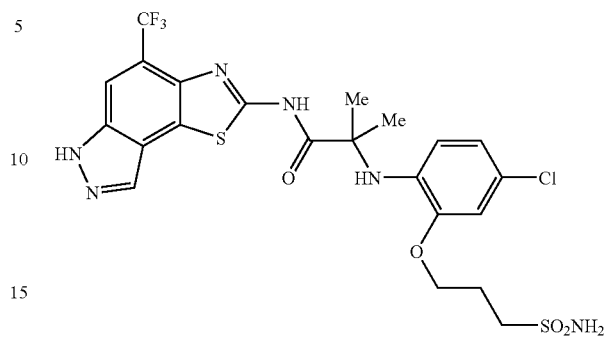

Yield: 6.1%
MASS (ESI+) m/z=591 [M]+, 409, 328, 264

Synthesis Example 94

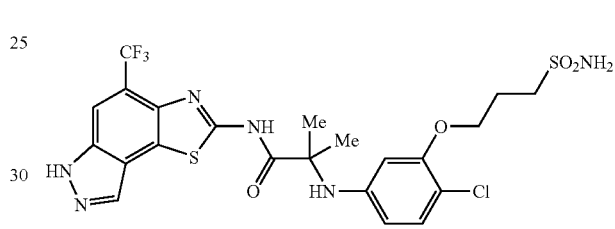

Yield: 5.3%
MASS (ESI+) m/z=591 [M]+, 327, 184

Synthesis Example 95

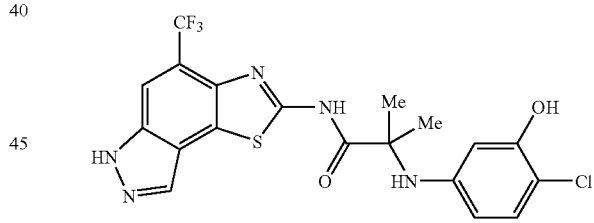

Yield: 4.4%
MASS (ESI+) m/z=470 [M+H]+, 328, 259, 184, 143

Synthesis Example 96

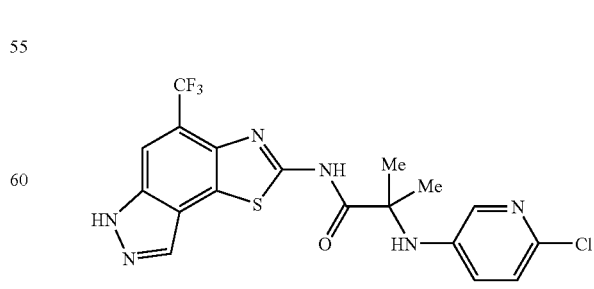

Yield: 1.1%
MASS (ESI+) m/z=455 [M+H]+, 299, 169

Synthesis Example 97

Yield: 4.2%
MASS (ESI+) m/z=536 [M+H]$^+$, 299, 250

Synthesis Example 98

Yield: 3.0%
MASS (ESI+) m/z=603 [M]$^+$, 480, 409, 327, 227

Synthesis Example 99

Yield: 5.1%
MASS (ESI+) m/z=544 [M+H]$^+$, 328, 258
$^1$H-NMR (300 MHz, DMSO-d$_6$) δ (ppm) 12.43 (1H, brs), 8.51 (1H, s), 8.00 (1H, s), 7.06 (1H, d, J=8.7 Hz), 6.33 (1H, d, J=2.4 Hz), 6.08 (1H, brs), 6.02 (1H, dd, J=8.7, 2.4 Hz), 4.94 (1H, d, J=4.5 Hz), 4.64 (1H, t, J=5.7 Hz), 3.86-3.90 (1H, m), 3.78-3.83 (2H, m), 3.42-3.48 (2H, m), 3.33-3.19 (1H, m), 1.59 (6H, s)

Synthesis Example 100

Yield: 5.1%
MASS (ESI+) m/z=541 [M+H]$^+$, 327, 255

Synthesis Example 101

Yield: 4.8%
MASS (ESI+) m/z=534 [M+H]$^+$, 517, 446, 299, 223

Synthesis Example 102

Yield: 2.9%
MASS (ESI+) m/z=618 [M]$^+$, 299

Synthesis Example 103

0.28 g of WSCI was added to a mixture of 0.3 g of 3-(benzyloxy)-2-(4-chlorophenylamino)propionic acid, 0.2 g of 6H-pyrazolo[4',3':3,4]benzo[1,2-d]thiazol-2-yl-amine, 0.2 g of HOBt and 8 ml of dimethylformamide, and the mixture was stirred at room temperature for 12 hours. 100 ml of water was added to the mixture and the mixture was extracted with ethyl acetate. The extract was washed with brine, and then concentrated to dryness under reduced pressure. The residue was purified by silica gel column chromatography (chloroform:methanol=10:1) to give 0.11 g (yield: 24%) of the desired compound.
MASS (ESI+) m/z=478 [M+H]$^+$, 191
The following compounds were obtained by the similar process.

Synthesis Example 104

Yield: 1.5%
MASS (ESI+) m/z=324 [M+H]$^+$, 191

¹H-NMR (300 MHz, DMSO-d₆) δ (ppm) 13.38 (1H, brs), 12.40 (1H, brs), 8.30 (1H, s), 7.75 (1H, d, J=8.7 Hz), 7.61 (1H, d, J=8.7 Hz), 7.10 (2H, dd, J=8.1, 7.5 Hz), 6.56-6.63 (3H, m), 6.11 (1H, t, J=5.1 Hz), 4.09 (2H, d, J=5.7 Hz)

Synthesis Example 105

Yield: 2%

Synthesis Example 106

Yield: 1%
MASS (ESI+) m/z=381 [M+H]⁺, 191

Synthesis Example 107

Yield: 1%
MASS (ESI+) m/z=392, 394, 396 [M+H]⁺

Synthesis Example 108

Yield: 0.9%
MASS (ESI+) m/z=358 [M+H]⁺, 265, 225, 106

The following compound was obtained by the similar process to Synthesis example 103 using 2-(3-hydroxyphenylamino)-succinic acid.

Synthesis Example 109

Yield: 17%
MASS (ESI+) m/z=397 [M+H]⁺, 191

The following compound was obtained by the similar process using the corresponding carboxylic acid.

Synthesis Example 110

Yield: 16%
MASS (ESI+) m/z=411 [M+H]⁺, 191

The following compound was obtained by the similar process to Synthesis example 103 using 1-(4-chlorophenyl)-pyrrolidine-2-carboxylic acid.

Synthesis Example 111

Yield: 28.9%
MASS (ESI+) m/z=398 [M+H]⁺

The following compound was obtained by the similar process to Synthesis example 103 using 2-(4-chlorophenylamino)-4-methoxybutyric acid.

Synthesis Example 112

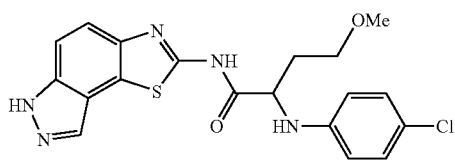

Yield: 96.4%
MASS (ESI+) m/z=416 [M+H]+

The following compound was obtained by the similar process to Synthesis example 103 using 2-(4-chlorophenylamino)-4-hydroxybutyric acid.

Synthesis Example 113

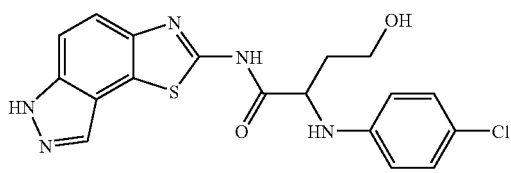

Yield: 4.9%
MASS (ESI+) m/z=402 [M+H]+

The following compound was obtained by the similar process to Synthesis example 103 using 1-(4-chlorophenylamino)-cyclobutanecarboxylic acid.

Synthesis Example 114

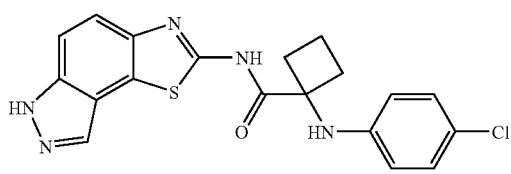

Yield: 1%
MASS (ESI+) m/z=398 [M+H]+, 191

The following compound was obtained by the similar process to Synthesis example 103 using 1-(4-chlorophenylamino)-cyclopentanecarboxylic acid.

Synthesis Example 115

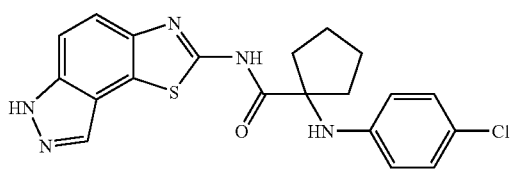

Yield: 49%
MASS (ESI+) m/z=412 [M+H]+

The following compound was obtained by the similar process to Synthesis example 103 using 1-(4-chlorophenylamino)-cyclohexanecarboxylic acid.

Synthesis Example 116

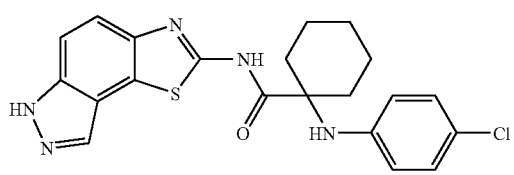

Yield: 40%
MASS (ESI+) m/z=426 [M+H]+

The following compound was obtained by the similar process to Synthesis example 103 using 1-(4-chlorophenylamino)-cyclopropanecarboxylic acid.

Synthesis Example 117

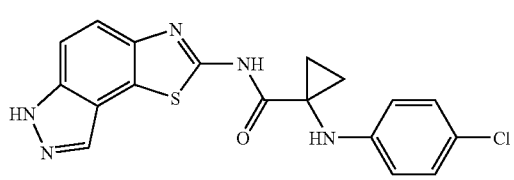

Yield: 15%
MASS (ESI+) m/z=384 [M+H]+, 191

The following compounds were obtained by the similar process using the corresponding carboxylic acid.

Synthesis Example 118

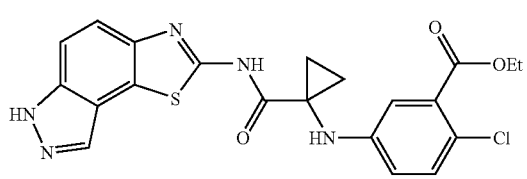

Yield: 20%
MASS (ESI+) m/z=456 [M+H]+, 191

Synthesis Example 119

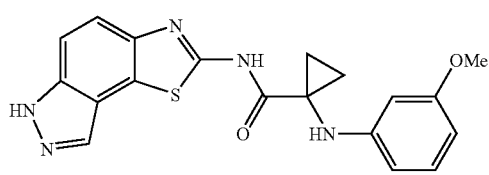

Yield: 30%
MASS (ESI+) m/z=380 [M+H]+, 191

Synthesis Example 120

Yield: 2%
MASS (ESI+) m/z=425 [M+H]+, 191

Synthesis Example 121

Yield: 6%
MASS (ESI+) m/z=439 [M+H]+, 191

Synthesis Example 122

Yield: 6%
MASS (ESI+) m/z=366 [M+H]+, 191

Synthesis Example 123

Yield: 26%
MASS (ESI+) m/z=470 [M+H]+, 191

Synthesis Example 124

Yield: 9%
MASS (ESI+) m/z=455 [M+H]+, 191

Synthesis Example 125

Yield: 8%
MASS (ESI+) m/z=483 [M+H]+, 191

Synthesis Example 126

Yield: 3%
MASS (ESI+) m/z=441 [M+H]+, 191
$^1$H-NMR (400 MHz, DMSO-$d_6$) δ (ppm) 8.26 (1H, brs), 8.19 (1H, q, J=4.0 Hz), 7.64 (1H, d, J=8.8 Hz), 7.56 (1H, dd, J=8.8, 1.0 Hz), 7.18 (1H, d, J=8.6 Hz), 6.75 (1H, brs), 6.63 (1H, dd, J=8.6, 2.6 Hz), 6.60 (1H, d, J-2.6 Hz), 2.67 (3H, d, J=4.0 Hz), 1.60 (2H, m), 1.10 (2H, m)

Synthesis Example 127

Yield: 23%
MASS (ESI+) m/z=398, 400 [M+H]+

The following compound was obtained by the similar process to Synthesis example 103 using 2-(3-acetylamino-4-chlorophenylamino)-2-methylpropionic acid.

Synthesis Example 128

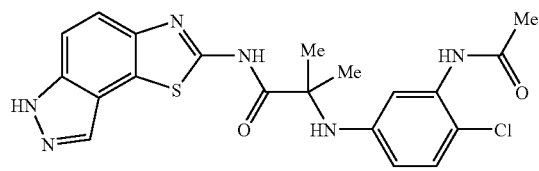

Yield: 11%
MASS (ESI+) m/z=443 [M+H]+, 191
$^1$H-NMR (400 MHz, DMSO-$d_6$) δ (ppm) 9.19 (1H, s), 8.31 (1H, s) 7.67 (1H, d, J=8.8 Hz), 7.59 (1H, d, J=8.8 Hz), 7.12 (1H, d, J=8.2 Hz), 7.01 (1H, brs), 6.25 (1H, brd, J=8.2 Hz), 6.11 (1H, s), 2.02 (3H, s), 1.54 (6H, s)

The following compound was obtained by the similar process using the corresponding carboxylic acid.

Synthesis Example 129

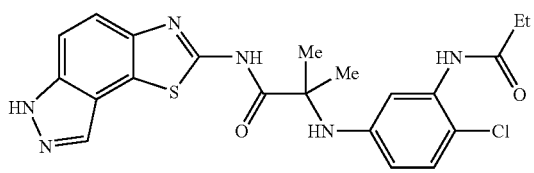

Yield: 14.8%
MASS (ESI+) m/z=457 [M+H]+

Synthesis Example 130

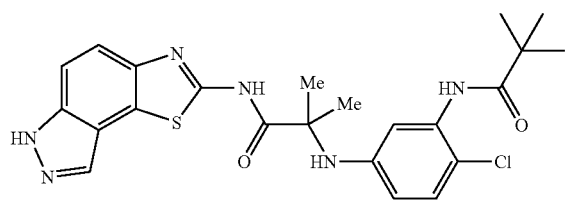

Yield: 1.5%
MASS (ESI+) m/z=486 [M+H]+

The following compound was obtained by the similar process to Synthesis example 103 using (3-acetylamino-4-chlorophenylamino)-phenylacetic acid.

Synthesis Example 131

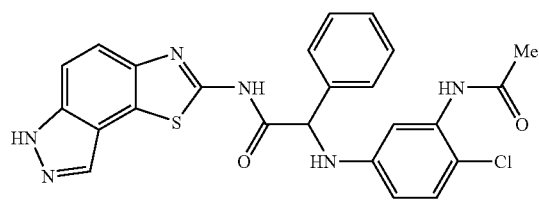

Yield: 1.1%
MASS (ESI+) m/z=491 [M+H]+, 308, 149

Synthesis Example 132

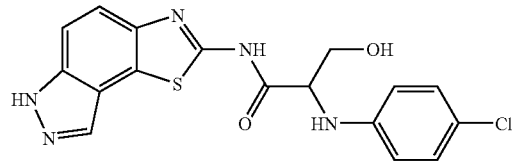

A mixture of 50 mg of the compound of Synthesis example 103 and 5 ml of dichloromethane was cooled to −45° C., 0.3 ml of a solution of boran tribromide in dichloromethane (1M) was then added dropwise to the mixture under a nitrogen atmosphere. After the mixture was allowed to warm to room temperature, the mixture was stirred for 2 hours. Under ice-cooling, 50 ml of water was added dropwise to the mixture, and the mixture was extracted with ethyl acetate. The extract was washed with brine, and then concentrated to dryness under reduced pressure. Diethyl ether was added to the residue and the precipitated crystals were collected by filtration to give 16 mg (yield: 39%) of the desired compound.

MASS (ESI+) m/z=388 [M+H]+, 191

Synthesis Example 133

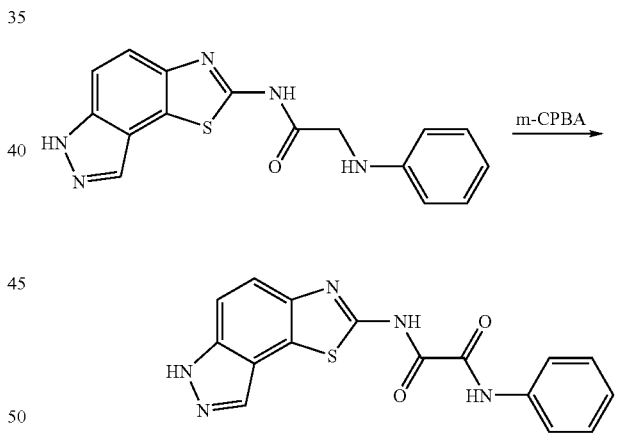

A mixture of the compound (20 mg) of the Synthesis example 104, m-chloroperbenzoic acid (m-CPBA) (20 mg) and 5 ml of dichloromethane was stirred at room temperature for 3 hours. Under ice-cooling, a saturated aqueous sodium hydrogen carbonate solution was added to the mixture to separate the liquid. The organic layer was washed with a saturated aqueous sodium hydrogen carbonate solution and brine, and then concentrated to dryness under reduced pressure. Diethyl ether was added to the residue and the precipitated crystals were collected by filtration to give 10 mg (yield: 50%) of the desired compound.

MASS (ESI+) m/z=338 [M+H]+

¹H-NMR (300 MHz, DMSO-d₆) δ (ppm) 8.51 (s, 1H), 8.41 (s, 1H), 7.97-8.00 (m, 2H), 7.83 (d, J=9.0 Hz, 1H), 7.61-7.69 (m, 4H)

Synthesis Example 134

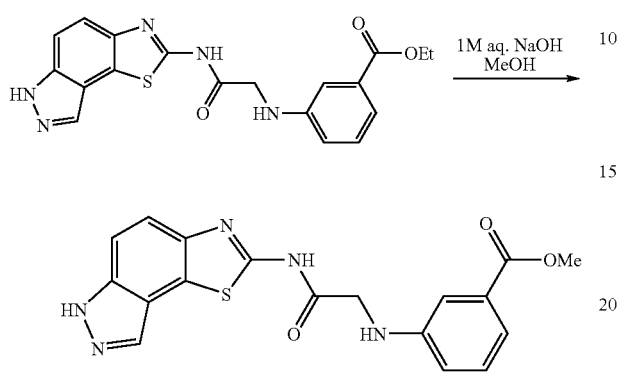

A mixture of 30 mg of the compound of Synthesis example 10, 1 ml of methanol and 0.1 ml of 1M aqueous sodium hydroxide solution was stirred at room temperature for 2 days. After the completion of the reaction was confirmed by HPLC, the reaction mixture was concentrated under reduced pressure, 1M hydrochloric acid was added to the mixture until it became acidic, followed by filtration. The solid collected by filtration was washed with water to give 5.1 mg (yield: 17%) of the desired compound.

MASS (ESI+) m/z=382 [M+H]⁺

Synthesis Example 135

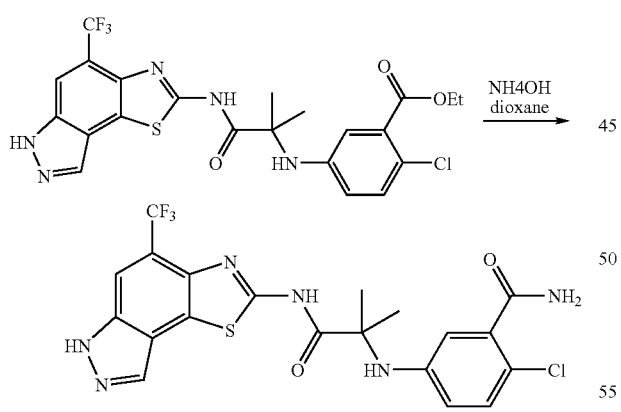

A mixture of 20 mg of the compound of Synthesis example 52, 1 ml of 1,4-dioxane and 2 ml of 28% ammonia water was stirred at room temperature for 3 days. After the completion of the reaction was confirmed by HPLC, the reaction mixture was concentrated under reduced pressure, and water was added to the residue. The precipitated solid was washed with water and diethyl ether to give 3.9 mg (yield: 21%) of the desired compound as a gray solid.

MASS (ESI+) m/z=497, 499 [M+H]⁺

¹H-NMR (400 MHz, DMSO-d₆) δ (ppm) 8.51 (1H, s), 8.00 (1H, s), 7.75 (1H, s), 7.44 (1H, s), 7.12 (1H, d, J=8.6 Hz), 6.59 (1H, d, J=2.6 Hz), 6.44 (1H, dd, J=8.6, 2.6 Hz), 6.22 (1H, s), 1.58 (6H, s)

Synthesis Example 136

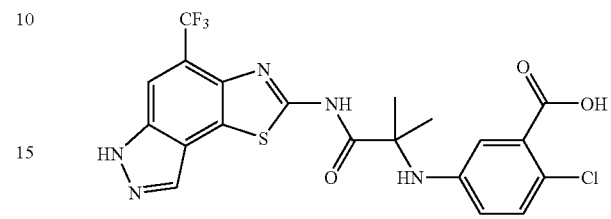

The desired compound (yield: 11%) was obtained as a by-product at the time of synthesizing the compound of Synthesis example 135.

MASS (ESI+) m/z=498, 500 [M+H]⁺

Synthesis Example 137

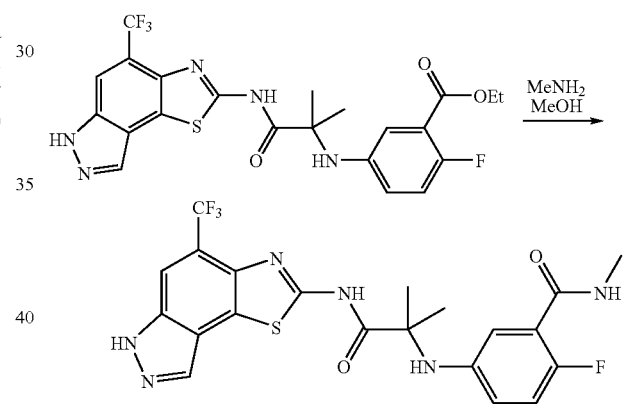

A mixture of 53 mg of the compound of Synthesis example 54, 1 ml of methanol and 10 ml of a 40% methylamine-methanol solution was stirred at room temperature for 14 hours. After the completion of the reaction was confirmed by HPLC, the reaction mixture was concentrated under reduced pressure, and ethanol was added to the residue. The precipitated solid was washed with ethanol to give 28 mg (yield: 55%) of the desired compound.

MASS (ESI+) m/z=495 [M+H]⁺

Synthesis Example 138

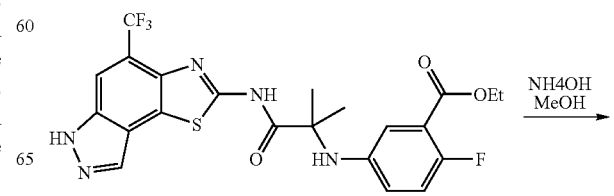

-continued

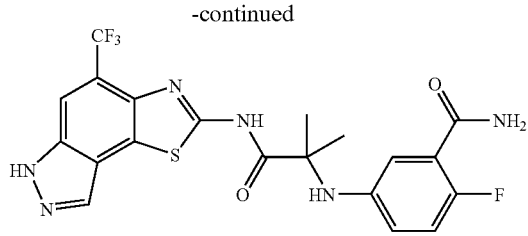

A mixture of 53 mg of the compound of Synthesis example 54, 2 ml of ethanol and 10 ml of 28% ammonia water was stirred at room temperature for 2 days. After the completion of the reaction was confirmed by HPLC, the reaction mixture was concentrated under reduced pressure, and ethanol was added to the residue. The precipitated solid was washed with ethanol to give 28 mg (yield: 56%) of the desired compound.

MASS (ESI+) m/z=481 [M+H]+

$^1$H-NMR (300 MHz, DMSO-$d_6$) δ (ppm) 8.50 (1H, s), 7.99 (1H, s), 7.52-7.41 (2H, m), 7.00 (1H, t, J=9.4 Hz), 6.85-6.80 (1H, m), 6.60-6.50 (1H, m), 1.56 (6H, s)

Synthesis Example 139

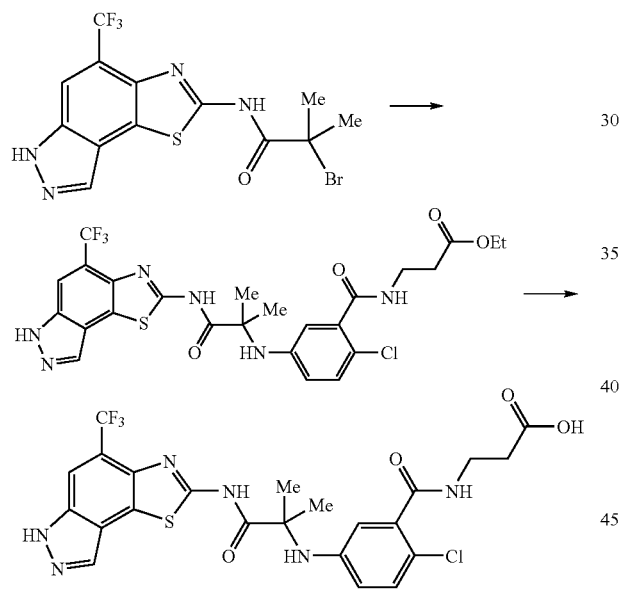

0.1 g (0.25 mmol) of 2-bromo-2-methyl-N-(4-trifluoromethyl-6H-pyrazolo[4',3':3,4]benzo[1,2-d]thiazol-2-yl)-propionamide and 0.23 g (0.85 mmol) of ethyl 3-(5-amino-2-chlorobenzoylamino)-propionate were heated at 100° C. in 4 ml of ethylene glycol. After the completion of the reaction was confirmed by HPLC, the mixture was cooled to room temperature, and 4 ml of water was added to the mixture. The mixture was extracted with 4 ml of ethyl acetate twice, dried over 3 g of anhydrous magnesium sulfate, and then concentrated under reduced pressure. The crude product was purified by silica gel column chromatography (hexane/ethyl acetate=1/1) to give 20 mg of ethyl 3-{2-chloro-5-[1-methyl-1-(4-trifluoromethyl-6H-pyrazolo[4',3':3,4]benzo[1,2-d]thiazol-2-ylcarbamoyl)-ethylamino]-benzoylamino}-propionate.

20 mg of the resulting ester derivative was suspended in a mixed solvent of 4 ml of methanol/1 ml of water, and 10 mg (0.25 mmol) of sodium hydroxide was added to the suspension, followed by stirring of the mixture at room temperature overnight. The reaction mixture was made acidic by diluted hydrochloric acid, and the mixture was extracted with 4 ml of ethyl acetate twice, dried over 3 g of anhydrous magnesium sulfate, and then concentrated under reduced pressure. The crude crystals were purified by silica gel column chromatography (hexane/ethyl acetate=1/1) to give 4.9 mg (yield: 3.5%) of the desired compound.

MASS (ESI+) m/z=569 [M+H]+, 327

After the corresponding ester intermediate was obtained according to the above process using the corresponding ester-protected aniline, hydrolysis was carried out according to the above process to give the following compound.

Synthesis Example 140

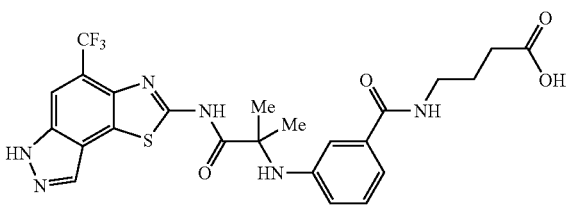

Yield: 3.5%
MASS (ESI+) m/z=549 [M+H]+, 446, 224

Synthesis Example 141

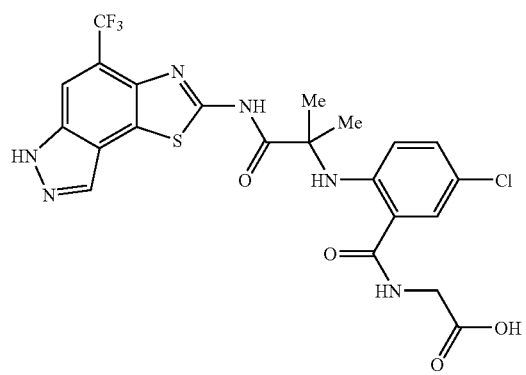

Yield: 0.9%
MASS (ESI+) m/z=555 [M+H]+, 327

Synthesis Example 142

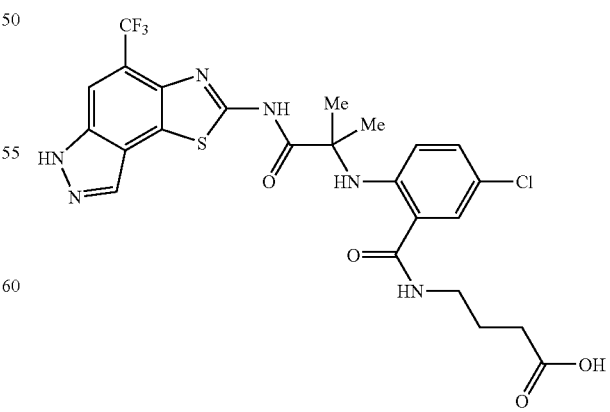

Yield: 3.1%
MASS (ESI+) m/z=583 [M+H]+

Synthesis Example 143

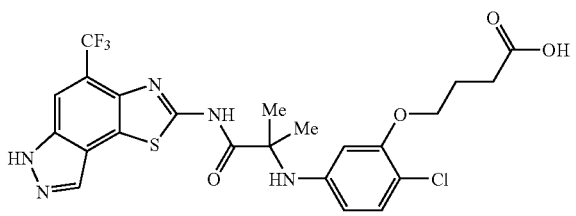

Yield: 3.8%
MASS (ESI+) m/z=556 [M+H]+, 270

Synthesis Example 144

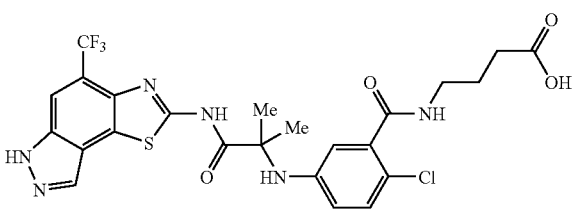

Yield: 1.6%
MASS (ESI+) m/z=583 [M+H]+, 480, 327, 241
$^1$H-NMR (300 MHz, DMSO-d$_6$) δ (ppm) 12.44 (1H, brs), 8.51 (1H, s), 8.34 (1H, s), 8.00 (1H, s), 7.14 (1H, d, J=8.7 Hz), 6.58 (1H, d, J=2.7 Hz), 6.43 (1H, dd, J=8.7, 2.7 Hz), 6.25 (1H, brs), 3.14-3.21 (2H, m), 2.28 (2H, t, J=7.8 Hz), 1.65-1.72 (2H, m), 1.58 (6H, s)

Synthesis Example 145

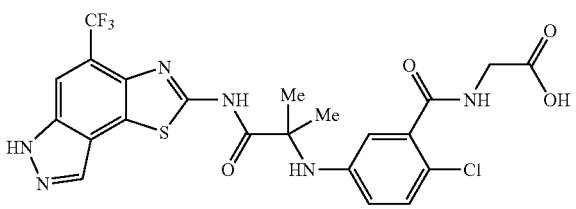

Yield: 6.1%
MASS (ESI+) m/z=555 [M+H]+, 327

Preparation Examples

The following indicates typical formulations provided by the present invention.

Preparation Example 1

| Tablets | |
|---|---|
| Compound of present invention | 10 g |
| Lactose | 260 g |

-continued

| Tablets | |
|---|---|
| Microcrystalline cellulose | 600 g |
| Cornstarch | 350 g |
| Hydroxypropyl cellulose | 100 g |
| CMC-Ca | 150 g |
| Magnesium stearate | 30 g |
| Total | 1,500 g |

The above components are mixed in accordance with ordinary methods followed by producing 10,000 sugar-coated tablets containing 1 mg of active ingredient per tablet.

Preparation Example 2

| Capsules | |
|---|---|
| Compound of present invention | 10 g |
| Lactose | 440 g |
| Microcrystalline cellulose | 1,000 g |
| Magnesium stearate | 50 g |
| Total | 1,500 g |

The above components are mixed in accordance with ordinary methods followed by filling into gelatin capsules to produce 10,000 capsules containing 1 mg of active ingredient per capsule.

Preparation Example 3

| Soft Capsules | |
|---|---|
| Compound of present invention | 10 g |
| PEG400 | 479 g |
| Saturated fatty acid triglyceride | 1,500 g |
| Peppermint oil | 1 g |
| Polysorbate 80 | 10 g |
| Total | 2,000 g |

The above components are mixed in accordance with ordinary methods followed by filling into no. 3 soft gelatin capsules to produce 10,000 soft capsules containing 1 mg of active ingredient per capsule.

Preparation Example 4

| Ointment | |
|---|---|
| Compound of present invention | 1.0 g |
| Liquid paraffin | 10.0 g |
| Cetanol | 20.0 g |
| White vaseline | 68.4 g |
| Ethylparabene | 0.1 g |
| l-menthol | 0.5 g |
| Total | 100.0 g |

The above components are mixed in accordance with ordinary methods to obtain a 1% ointment.

Preparation Example 5

| Suppository | |
|---|---|
| Compound of present invention | 1 g |
| Witepsol H15* | 478 g |
| Witepsol W35* | 520 g |
| Polysorbate 80 | 1 g |
| Total | 1,000 g |

*Trade name of triglyceride-based compound

The above components are melted and mixed in accordance with ordinary methods followed by pouring into a suppository container and solidifying by cooling to produce 1,000 1 g suppositories containing 1 mg of active ingredient.

Preparation Example 6

| Injection Preparation | |
|---|---|
| Compound of present invention | 1 mg |
| Distilled water for injection | 5 mL |

The above components are used by dissolving at the time of use.

Pharmacological Test Examples

Pharmacological Test 1

Inhibitory Activity Against βark1

(1) Production of Recombinant Human βARK1

Human βARK1 was amplified by PCR based on the base sequence of human βARK1 mRNA registered in GenBank (Accession No. M80776) using a human leukocyte cDNA library (Gibco BRL Cat. No. 10421-022) as a template. The amplified cDNA fragment was inserted into a pBacPAK8 vector (Clontech) to construct a plasmid.

Recombinant human βARK1 was expressed using the BacPAK Baculovirus Expression System (Clontech, Cat. No. K1601-1). $1 \times 10^6$ Sf-9 cells were adhered to a 35 mm dish in 2.5 mL of TMN-FH Insect Medium containing 10 vol % FBS (Pharminogen, Cat. No. PM-21227M) and cultured overnight at 27° C. On the following day, the medium was removed and 500 ng of the above plasmid, BacPAK6 viral DNA cleaved with Bsu36I (5 μL) and 1.5 mL of the same medium mixed with 4 μL of Bacfectin were added followed by culturing for 5 hours, further adding 1.5 mL of medium and subsequently culturing for 5 days. This co-transfection resulted in homologous recombination, and constructed a recombinant virus for expressing βARK1 in Sf-9 cells. The culture supernatant after 5 days was recovered and a plaque assay was carried out to isolate single plaques. These were then infected into Sf-9 cells and the resulting culture supernatant was designated as Passage 1 ($1-3 \times 10^{11}$ pfu/mL). Passage 1 was added to $3 \times 10^7$ Sf-9 cells to a multiplicity of infection (MOI) of 0.1 (pfu/cell), suspension culturing was carried out for 5 days using a spinner flask, and the resulting culture supernatant was designated as Passage 2 ($4 \times 10^{10}$ pfu/mL) and used as a viral liquid for large-volume expression.

Sf-9 cells at $3 \times 10^9$ cells/200 mL were infected by adding Passage 2 to an MOI of 100 followed by addition of medium to bring to a liquid volume of 2 L and further culturing for 3 days. After recovering the cells by centrifugation and washing three times with PBS, the cells were suspended in 100 mL of Lysis Buffer (20 mmol/L HEPES-HCl (pH 7.2), 5 mmol/L EDTA, 3 mmol/L phenylmethylsulfonyl fluoride (PMSF)). After lysing the cells by ultrasonic treatment at low temperature, the supernatant was recovered by centrifuging (45,000× g, 15 minutes) (sup1). NaCl was added to the resulting supernatant to a final concentration of 250 mmol/L followed by ultracentrifugation (300,000×g, 60 minutes) and using the subsequent supernatant as a crude cell extract (sup2).

Purification was carried out with reference to the literature (Benovic, J. L., Methods Enzymol. 1991; 200: 351-362; Kim, C. M. et al., Receptor 1993; 3: 39-55; Sohlemann, P. et al., FEBS Letters 1993; 324: 59-62). The crude cell extract was accurately brought to a volume of 400 mL with Buffer C (20 mmol/L HEPES-HCl (pH 7.2), 5 mmol/L EDTA, 0.02 vol % Triton X-100) followed by loading onto a 50 mL SP-Sepharose FF (Amersham Pharmacia Biotech) column equilibrated with Buffer C. After washing the column with a Wash Buffer (50 mmol/L NaCl, Buffer C), the column was eluted with an NaCl concentration gradient (50 to 300 mmol/L NaCl for 125 minutes, flow rate: 4 mL/min). ETA was carried out on each fraction using anti-GRK2 antibody (Santa-Cruz Cat. No. SC-562) and the positive fractions were collected (GRK2=βARK1). This was then diluted three-fold with Buffer C and loaded on a 5 mL HiTrap Heparin column (Amersham Pharmacia Biotech) column equilibrated with Buffer C. After washing the column with Wash Buffer (100 mmol/L NaCl, Buffer C), the column was eluted with an NaCl concentration gradient (100 to 600 mmol/L NaCl for 100 minutes, flow rate: 1 mL/min). The positive fractions as determined by ETA were collected and stored in a freezer at −80° C.

(2) Measurement of βARK1 Inhibitory Activity

A synthetic peptide having an amino acid sequence of biotinated-RRREEEEESAAA was used in accordance with a previous report (Chen, C. Y. et al., J. Biol. Chem. 1993; 268: 7825-7831). This synthetic peptide can also be synthesized with reference to known synthesis methods (for example, Chen, C. Y. et al., J. Biol. Chem. 1993; 268: 7825-7831, Biochemistry 1991; 30: 5118-5125). 2 μl of a DMSO solution in which the test compound was diluted to as to be 26 times the final concentration was dispensed into a 96-well plate (round bottom) (Falcon 351190) (final concentration: 4 vol % DMSO). A substrate solution (1 mmol/L peptide, 20 mmol/L Tris-HCl (pH 7.5), 2 mmol/L EDTA, 7.5 mmol/L MgCl$_2$, 80 μmol/L ATP, 0.005 vol % Triton X-100), to which was added [γ-$^{33}$P]ATP (Amersham Pharmacia Biotech, Cat. No. AH9968) equivalent to 9.25 kBq/well, was prepared, and 25 μL of this substrate solution were added to a plate in which was dispensed a compound followed by shaking for 3 minutes. 25 μl of an enzyme solution mixed with βARK1 (20 mmol/L Tris-HCl (pH 7.5), 2 mmol/L EDTA, 7.5 mmol/L MgCl$_2$, 19 to 38 nmol/L βARK1, 0.005 volt Triton X-100) were then added followed by further shaking for 3 minutes to initiate the phosphorylation reaction at room temperature. After 60 minutes, 40 μl of the reaction solution were added to a Multiscreen MA-PH plate (Millipore, Cat. No. MAPH NOB10), pre-wetted with a 100 mmol/L aqueous phosphoric acid solution containing 100 μL of 0.01 vol % Triton X-100 and filled with 150 μL of the same solution, followed by shaking for 10 minutes at room temperature. After shaking for 10 minutes, aspiration filtration was carried out using the Multiscreen Vacuum Manifold followed by washing three times with 100 mmol/L aqueous phosphoric acid solution containing 180 μL of 0.01 vol % Triton X-100 to remove free [γ-$^{33}$P]ATP and test compound. After removing the underdrain from a PH plate, the PH plate was dried in a 50° C. oven followed by the addition of 30 μL of SuperMix liquid scintillation cocktail (Wallac) and measuring radioactivity using the MicroBeta 1450 PLUS (Wallac) 2 hours after permeating through a phosphocellulose membrane.

GraphPad PRISM Ver. 3.0 (GraphPad Software Inc.) was used to calculate $IC_{50}$ values. $IC_{50}$ values were calculated by selecting the calculation formula for non-linear regression analysis "Sigmoidal dose response" by assigning an inhibition rate of 100% for data obtained in the absence of enzyme addition or data obtained by adding a termination buffer prior to addition of enzyme to the substrate. Those results are shown in Table 2. Based on the results of Table 2, compounds of the present invention are recognized to have extremely superior βARK1 inhibitory activity. Accordingly, compounds of the present invention were suggested to be useful as preventives or therapeutics for heart failure.

TABLE 2

Results

| Synthesis Example No. | βARK1 IC50 (μM) |
| --- | --- |
| 6 | 0.0040 |
| 16 | 0.0083 |
| 24 | 0.0080 |
| 30 | 0.0098 |
| 33 | 0.0078 |
| 35 | 0.0088 |
| 53 | 0.0020 |
| 55 | 0.0063 |
| 56 | 0.0032 |
| 58 | 0.0064 |
| 60 | 0.0045 |
| 75 | 0.0088 |
| 76 | 0.0093 |
| 81 | 0.0083 |
| 82 | 0.0093 |
| 85 | 0.0099 |
| 95 | 0.0087 |
| 97 | 0.0120 |
| 117 | 0.0039 |
| 118 | 0.0087 |
| 120 | 0.0037 |
| 121 | 0.0046 |
| 126 | 0.0075 |
| 127 | 0.0062 |
| 128 | 0.0028 |
| 129 | 0.0039 |
| 132 | 0.0077 |
| 135 | 0.0032 |
| 139 | 0.0079 |
| 144 | 0.0077 |
| 145 | 0.0077 |

Pharmacological Test Example 2

Inhibitory Activities Against Aurora A, CDK1/Cyclin B Complex, CDK2/Cyclin E Complex and CDK3/Cyclin E Complex Inhibitory activity against Aurora A, CDK1/Cyclin B complex, CDK2/Cyclin E complex and CDK3/Cyclin E complex were measured by in vitro kinase assay using recombinant proteins. The assays were carried out by using recombinant proteins (Upstate Inc.) for Aurora A, CDK1/Cyclin B complex, CDK2/Cyclin E complex and CDK3/Cyclin E complex (respective cat. nos. 14-511, 14-450, 14-448 and 14-487), in accordance with the procedure described in the product instructions thereof. The 50% inhibitory concentrations ($IC_{50}$ values) were calculated by assigning measured values in the case of not containing a test compound to an inhibition of 0%, and assigning measured values in the case of not containing a test compound and enzyme to an inhibition of 100%.

$IC_{50}$ values of compounds of the present invention for Aurora A are shown in Table 3, those for CDK1/Cyclin B complex are shown in Table 4, those for CDK2/Cyclin E complex are shown in Table 5, and those for CDK3/Cyclin E complex are shown in Table 6.

Compounds of the present invention inhibited activities of Aurora A, CDK1/Cyclin B complex, CDK2/Cyclin E complex and CDK3/Cyclin E complex. On the basis of these results, compounds of the present invention are expected to inhibit proliferation of tumor cells.

TABLE 3

Inhibitory Activity Against Aurora A

| Synthesis Example No. | Aurora A IC50 (nM) |
| --- | --- |
| 2 | 148 |
| 6 | 257 |
| 16 | 278 |
| 22 | 387 |
| 23 | 47 |
| 25 | 137 |
| 27 | 115 |
| 33 | 29 |
| 34 | 332 |
| 35 | 428 |
| 43 | 347 |
| 44 | 107 |
| 47 | 148 |
| 49 | 265 |
| 50 | 426 |
| 53 | 227 |
| 55 | 185 |
| 60 | 163 |
| 66 | 294 |
| 75 | 472 |
| 81 | 444 |
| 82 | 14 |
| 84 | 247 |
| 85 | 71 |
| 86 | 66 |
| 95 | 340 |
| 98 | 65 |
| 99 | 142 |
| 101 | 118 |
| 102 | 39 |
| 109 | 364 |
| 117 | 317 |
| 118 | 236 |
| 120 | 164 |
| 121 | 307 |
| 122 | 168 |
| 126 | 58 |
| 128 | 39 |
| 129 | 113 |
| 131 | 94 |
| 135 | 40 |
| 136 | 19 |
| 138 | 263 |
| 139 | 106 |
| 140 | 247 |
| 144 | 88 |
| 145 | 76 |

TABLE 4

Inhibitory Activity Against CDK1/Cyclin B

| Synthesis Example No. | CDK1/cyclin B IC50 (nM) |
|---|---|
| 6 | 255 |
| 9 | 372 |
| 23 | 150 |
| 33 | 115 |
| 53 | 420 |
| 55 | 73 |
| 58 | 186 |
| 60 | 73 |
| 75 | 128 |
| 81 | 377 |
| 82 | 20 |
| 84 | 205 |
| 85 | 1.8 |
| 86 | 483 |
| 90 | 365 |
| 95 | 105 |
| 99 | 140 |
| 101 | 39 |
| 102 | 105 |
| 116 | 486 |
| 117 | 358 |
| 122 | 197 |
| 126 | 145 |
| 132 | 379 |
| 135 | 83 |
| 136 | 446 |
| 137 | 39 |
| 138 | 53 |
| 139 | 238 |
| 140 | 446 |
| 144 | 297 |
| 145 | 259 |

TABLE 5

Inhibitory Activity Against CDK2/Cyclin E

| Synthesis Example No. | CDK2/cyclinE IC50 (nM) |
|---|---|
| 2 | 82 |
| 3 | 199 |
| 4 | 335 |
| 6 | 26 |
| 8 | 171 |
| 9 | 40 |
| 11 | 192 |
| 13 | 417 |
| 14 | 224 |
| 15 | 40 |
| 16 | 37 |
| 19 | 190 |
| 23 | 30 |
| 24 | 50 |
| 25 | 366 |
| 30 | 172 |
| 31 | 372 |
| 33 | 33 |
| 35 | 45 |
| 39 | 143 |
| 40 | 340 |
| 42 | 434 |
| 44 | 160 |
| 47 | 260 |
| 50 | 435 |
| 53 | 51 |
| 55 | 44 |
| 56 | 390 |
| 58 | 107 |
| 60 | 37 |
| 72 | 335 |
| 74 | 302 |
| 75 | 131 |
| 76 | 294 |
| 79 | 171 |
| 80 | 154 |
| 81 | 93 |
| 82 | 15 |
| 83 | 343 |
| 84 | 44 |
| 85 | 2.4 |
| 86 | 274 |
| 88 | 449 |
| 89 | 225 |
| 90 | 160 |
| 95 | 23 |
| 96 | 347 |
| 98 | 300 |
| 99 | 20 |
| 100 | 391 |
| 101 | 30 |
| 102 | 76 |
| 104 | 412 |
| 105 | 205 |
| 106 | 55 |
| 109 | 56 |
| 110 | 320 |
| 111 | 100 |
| 114 | 83 |
| 115 | 154 |
| 116 | 245 |
| 117 | 19 |
| 118 | 116 |
| 120 | 64 |
| 121 | 110 |
| 122 | 56 |
| 123 | 141 |
| 126 | 39 |
| 127 | 128 |
| 128 | 28 |
| 129 | 86 |
| 131 | 277 |
| 132 | 20 |
| 134 | 339 |
| 135 | 52 |
| 136 | 295 |
| 137 | 40 |
| 138 | 37 |
| 139 | 168 |
| 140 | 428 |
| 144 | 249 |
| 145 | 194 |

TABLE 6

Inhibitory Activity Against CDK3/Cyclin E

| Synthesis Example No. | CDK3/cyclinE IC50 (nM) |
|---|---|
| 2 | 128 |
| 3 | 391 |
| 4 | 468 |
| 6 | 28 |
| 9 | 81 |
| 11 | 355 |
| 14 | 410 |
| 15 | 88 |

TABLE 6-continued

Inhibitory Activity Against CDK3/Cyclin E

| Synthesis Example No. | CDK3/cyclinE IC50 (nM) |
|---|---|
| 16 | 50 |
| 18 | 380 |
| 19 | 242 |
| 23 | 47 |
| 24 | 75 |
| 25 | 448 |
| 30 | 128 |
| 31 | 353 |
| 33 | 33 |
| 35 | 80 |
| 39 | 367 |
| 44 | 157 |
| 47 | 343 |
| 53 | 45 |
| 55 | 23 |
| 56 | 304 |
| 58 | 47 |
| 60 | 16 |
| 66 | 333 |
| 67 | 371 |
| 72 | 180 |
| 74 | 163 |
| 75 | 41 |
| 76 | 124 |
| 79 | 266 |
| 80 | 165 |
| 81 | 55 |
| 82 | 5.9 |
| 84 | 44 |
| 85 | 0.60 |
| 86 | 85 |
| 88 | 386 |
| 89 | 105 |
| 90 | 70 |
| 95 | 22 |
| 96 | 277 |
| 97 | 279 |
| 98 | 128 |
| 99 | 8.7 |
| 100 | 344 |
| 101 | 21 |
| 102 | 30 |
| 104 | 395 |
| 105 | 257 |
| 106 | 153 |
| 109 | 55 |
| 110 | 392 |
| 111 | 262 |
| 114 | 174 |
| 115 | 217 |
| 116 | 412 |
| 117 | 44 |
| 118 | 169 |
| 120 | 105 |
| 121 | 125 |
| 122 | 63 |
| 123 | 195 |
| 126 | 38 |
| 127 | 185 |
| 128 | 61 |
| 129 | 103 |
| 131 | 427 |
| 132 | 29 |
| 134 | 477 |
| 135 | 23 |
| 136 | 99 |
| 137 | 12 |
| 138 | 12 |
| 139 | 70 |
| 140 | 160 |
| 144 | 180 |
| 145 | 134 |

Pharmacological Test Example 3

Cell Proliferation Inhibitory Activity/SW620, MIAPaCa-2, DU 145, NCI-H460, MDA-MB-231, KG-1a, IGROV1 Cell Lines Evaluations were carried out using colon carcinoma cell line SW620 (Cat. No. CCL-227), lung carcinoma cell line NCI-H460 (Cat. No. HTB-177), prostate cancer cell line DU 145 (Cat. No. HTB-81), breast cancer cell line MDA-MB-231 (Cat. No. HTB26) and leukemia cell line KG-1a (Cat. No. CCL-246.1) purchased from ATCC, pancreatic cancer cell line MIAPaCa-2 (Cat. No. CRL-1420) purchased from Dainippon Pharmaceutical, and ovarian cancer cell line IGROV1 received from the Netherland Cancer Institute. The cells were cultured under the conditions recommended by the supplier for each cell line, or with respect to IGROV1, according to the method described in Cancer Res. 59: 4559-4563, 1999. Cells suspended in media were added to solutions containing the test substances at various concentrations followed by culturing in a 5% $CO_2$ incubator at 37° C. The numbers of cells were counted 4 days later with the Cell Counting Kit-8. $IC_{50}$ values were calculated by assigning measured values in the case of not containing a test substance to an inhibition of 0%, and assigning measured values in the case of not containing a test substance or cells to an inhibition of 100%.

The $IC_{50}$ values of compounds of the present invention against 7 kinds of the cell lines are shown in Tables 7 to 13.

TABLE 7

Proliferation Inhibitory Activity Against SW620

| Synthesis Example No. | SW620 IC50 (μM) |
|---|---|
| 1 | 1.6 |
| 2 | 1.2 |
| 3 | 1.7 |
| 4 | 2.0 |
| 6 | 1.5 |
| 11 | 1.6 |
| 16 | 1.2 |
| 19 | 2.9 |
| 20 | 1.3 |
| 22 | 1.7 |
| 23 | 0.5 |
| 24 | 0.9 |
| 25 | 1.6 |
| 30 | 1.8 |
| 31 | 2.7 |
| 33 | 0.4 |
| 35 | 0.7 |
| 39 | 2.0 |
| 40 | 2.3 |
| 42 | 2.2 |
| 50 | 2.5 |
| 53 | 1.3 |
| 55 | 0.3 |
| 56 | 1.1 |
| 58 | 0.5 |
| 59 | 2.2 |
| 60 | 0.3 |
| 67 | 3.0 |
| 72 | 2.4 |
| 74 | 2.7 |
| 75 | 0.5 |
| 76 | 0.9 |
| 79 | 2.4 |
| 80 | 2.3 |
| 81 | 0.8 |
| 82 | 0.2 |
| 84 | 1.6 |
| 85 | 0.3 |
| 88 | 2.9 |

TABLE 7-continued

Proliferation Inhibitory Activity Against SW620

| Synthesis Example No. | SW620 IC50 (μM) |
|---|---|
| 89 | 2.2 |
| 90 | 1.3 |
| 94 | 1.8 |
| 95 | 0.4 |
| 96 | 2.3 |
| 98 | 0.5 |
| 99 | 0.7 |
| 100 | 3.3 |
| 101 | 2.0 |
| 104 | 1.0 |
| 105 | 1.5 |
| 111 | 2.3 |
| 114 | 0.7 |
| 115 | 0.7 |
| 116 | 1.0 |
| 117 | 0.5 |
| 118 | 2.0 |
| 119 | 2.6 |
| 120 | 0.8 |
| 121 | 0.5 |
| 122 | 1.1 |
| 123 | 2.3 |
| 126 | 1.5 |
| 127 | 0.7 |
| 128 | 0.9 |
| 129 | 0.8 |
| 130 | 2.7 |
| 131 | 3.0 |
| 132 | 0.6 |
| 134 | 1.9 |
| 135 | 0.3 |
| 137 | 0.2 |
| 138 | 2.1 |
| 144 | 3.3 |

TABLE 8

Proliferation Inhibitory Activity Against MIAPaCa-2

| Synthesis Example No. | MIA PaCa-2 IC50 (μM) |
|---|---|
| 16 | 4.4 |
| 23 | 3.5 |
| 24 | 4.8 |
| 33 | 4.5 |
| 53 | 4.7 |
| 55 | 4.1 |
| 58 | 4.0 |
| 60 | 4.4 |
| 75 | 3.9 |
| 76 | 4.9 |
| 81 | 4.7 |
| 82 | 2.5 |
| 85 | 1.8 |
| 95 | 4.6 |
| 98 | 4.0 |
| 99 | 4.5 |
| 121 | 4.6 |
| 128 | 3.2 |
| 132 | 3.7 |
| 135 | 4.1 |
| 137 | 3.1 |
| 138 | 4.3 |

TABLE 9

Proliferation Inhibitory Activity Against DU145

| Synthesis Example No. | DU 145 IC50 (μM) |
|---|---|
| 16 | 3.2 |
| 23 | 1.6 |
| 24 | 3.2 |
| 30 | 2.7 |
| 33 | 1.7 |
| 35 | 2.5 |
| 44 | 4.5 |
| 53 | 1.5 |
| 55 | 0.9 |
| 56 | 2.5 |
| 58 | 0.9 |
| 59 | 4.2 |
| 60 | 0.9 |
| 72 | 3.5 |
| 74 | 3.9 |
| 75 | 1.1 |
| 76 | 1.8 |
| 79 | 3.1 |
| 80 | 4.1 |
| 81 | 1.1 |
| 82 | 0.4 |
| 84 | 3.4 |
| 85 | 1.3 |
| 89 | 4.5 |
| 90 | 1.9 |
| 94 | 4.2 |
| 95 | 1.1 |
| 96 | 3.6 |
| 98 | 4.4 |
| 99 | 1.7 |
| 101 | 4.4 |
| 115 | 3.2 |
| 116 | 3.4 |
| 117 | 2.2 |
| 120 | 3.3 |
| 121 | 3.4 |
| 122 | 4.5 |
| 126 | 3.7 |
| 127 | 3.0 |
| 128 | 1.7 |
| 129 | 2.6 |
| 132 | 1.4 |
| 135 | 0.5 |
| 137 | 0.4 |
| 138 | 2.3 |

TABLE 10

Proliferation Inhibitory Activity Against NCI-H460

| Synthesis Example No. | NCI-H460 IC50 (μM) |
|---|---|
| 16 | 3.2 |
| 23 | 1.4 |
| 25 | 3.2 |
| 30 | 4.1 |
| 33 | 3.6 |
| 53 | 2.4 |
| 55 | 0.8 |
| 56 | 2.5 |
| 58 | 1.3 |
| 60 | 1.5 |
| 75 | 2.0 |
| 76 | 1.5 |
| 81 | 1.3 |
| 82 | 0.4 |
| 84 | 3.2 |
| 85 | 1.2 |
| 90 | 2.5 |
| 94 | 2.0 |

TABLE 10-continued

Proliferation Inhibitory Activity Against NCI-H460

| Synthesis Example No. | NCI-H460 IC50 (μM) |
|---|---|
| 95 | 1.2 |
| 96 | 3.9 |
| 98 | 1.8 |
| 99 | 4.1 |
| 117 | 2.8 |
| 120 | 1.9 |
| 121 | 2.2 |
| 122 | 4.0 |
| 126 | 4.2 |
| 127 | 3.1 |
| 128 | 1.1 |
| 129 | 2.7 |
| 132 | 1.7 |
| 135 | 0.9 |
| 137 | 0.4 |
| 138 | 1.6 |

TABLE 11

Proliferation Inhibitory Activity Against MDA-MB-231

| Synthesis Example No. | MDA-MB-231 IC50 (μM) |
|---|---|
| 3 | 4.7 |
| 6 | 2.6 |
| 16 | 4.4 |
| 23 | 1.6 |
| 24 | 3.8 |
| 33 | 2.0 |
| 53 | 4.0 |
| 55 | 3.2 |
| 58 | 4.7 |
| 60 | 4.5 |
| 75 | 3.6 |
| 76 | 4.6 |
| 81 | 4.2 |
| 82 | 2.1 |
| 84 | 4.8 |
| 85 | 2.5 |
| 90 | 4.4 |
| 94 | 2.8 |
| 98 | 2.6 |
| 99 | 3.0 |
| 104 | 4.9 |
| 114 | 4.7 |
| 115 | 3.9 |
| 117 | 2.5 |
| 122 | 3.1 |
| 127 | 4.3 |
| 128 | 4.6 |
| 132 | 1.9 |
| 135 | 1.6 |
| 137 | 1.9 |

TABLE 12

Proliferation Inhibitory Activity Against IGROV1

| Synthesis Example No. | IGROV1 IC50 (μM) |
|---|---|
| 1 | 4.6 |
| 3 | 4.9 |
| 6 | 4.3 |
| 11 | 4.8 |
| 23 | 1.3 |
| 24 | 4.6 |
| 33 | 2.7 |

TABLE 12-continued

Proliferation Inhibitory Activity Against IGROV1

| Synthesis Example No. | IGROV1 IC50 (μM) |
|---|---|
| 50 | 4.8 |
| 55 | 2.7 |
| 76 | 2.7 |
| 81 | 2.4 |
| 82 | 0.9 |
| 85 | 1.8 |
| 94 | 4.5 |
| 99 | 4.4 |
| 104 | 4.7 |
| 115 | 4.8 |
| 116 | 4.9 |
| 117 | 2.7 |
| 120 | 4.8 |
| 121 | 4.8 |
| 122 | 4.9 |
| 127 | 4.9 |
| 128 | 3.5 |
| 129 | 4.8 |
| 132 | 1.4 |
| 135 | 1.5 |
| 137 | 3.0 |
| 138 | 4.5 |

TABLE 13

Proliferation Inhibitory Activity Against KG-1a

| Synthesis Example No. | KG-1a IC50 (μM) |
|---|---|
| 1 | <0.1 |
| 2 | <0.1 |
| 3 | 0.1 |
| 4 | 0.1 |
| 5 | <0.1 |
| 6 | <0.1 |
| 9 | <0.1 |
| 11 | <0.1 |
| 14 | 0.2 |
| 16 | <0.1 |
| 20 | 0.1 |
| 22 | <0.1 |
| 23 | <0.1 |
| 24 | <0.1 |
| 25 | <0.1 |
| 26 | 0.2 |
| 27 | 0.1 |
| 33 | <0.1 |
| 34 | 0.1 |
| 35 | <0.1 |
| 39 | <0.1 |
| 40 | 0.2 |
| 42 | <0.1 |
| 43 | 0.2 |
| 44 | <0.1 |
| 47 | <0.1 |
| 49 | <0.1 |
| 50 | <0.1 |
| 53 | 0.3 |
| 55 | <0.1 |
| 56 | 0.4 |
| 58 | 0.3 |
| 60 | 0.3 |
| 75 | <0.1 |
| 76 | 0.3 |
| 81 | <0.1 |
| 82 | <0.1 |
| 84 | 0.2 |
| 85 | <0.1 |
| 95 | 0.1 |
| 98 | 0.3 |

TABLE 13-continued

Proliferation Inhibitory Activity Against KG-1a

| Synthesis Example No. | KG-1a IC50 (μM) |
|---|---|
| 99 | 0.3 |
| 100 | 0.3 |
| 104 | <0.1 |
| 105 | 0.1 |
| 106 | <0.1 |
| 108 | 0.3 |
| 109 | <0.1 |
| 111 | 0.5 |
| 114 | <0.1 |
| 115 | <0.1 |
| 116 | 0.2 |
| 117 | <0.1 |
| 118 | <0.1 |
| 119 | 0.3 |
| 120 | <0.1 |
| 121 | <0.1 |
| 122 | <0.1 |
| 124 | 0.1 |
| 126 | <0.1 |
| 127 | <0.1 |
| 128 | <0.1 |
| 129 | <0.1 |
| 132 | <0.1 |
| 134 | <0.1 |
| 135 | <0.1 |
| 137 | <0.1 |

On the basis of the results for each table, compounds of the present invention inhibited proliferation of colon cancer, lung cancer, prostate cancer, breast cancer, ovarian cancer, pancreatic cancer and leukemia cell lines in vitro. On the basis of these results, compounds of the present invention are expected to demonstrate antitumor effects in vivo as well. In addition, compounds of the present invention are expected to serve as therapeutic agents for colon cancer, lung cancer, prostate cancer, breast cancer, ovarian cancer, pancreatic cancer and leukemia.

Pharmacology Test Example 4

Evaluation of Antitumor Activity/Mouse Xenograft Model

Evaluations were carried out using human prostate cancer cells DU145 (Cat. No. HTB-81) and human colon cancer cells SW620 (Cat. No. CCL-227) purchased from ATCC. The cells were maintained according to the conditions recommended by ATCC. Cultured cells were recovered by trypsin treatment and after suspending in Hanks solution, DU145 cells were transplanted subcutaneously into the right inguinal region of Balb/c nude mice (Japan Charles River) using males for DU145 and females for SW620. Test compounds (compounds of synthesis examples 35, 60, 99 and 126 for DU145 and compounds of synthesis examples 35 and 126 for SW620) administered orally using a gastric tube once a day for 14 days in the case of DU145 or 17 days in the case of SW620 starting when the mean tumor volume of each group reached 200 to 250 mm³. Tumor volumes were measured twice a week and on the day following the final administration. Tumor volume (TV) was determined using the following calculation formula from the main axis (A) and minor axis (B) of the tumor:

$$TV = 1/2 \times A \times B \times B$$

(reference: Thomas Corbett et al., In Vivo Methods for Screening and Preclinical Testing, Anticancer Drug Development Guide, Humana Press, 1997: 75-99).

Figure 2:
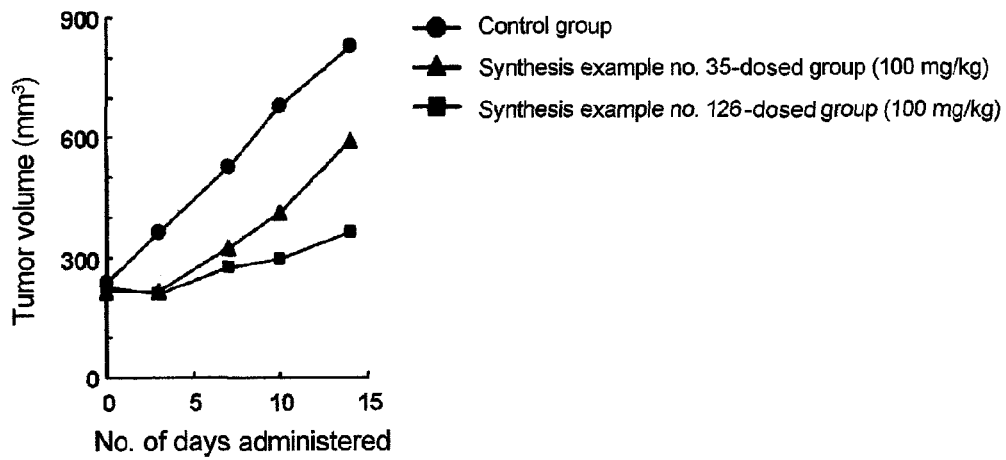
FIG. 2 shows the results of an antitumor test using nude mice transplanted with human colon cancer cells SW620. The graph shows time-based changes in tumor volume in groups dosed with synthesis example 35 (▲) and 126 (■) and in a control group (●).

As shown in FIGS. 1 and 2, compounds of the present invention inhibit tumor proliferation by oral administration in a xenograft model of human prostate cancer cells DU145 and in a xenograft model of human colon cancer cells SW620. On the basis of these results, compounds of the present invention are expected to demonstrate antitumor effects as a result of oral administration in the clinical setting as well.

INDUSTRIAL APPLICABILITY

Since compounds of the present invention demonstrate βARK-1 inhibitory activity, they can be used as preventive and therapeutic agents for heart failure, and are useful as pharmaceuticals. Moreover, since compounds of the present invention also have antitumor activity, and particularly dual inhibitory activity against Aurora kinase and CDK, they are also useful for cell proliferative diseases such as cancer.

The invention claimed is:

1. An α-Amino acid derivative of formula (1):

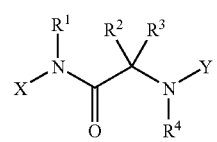

(1)

wherein, $R^1$ represents a hydrogen atom, $R^2$ and $R^3$ each independently represent a hydrogen atom; a $C_{1-4}$ alkyl group optionally substituted with a substituent(s) selected from the group consisting of a hydroxyl group, $C_{1-4}$ alkoxy group, benzyloxy group, —$CONH_2$ group and phenyl group; or phenyl group, or $R^2$ and $R^3$ together form —$(CH_2)_n$—, wherein n represents an integer of 2, 3, 4 or 5, or $R^2$ and $R^3$ form C=O together with a carbon atom to which they are attached, $R^4$ represents a hydrogen atom, or $R^4$ and $R^2$ together form —$(CH_2)_m$—, wherein m represents an integer of 1, 2, 3 or 4, Y represents a $C_{6-10}$ aryl group or $C_{4-9}$ heterocyclic group optionally substituted with substituents $R^5$, $R^6$ and $R^7$, wherein, the substituents $R^5$, $R^6$ and $R^7$ each independently represent:

a hydrogen atom;

halogen atom;

hydroxyl group;

nitro group;

cyano group;

formyl group;

—$NHCOR^{11}$, wherein, $R^{11}$ represents a hydrogen atom, $C_{1-4}$ alkyl group, $C_{3-6}$ cycloalkyl group, amino group, $C_{1-4}$ alkylamino group, di-$C_{1-4}$ alkylamino group or $C_{1-4}$ alkoxy group optionally substituted with a hydroxyl group(s);

—$SO_2NH_2$, —$SO_2NHR^{12}$, —$SO_2NR^{12}R^{13}$ or —$NHSO_2R^{12}$, wherein, $R^{12}$ and $R^{13}$ each independently represent a $C_{1-4}$ alkyl group;

amino group;

—$CONH_2$;

—$CO_2H$;

$C_{1-4}$ alkylamino group, di-$C_{1-4}$ alkylamino group, $C_{1-4}$ alkylaminocarbonyl group or di-$C_{1-4}$ alkylaminocarbonyl group,
wherein, these groups may be optionally substituted with a substituent(s) selected from the group consisting of —$CONH_2$, —$SO_2NH_2$, —$CO_2H$ and a $C_{1-4}$ alkoxycarbonyl group optionally substituted with a hydroxyl group(s);
$C_{3-6}$ cycloalkylaminocarbonyl group;
benzyloxyaminocarbonyl group;
$C_{1-4}$ alkoxyaminocarbonyl group;
N—$C_{1-4}$ alkoxy-$C_{1-4}$ alkylaminocarbonyl group;
$C_{1-4}$ alkyl group, $C_{1-4}$ alkoxy group or $C_{1-4}$ alkoxycarbonyl group,
wherein, these groups may be optionally substituted with a substituent(s) selected from the group consisting of a halogen atom, hydroxyl group, —$CONH_2$, —$SO_2NH_2$ and —$CO_2H$; or
5- to 6-membered monocyclic heterocyclic group containing 1 to 3 nitrogen atoms; and
X represents a group of formula (2):

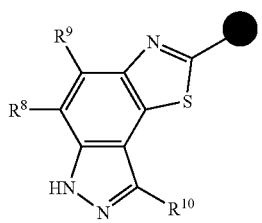

(2)

wherein,
$R^8$, $R^9$ and $R^{10}$ each independently represent:
a hydrogen atom;
halogen atom;
$C_{1-4}$ alkoxycarbonyl group;
—$CO_2H$;
nitro group; or
$C_{1-4}$ alkyl group optionally substituted with a substituent(s) selected from the group consisting of a halogen atom, hydroxyl group, $C_{1-4}$ alkoxy group, $C_{1-4}$ alkoxycarbonyl group and —$CO_2H$,
or a tautomer thereof;
or a pharmaceutically acceptable salt thereof.

2. The α-amino acid derivative or pharmaceutically acceptable salt thereof according to claim 1, wherein either one of $R^2$ or $R^3$ is a hydrogen atom, and the other is a $C_{1-4}$ alkyl group optionally substituted with a substituent(s) selected from the group consisting of a hydroxyl group, $C_{1-4}$ alkoxy group, benzyloxy group, —$CONH_2$ and phenyl group, or a phenyl group, or
$R^2$ and $R^3$ both represent hydrogen atoms or both represent $C_{1-4}$ alkyl groups, or
$R^2$ and $R^3$ together form —$(CH_2)_n$—, wherein n represents an integer of 2, 3, 4 or 5.

3. The α-amino acid derivative or pharmaceutically acceptable salt thereof according to claim 2, wherein $R^2$ and $R^3$ both represent hydrogen atoms or both represent methyl groups, or
$R^2$ and $R^3$ form cyclopropane together with a carbon atom to which they are attached.

4. The α-amino acid derivative or pharmaceutically acceptable salt thereof according to claim 1, wherein Y represents a phenyl group optionally substituted with the substituents $R^5$, $R^6$ and $R^7$, wherein $R^5$, $R^6$ and $R^7$ are as defined in claim 1.

5. The α-amino acid derivative or pharmaceutically acceptable salt thereof according to claim 1, of formula (3):

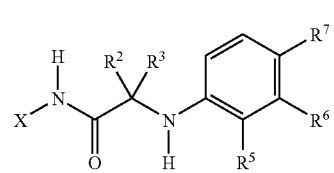

(3)

wherein, $R^2$, $R^3$, $R^5$, $R^6$, $R^7$ and X are as defined in claim 1.

6. The α-amino acid derivative or pharmaceutically acceptable salt thereof according to claim 5, wherein at least one of $R^5$, $R^6$ and $R^7$ is a hydrogen atom,
while the remaining two each independently represent a halogen atom; hydroxyl group; —$NHCOR^{11}$, wherein $R^{11}$ refers to a $C_{1-4}$ alkyl group, $C_{3-6}$ cycloalkyl group, $C_{1-4}$ alkylamino group or $C_{1-4}$ alkoxy group optionally substituted with a hydroxyl group(s); —$NHSO_2R^{12}$, wherein $R^{12}$ refers to a $C_{1-4}$ alkyl group; —$CONH_2$; $C_{1-4}$ alkylaminocarbonyl group, di-$C_{1-4}$ alkylaminocarbonyl group, wherein the $C_{1-4}$ alkylaminocarbonyl group or di-$C_{1-4}$ alkylaminocarbonyl group may be optionally substituted with a substituent(s) selected from the group consisting of —$CONH_2$, —$SO_2NH_2$, —$CO_2H$ and —$CO_2(CH_2)_pOH$, wherein p refers to an integer of 1, 2 or 3; $C_{3-6}$ cycloalkylaminocarbonyl group; benzyloxyaminocarbonyl group; $C_{1-4}$ alkoxyaminocarbonyl group; or $C_{1-4}$ alkyl group, $C_{1-4}$ alkoxy group or $C_{1-4}$ alkoxycarbonyl group, wherein the $C_{1-4}$ alkyl group, $C_{1-4}$ alkoxy group or $C_{1-4}$ alkoxycarbonyl group may be optionally substituted with a substituent(s) selected from the group consisting of a halogen atom, hydroxyl group, —$CONH_2$, —$SO_2NH_2$ and —COOH.

7. The α-amino acid derivative or pharmaceutically acceptable salt thereof according to claim 1, wherein $R^9$ is a hydrogen atom or trifluoromethyl group, and $R^8$ and $R^{10}$ are hydrogen atoms.

8. The α-amino acid derivative according to claim 1, selected from the group consisting of:
2-(4-chloro-3-hydroxyphenylamino)-N-(6H-pyrazolo[4',3':3,4]benzo[1,2-d]thiazol-2-yl)-acetamide,
2-(3-hydroxyphenylamino)-2-methyl-N-(6H-pyrazolo[4',3':3,4]benzo[1,2-d]thiazol-2-yl)-propionamide,
2-(4-chlorophenylamino)-3-hydroxy-N-(6H-pyrazolo[4',3':3,4]benzo[1,2-d]thiazol-2-yl)-propionamide,
2-(4-chlorophenylamino)-2-methyl-N-(6H-pyrazolo[4',3':3,4]benzo[1,2-d]thiazol-2-yl)-propionamide,
2-(4-chlorophenylamino)-N-(6H-pyrazolo[4',3':3,4]benzo[1,2-d]thiazol-2-yl)-propionamide,
2-(3-acetylamino-4-chlorophenylamino)-N-(6H-pyrazolo[4',3':3,4]benzo[1,2-d]thiazol-2-yl)-acetamide,
1-(4-chlorophenylamino)-N-(6H-pyrazolo[4',3':3,4]benzo[1,2-d]thiazol-2-yl)-cyclopropanecarboxamide,
2-chloro-5-[1-(6H-pyrazolo[4',3':3,4]benzo[1,2-d]thiazol-2-ylcarbamoyl)-cyclopropylamino]-benzoic acid ethyl ester,
2-(3-acetylamino-4-chlorophenylamino)-2-methyl-N-(6H-pyrazolo[4',3':3,4]benzo[1,2-d]thiazol-2-yl)-propionamide,
1-(3-acetylamino-4-fluorophenylamino)-N-(6H-pyrazolo[4',3':3,4]benzo[1,2-d]thiazol-2-yl)-cyclopropane-carboxamide, 1-(4-fluoro-3-propionylamino-phenylamino)-N-(6H-pyrazolo[4',3':3,4]benzo[1,2-d]thiazol-2-yl)cyclopropane-carboxamide,
2-(4-chloro-3-propionylamino-phenylamino)-2-methyl-N-(6H-pyrazolo[4',3':3,4]benzo[1,2-d]thiazol-2-yl)-propionamide,
2-(3-acetylamino-4-chlorophenylamino)-2-methyl-N-(4-trifluoromethyl-6H-pyrazolo[4',3':3,4]benzo[1,2-d]thiazol-2-yl)-propionamide,
2-chloro-N-methyl-5-[1-(6H-pyrazolo[4',3':3,4]benzo[1,2-d]thiazol-2-ylcarbamoyl)-cyclopropylamino]-benzamide,
2-chloro-N-methyl-5-[1-methyl-1-(4-trifluoromethyl-6H-pyrazolo[4',3':3,4]benzo[1,2-d]thiazol-2-ylcarbamoyl)-ethylamino]-benzamide,
2-(4-chloro-3-propionylamino-phenylamino)-2-methyl-N-(4-trifluoromethyl-6H-pyrazolo[4',3':3,4]benzo[1,2-d]thiazol-2-yl)-propionamide,
2-chloro-5-[1-methyl-1-(4-trifluoromethyl-6H-pyrazolo[4',3':3,4]benzo[1,2-d]thiazol-2-ylcarbamoyl)-ethylamino]-benzamide,
1-(4-chlorophenylamino)-N-(4-methyl-6H-pyrazolo[4',3':3,4]benzo[1,2-d]thiazol-2-yl)-cyclopropanecarboxamide,
N-ethyl-2-fluoro-5-[1-methyl-1-(4-trifluoromethyl-6H-pyrazolo[4',3':3,4]benzo[1,2-d]thiazol-2-ylcarbamoyl)-ethylamino]-benzamide,
2-chloro-N-ethyl-5-[1-methyl-1-(4-trifluoromethyl-6H-pyrazolo[4',3':3,4]benzo[1,2-d]thiazol-2-ylcarbamoyl)-ethylamino]-benzamide,
2-(3-acetylamino-4-chlorophenylamino)-2-phenyl-N-(4-trifluoromethyl-6H-pyrazolo[4',3':3,4]benzo[1,2-d]thiazol-2-yl)-acetamide,
2-chloro-N-cyclopropyl-5-[1-methyl-1-(4-trifluoro-methyl-6H-pyrazolo[4',3':3,4]benzo[1,2-d]thiazol-2-ylcarbamoyl)-ethylamino]-benzamide,
2-(4-fluoro-3-propionylamino-phenylamino)-2-methyl-N-(4-trifluoromethyl-6H-pyrazolo[4',3':3,4]benzo[1,2-d]thiazol-2-yl)-propionamide,
2-(3-acetylamino-4-fluorophenylamino)-2-methyl-N-(4-trifluoromethyl-6H-pyrazolo[4',3':3,4]benzo[1,2-d]thiazol-2-yl)-propionamide,
2-methyl-2-(3-sulfamoylphenylamino)-N-(4-trifluoromethyl-6H-pyrazolo[4',3':3,4]benzo[1,2-d]thiazol-2-yl)-propionamide,
N-carbamoylmethyl-2-chloro-5-[1-methyl-1-(4-trifluoromethyl-6H-pyrazolo[4',3':3,4]benzo[1,2-d]thiazol-2-ylcarbamoyl)-ethylamino]-benzamide,
3-{2-chloro-5-[1-methyl-1-(4-trifluoromethyl-6H-pyrazolo[4',3':3,4]benzo[1,2-d]thiazol-2-ylcarbamoyl)-ethylamino]-benzoylamino}-propionic acid,
2-(4-chloro-3-hydroxyphenylamino)-2-methyl-N-(4-trifluoromethyl-6H-pyrazolo[4',3':3,4]benzo[1,2-d]thiazol-2-yl)-propionamide,
4-{2-chloro-5-[1-methyl-1-(4-trifluoromethyl-6H-pyrazolo[4',3':3,4]benzo[1,2-d]thiazol-2-ylcarbamoyl)-ethylamino]-benzoylamino}-butyric acid,
{2-chloro-5-[1-methyl-1-(4-trifluormethyl-6H-pyrazolo[4',3':3,4]benzo[1,2-d]thiazol-2-ylcarbamoyl)-ethylamino]-benzoylamino}-acetic acid,
2-[4-chloro-3-(2-oxo-2,3-dihydroimidazol-1-yl)-phenylamino]-2-methyl-N-(4-trifluoromethyl-6H-pyrazolo[4',3':3,4]benzo[1,2-d]thiazol-2-yl)-propionamide,
2-[4-chloro-3-(2,3-dihydroxy-propoxy)-phenylamino]-2-methyl-N-(4-trifluoromethyl-6H-pyrazolo[4',3':3,4]benzo[1,2-d]thiazol-2-yl)-propionamide, and
2-(3-methoxyphenylamino)-N-(6H-pyrazolo[4',3':3,4]benzo[1,2-d]thiazol-2-yl)-propionamide,
or a pharmaceutically acceptable salt of any one of the above.

9. The α-amino acid derivative according to claim 1, selected from the group consisting of:
2-(4-chloro-3-hydroxyphenylamino)-N-(6H-pyrazolo[4',3':3,4]benzo[1,2-d]thiazol-2-yl)-acetamide,
2-(3-hydroxyphenylamino)-2-methyl-N-(6H-pyrazolo[4',3':3,4]benzo[1,2-d]thiazol-2-yl)-propionamide,
2-(4-chlorophenylamino)-3-hydroxy-N-(6H-pyrazolo[4',3':3,4]benzo[1,2-d]thiazol-2-yl)-propionamide,
2-(4-chlorophenylamino)-2-methyl-N-(6H-pyrazolo[4',3':3,4]benzo[1,2-d]thiazol-2-yl)-propionamide,
2-(4-chlorophenylamino)-N-(6H-pyrazolo[4',3':3,4]benzo[1,2-d]thiazol-2-yl)-propionamide,
2-(3-acetylamino-4-chlorophenylamino)-N-(6H-pyrazolo[4',3':3,4]benzo[1,2-d]thiazol-2-yl)-acetamide,
1-(4-chlorophenylamino)-N-(6H-pyrazolo[4',3':3,4]benzo[1,2-d]thiazol-2-yl)-cyclopropanecarboxamide,
2-chloro-5-[1-(6H-pyrazolo[4',3':3,4]benzo[1,2-d]thiazol-2-ylcarbamoyl)-cyclopropylamino]-benzoic acid ethyl ester,
2-(3-acetylamino-4-chlorophenylamino)-2-methyl-N-(6H-pyrazolo[4',3':3,4]benzo[1,2-d]thiazol-2-yl)-propionamide,
1-(3-acetylamino-4-fluorophenylamino)-N-(6H-pyrazolo[4',3':3,4]benzo[1,2-d]thiazol-2-yl)cyclopropane-carboxamide,
1-(4-fluoro-3-propionylamino-phenylamino)-N-(6H-pyrazolo[4',3':3,4]benzo[1,2-d]thiazol-2-yl)cyclopropane-carboxamide,
2-(4-chloro-3-propionylamino-phenylamino)-2-methyl-N-(6H-pyrazolo[4',3':3,4]benzo[1,2-d]thiazol-2-yl)-propionamide,
2-(3-acetylamino-4-chlorophenylamino)-2-methyl-N-(4-trifluoromethyl-(6H-pyrazolo[4',3':3,4]benzo[1,2-d]thiazol-2-yl)-propionamide,
2-chloro-N-methyl-5-[1-(6H-pyrazolo[4',3':3,4]benzo[1,2-d]thiazol-2-ylcarbamoyl)-cyclopropylamino]-benzamide,
2-chloro-N-methyl-5-[1-methyl-1-(4-trifluoromethyl-6H-pyrazolo[4',3':3,4]benzo[1,2-d]thiazol-2-ylcarbamoyl)-ethylamino]-benzamide,
2-(4-chloro-3-propionylamino-phenylamino)-2-methyl-N-(4-trifluoromethyl-6H-pyrazolo[4',3':3,4]benzo[1,2-d]thiazol-2-yl)-propionamide,
2-chloro-5-[1-methyl-1-(4-trifluoromethyl-6H-pyrazolo[4',3':3,4]benzo[1,2-d]thiazol-2-ylcarbamoyl)-ethylamino]-benzamide,
1-(4-chlorphenylamino)-N-(4-methyl-6H-pyrazolo[4',3':3,4]benzo[1,2-d]thiazol-2-yl)-cyclopropanecarboxamide,
N-ethyl-2-fluoro-5-[1-methyl-1-(4-trifluoromethyl-6H-pyrazolo[4',3':3,4]benzo[1,2-d]thiazol-2-ylcarbamoyl)-ethylamino]-benzamide,
2-chloro-N-ethyl-5-[1-methyl-1-(4-trifluoromethyl-6H-pyrazolo[4',3':3,4]benzo[1,2-d]thiazol-2-ylcarbamoyl)-ethylamino]-benzamide,
2-(3-acetylamino-4-chlorophenylamino)-2-phenyl-N-(4-trifluoromethyl-6H-pyrazolo[4',3':3,4]benzo[1,2-d]thiazol-2-yl)-acetamide,
2-chloro-N-cyclopropyl-5-[1-methyl-1-(4-trifluoro-methyl-6H-pyrazolo[4',3':3,4]benzo[1,2-d]thiazol-2-ylcarbamoyl)-ethylamino]-benzamide, 2-(4-fluoro-3-propionylamino-phenylamino)-2-methyl-N-(4-trifluoromethyl-6H-pyrazolo[4',3':3,4]benzo[1,2-d]thiazol-2-yl)-propionamide, 2-(3-acetylamino-4-fluorophenylamino)-2-methyl-N-(4-trifluoromethyl-6H-pyrazolo[4',3':3,4]benzo[1,2-d]thiazol-2-yl)-propionamide, 2-methyl-2-(3-sulfamoylphenylamino)-N-(4-trifluoromethyl-6H-pyrazolo[4',3':3,4]benzo[1,2-d]thiazol-2-yl)-propionamide, N-carbamoylmethyl-2-chloro-5-[1-methyl-1-(4-trifluoromethyl-6H-pyrazolo[4',3':3,4]benzo[1,2-d]thiazol-2-ylcarbamoyl)-ethylamino]-benzamide, 3-{2-chloro-5-[1-methyl-1-(4-trifluoromethyl)-6H-pyrazolo[4',3':3,4]benzo[1,2-d]thiazol-2-ylcarbamoyl-ethylamino]-benzoylamino}-propionic acid 2-(4-chloro-3-hydroxyphenylamino)-2-methyl-N-(4-trifluoromethyl-6H-pyrazolo[4',3':3,4]benzo[1,2-d]thiazol-2-yl)-propionamide, 4-{2-chloro-5-[1-methyl-1-(4-trifluoromethyl-6H-pyrazolo[4',3':3,4]benzo[1,2-d]thiazol-2-ylcarbamoyl)-ethylamino]-benzoylamino}-butyric acid, {2-chloro-5-[1-methyl-1-(4-trifluormethyl-6H-pyrazolo[4',3':3,4]benzo[1,2-d]thiazol-2-ylcarbamoyl)-ethylamino]-benzoylamino}-acetic acid, and 2-[4-chloro-3-(2-oxo-2,3-dihydroimidazol-1-yl)-phenylamino]-2-methyl-N-(4-trifluoromethyl-6H-pyrazolo[4',3':3,4]benzo[1,2-d]thiazol-2-yl)-propionamide, or a pharmaceutically acceptable salt of any one of the above.

10. The α-amino acid derivative according to claim 1, selected from the group consisting of:

2-(3-acetylamino-4-chlorophenylamino)-2-methyl-N-(6H-pyrazolo[4',3':3,4]benzo[1,2-d]thiazol-2-yl)-propionamide, 2-[4-chloro-3-(2,3-dihydroxy-propoxy)-phenylamino]-2-methyl-N-(4-trifluoromethyl-6H-pyrazolo[4',3':3,4]benzo[1,2-d]thiazol-2-yl)-propionamide, 2-(3-methoxyphenylamino)-N-(6H-pyrazolo[4',3':3,4]benzo[1,2-d]thiazol-2-yl)-propionamide, 2-(4-chlorophenylamino)-2-methyl-N-(6H-pyrazolo[4',3':3,4]benzo[1,2-d]thiazol-2-yl)-propionamide, 2-(3-acetylamino-4-chlorophenylamino)-N-(6H-pyrazolo[4',3':3,4]benzo[1,2-d]thiazol-2-yl)-acetamide, 1-(3-acetylamino-4-fluorophenylamino)-N-(6H-pyrazolo[4',3':3,4]benzo[1,2-d]thiazol-2-yl)-cyclopropane-carboxamide, 2-chloro-N-methyl-5-[1-(6H-pyrazolo[4',3':3,4]benzo[1,2-d]thiazol-2-ylcarbamoyl)-cyclopropylamino]-benzamide, 2-chloro-N-methyl-5-[1-methyl-1-(4-trifluoromethyl-6H-pyrazolo[4',3':3,4]benzo[1,2-d]thiazol-2-ylcarbamoyl)-ethylamino]-benzamide, 2-chloro-N-ethyl-5-[1-methyl-1-(4-trifluoromethyl-6H-pyrazolo[4',3':3,4]benzo[1,2-d]thiazol-2-ylcarbamoyl)-ethylamino]-benzamide, 2-methyl-2-(3-sulfamoylphenylamino)-N-(4-trifluoromethyl-6H-pyrazolo[4',3':3,4]benzo[1,2-d]thiazol-2-yl)-propionamide, N-carbamoylmethyl-2-chloro-5-[1-methyl-1-(4-trifluoromethyl-6H-pyrazolo [4',3':3,4]benzo[1,2-d]thiazol-2-ylcarbamoyl)-ethylamino]-benzamide, and 4-{2-chloro-5-[1-methyl-1-(4-trifluoromethyl-6H-pyrazolo[4',3':3,4]benzo[1,2-d]thiazol-2-ylcarbamoyl)-ethylamino]-benzoylamino}-butyric acid, or a pharmaceutically acceptable salt of any one of the above.

11. A pharmaceutical composition comprising:

as an active ingredient, an effective amount of the α-amino acid derivative according to claim 1 or a pharmaceutically acceptable salt thereof; and a pharmaceutically acceptable carrier.

12. A method for treating heart failure comprising:

administering to a patient in need thereof, as an active ingredient, an effective amount of the α-amino acid derivative according to claim 1, or a pharmaceutically acceptable salt thereof.

13. A method for treating a tumor in a patient, comprising: administering to a patient in need thereof, as an active ingredient, an effective amount of the α-amino acid derivative according to claim 1 or a pharmaceutically acceptable salt thereof, wherein the tumor is selected from colon cancer, rectal cancer, lung cancer, breast cancer, ovarian cancer, prostate cancer and leukemia.

14. The α-amino acid derivative according to claim 1 or a pharmaceutically acceptable salt thereof according to claim 1, which has dual Aurora kinase/cyclin-dependent kinase activity.

* * * * *